US010590456B2

(12) United States Patent
Jewett et al.

(10) Patent No.: US 10,590,456 B2
(45) Date of Patent: Mar. 17, 2020

(54) RIBOSOMES WITH TETHERED SUBUNITS

(71) Applicants: Northwestern University, Evanston, IL (US); The Board of Trustees of the University of Illinois, Urbana, IL (US)

(72) Inventors: Michael Christopher Jewett, Evanston, IL (US); Do Soon Kim, Evanston, IL (US); Erik D. Carlson, Chicago, IL (US); Alexander S. Mankin, River Forest, IL (US); Cedric Orelle, Chicago, IL (US); Teresa Szal, Forest Park, IL (US); Anne E. d'Aquino, Evanston, IL (US)

(73) Assignees: Northwestern University, Evanston, IL (US); The Board of Trustees of the University of Illinois, Urbana, IL (US)

( * ) Notice: Subject to any disclaimer, the term of this patent is extended or adjusted under 35 U.S.C. 154(b) by 229 days.

(21) Appl. No.: 15/363,828

(22) Filed: Nov. 29, 2016

(65) Prior Publication Data
US 2017/0073381 A1 Mar. 16, 2017

Related U.S. Application Data

(63) Continuation-in-part of application No. PCT/US2015/033221, filed on May 29, 2015.

(60) Provisional application No. 62/004,863, filed on May 29, 2014, provisional application No. 62/331,784, filed on May 4, 2016, provisional application No. 62/362,923, filed on Jul. 15, 2016.

(51) Int. Cl.
*C12N 15/67* (2006.01)
*C12P 21/02* (2006.01)

(52) U.S. Cl.
CPC .............. *C12P 21/02* (2013.01); *C12N 15/67* (2013.01)

(58) Field of Classification Search
None
See application file for complete search history.

(56) References Cited

U.S. PATENT DOCUMENTS

| 6,358,713 B1 | 3/2002 | Green et al. |
| 2012/0171720 A1 | 7/2012 | Church et al. |

OTHER PUBLICATIONS

Khaitovich, et al., "Reconstitution of functionally active Thermus aquaticus large ribosomal subunits with in vitro-transcribed rRNA", Biochemistry, Feb. 1999, vol. 38, No. 6, pp. 1780-1788.
Kitahara, et al., "The ordered transcription of RNA domains is not essential for ribosome biogenesis in *Escherichia coli*", Mol Cell, Jun. 2009, vol. 34, No. 6, pp. 760-766.
(Continued)

*Primary Examiner* — Nancy A Treptow
(74) *Attorney, Agent, or Firm* — Quarles & Brady LLP; M. Scott McBride

(57) ABSTRACT

An engineered ribosome that includes a tethered subunit arrangement is disclosed, in which the engineered ribosome supports translation of a sequence defined polymer. Methods for making and using the engineered ribosome are also disclosed, including a method for preparing a sequence defined polymer using the engineered ribosome and a method for preparing a sequence defined polymer using the engineered ribosome in a two-protein translation system. The engineered ribosomes may be utilized in methods for incorporating unnatural amino acids into a sequence defined polymer. Also disclosed are optimized polynucleotide sequences for use as tethers and Shine-Dalgarno/anti-Shine-Dalgarno sequences.

24 Claims, 31 Drawing Sheets
Specification includes a Sequence Listing.

(56) References Cited

OTHER PUBLICATIONS

Tapprich, et al., "Involvement of bases 787-795 of *Escherichia coli* 16S ribosomal RNA in ribosomal subunit association", Proc Natl Acad Sci USA, Feb. 1986, vol. 83, No. 3, pp. 556-560.
International Search Report for PCT/US2015/033221 dated Oct. 16, 2015.
Written Opinion for PCT/US2015/033221 dated Oct. 16, 2015.

A
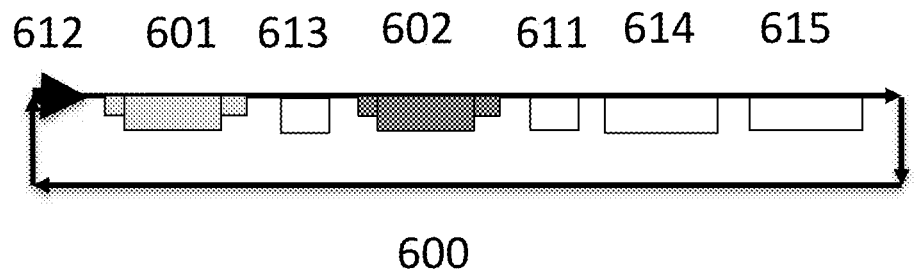
600
B
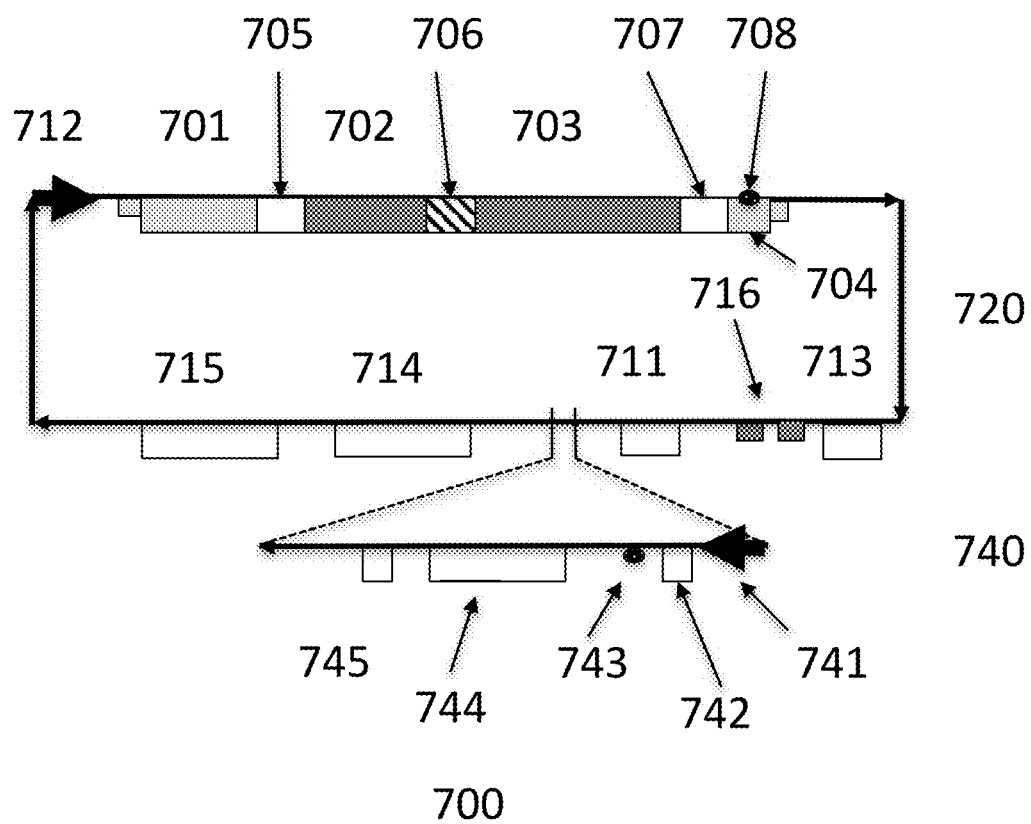
700
FIGURE 4A-B

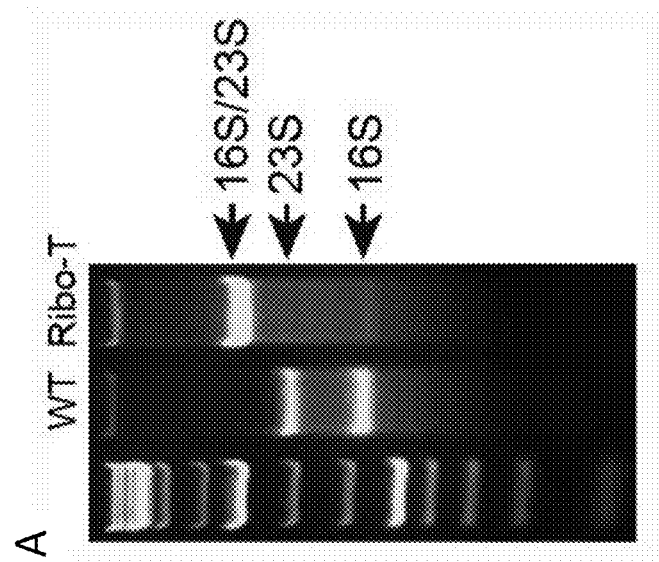
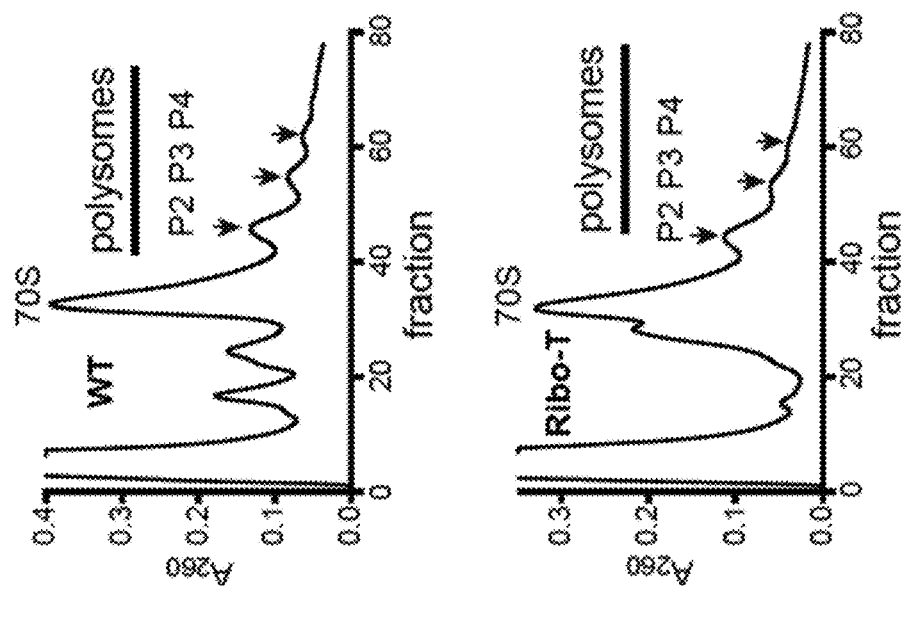
FIGURE 5A-C

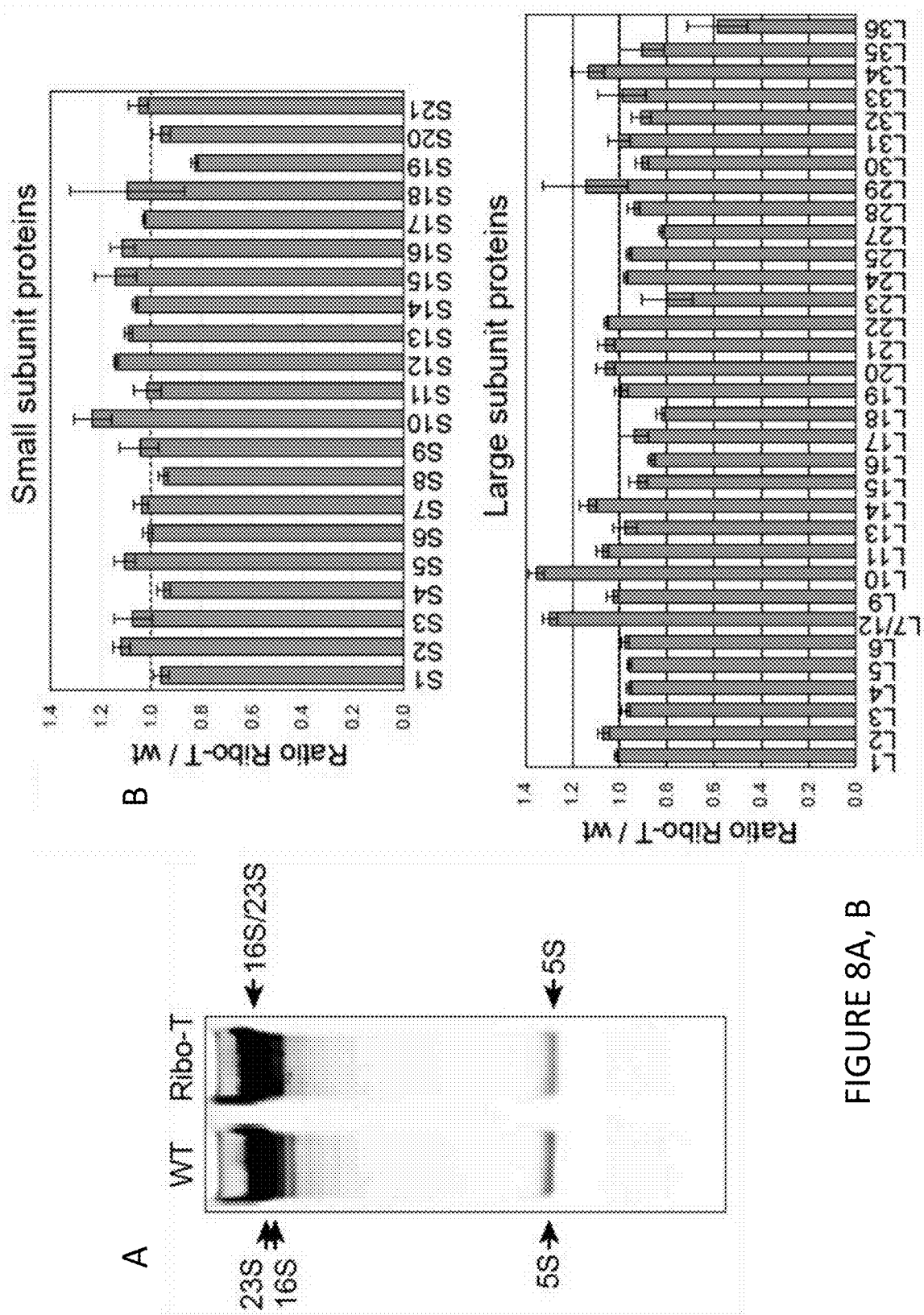
FIGURE 8A, B

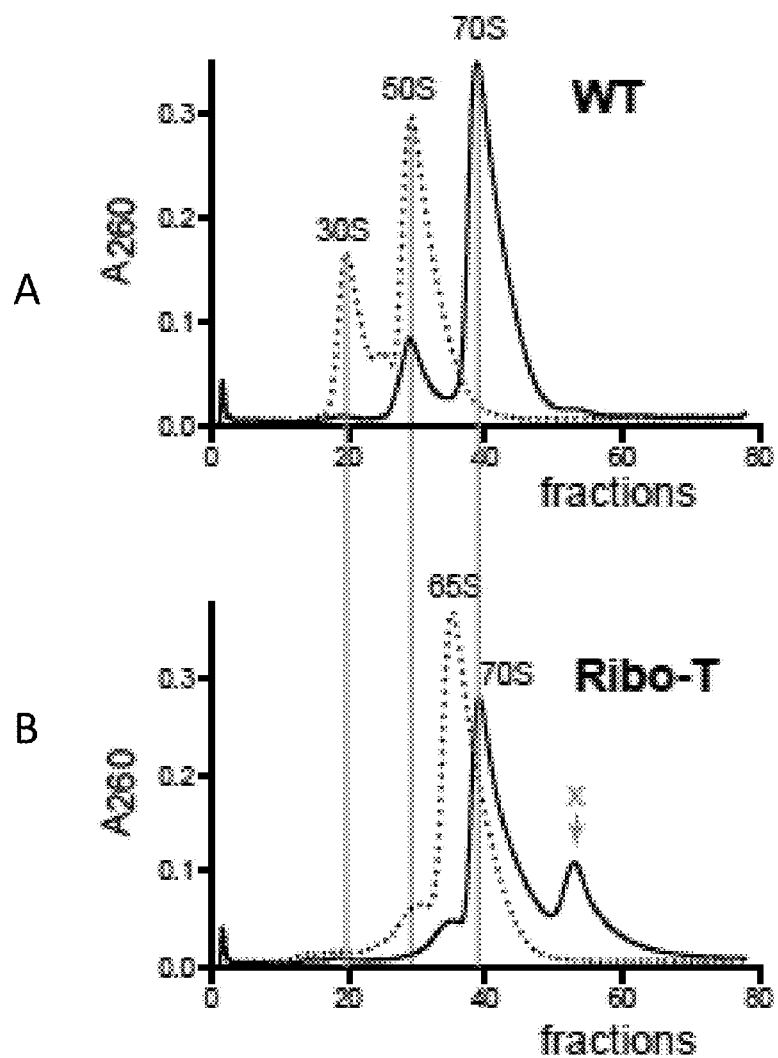
FIGURE 9A-B

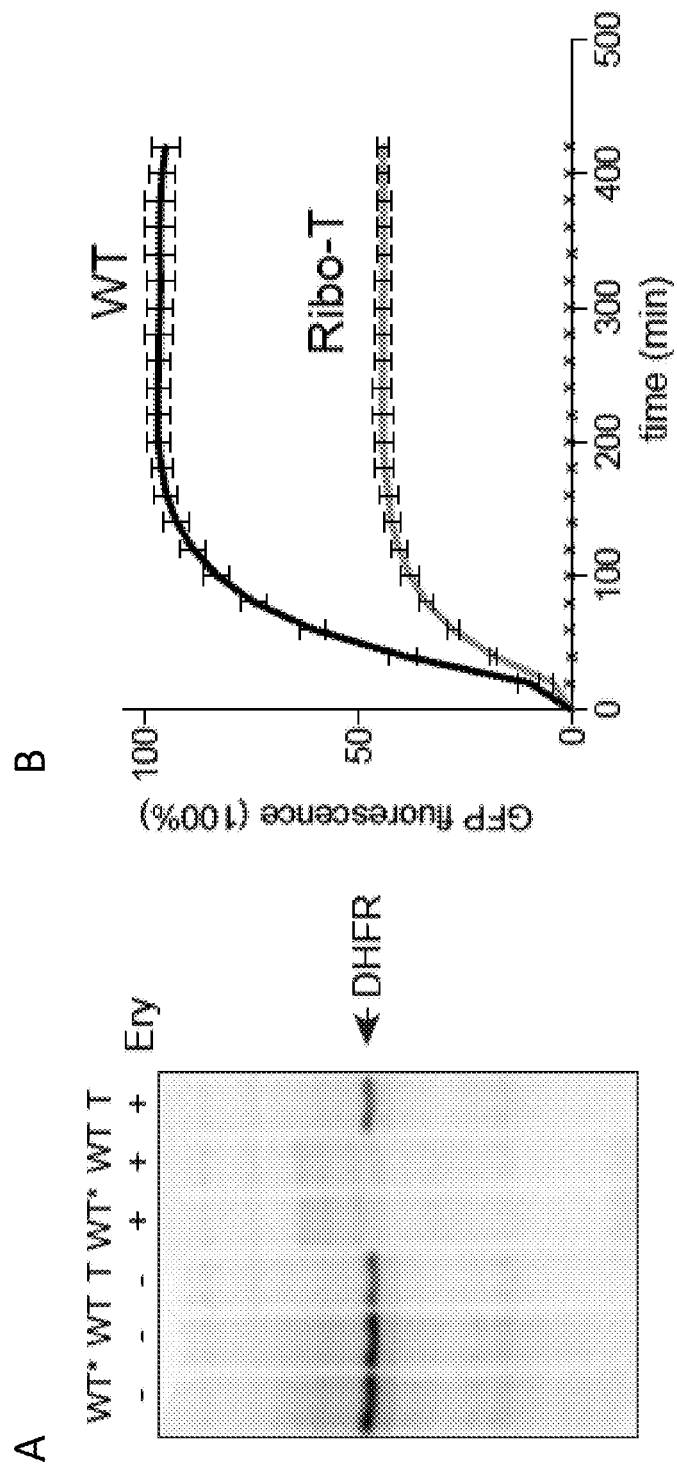
FIGURE 10A-B

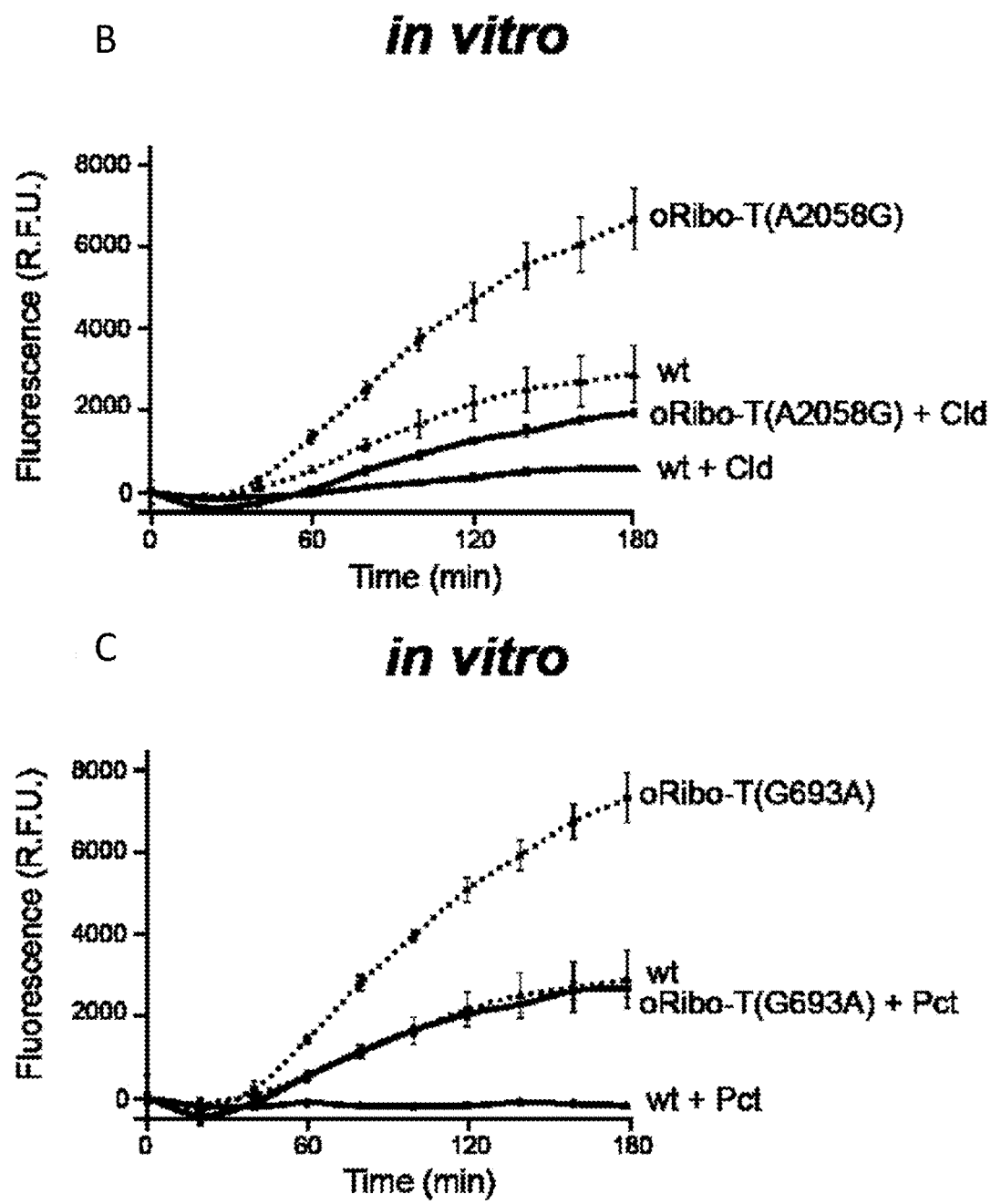
FIGURE 11B, C

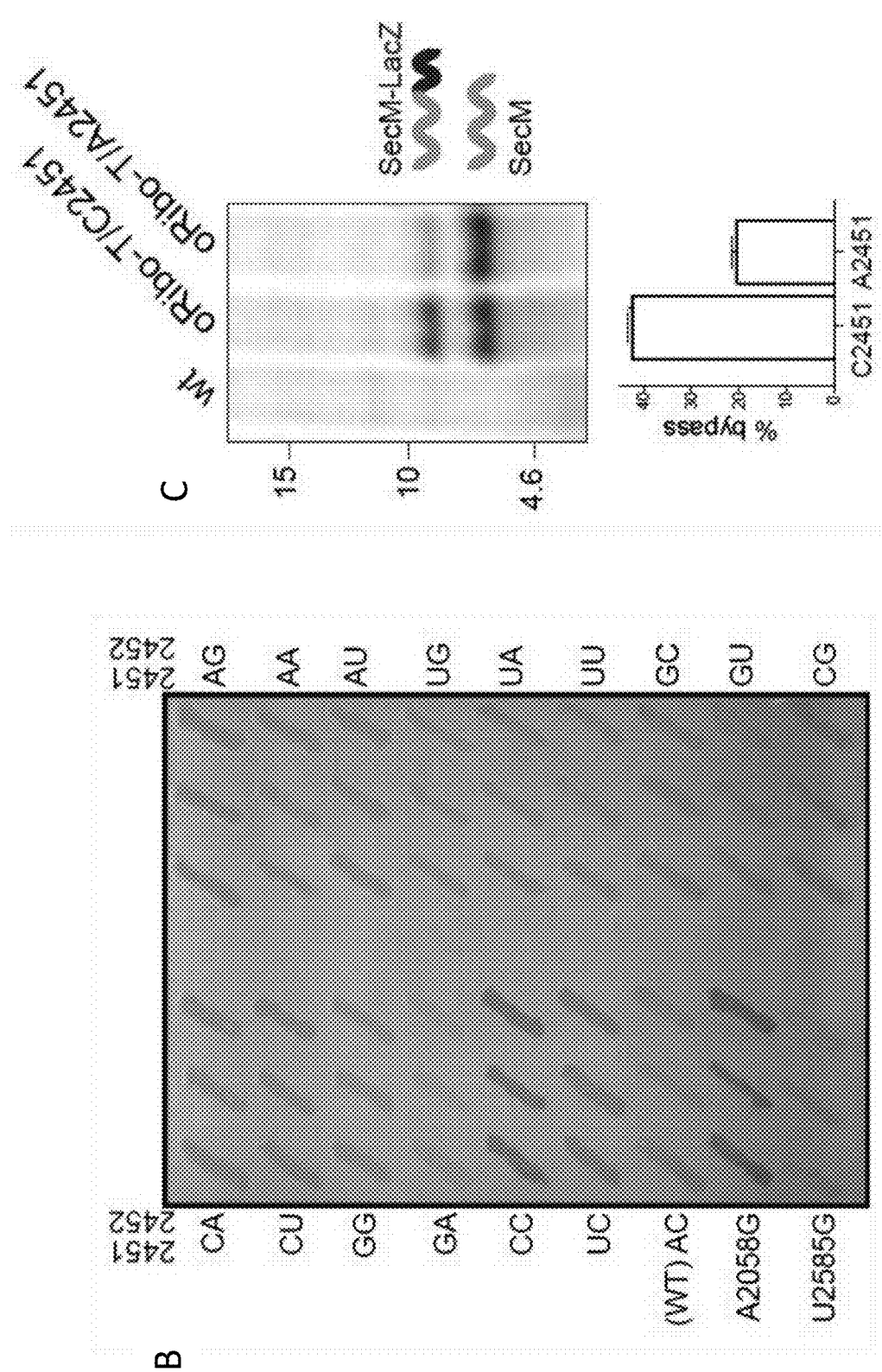
FIGURE 13B, C

Sequences of the fastest growing L4 Library constructs

| Name | Tether 1 | Tether 2 |
|---|---|---|
| L3-FG-Lib-A | CAATGAACAATTGGA (SEQ ID NO:237) | GATAACTAGT (SEQ ID NO:238) |
| L3-FG-Lib-AA | --- | GATAACTAGT (SEQ ID NO:238) |
| L3-FG-Lib-AB | CAATGAACAATTGGA (SEQ ID NO:237) | GATAACTAGT (SEQ ID NO:238) |
| L3-FG-Lib-AC | CAATGAACAATTGGA (SEQ ID NO:237) | GATACCTAGT (SEQ ID NO:256) |
| L3-FG-Lib-AD | --- | GATAACTAGT (SEQ ID NO:238) |
| L3-FG-Lib-B | TGTTAGGCATTGACA (SEQ ID NO:252) | --- |
| L3-FG-Lib-C | CAATGAACAATTGGA (SEQ ID NO:237) | --- |
| L3-FG-Lib-E | CAATGAACAATTGGA (SEQ ID NO:237) | GATAACTAGT (SEQ ID NO:238) |
| L3-FG-Lib-F | AATAATGAATCGTAA (SEQ ID NO:253) | GAACCTAGAC (SEQ ID NO:257) |
| L3-FG-Lib-G | CAATGAACAATTGGA (SEQ ID NO:237) | GATAACTAGT (SEQ ID NO:238) |
| L3-FG-Lib-H | CAATGAACAATTGGA (SEQ ID NO:237) | GATAACTAGT (SEQ ID NO:238) |
| L3-FG-Lib-I | CAATGAAAAATTGGA (SEQ ID NO:254) | GATAACTAGT (SEQ ID NO:238) |
| L3-FG-Lib-J | CAATGAACAATTGGA (SEQ ID NO:237) | --- |
| L3-FG-Lib-K | --- | --- |
| L3-FG-Lib-L | CAATGAACAATTGGA (SEQ ID NO:237) | GATAACTAGT (SEQ ID NO:238) |
| L3-FG-Lib-M | CATGCGGAATTTTAA (SEQ ID NO:255) | --- |
| L3-FG-Lib-N | CAATGAACAATTGGA (SEQ ID NO:237) | GATAACTAGT (SEQ ID NO:238) |
| L3-FG-Lib-O | CAATGAACAATTGGA (SEQ ID NO:237) | GATAACTAGT (SEQ ID NO:238) |
| L3-FG-Lib-X | CAATGAACAATTGGA (SEQ ID NO:237) | --- |
| L3-FG-Lib-Y | --- | GATAACTAGT (SEQ ID NO:238) |
| L3-FG-Lib-Z | CAATGAACAATTGGA (SEQ ID NO:237) | GATAACTAGT (SEQ ID NO:238) |

FIGURE 17

RIBOSOMES WITH TETHERED SUBUNITS

CROSS-REFERENCE TO RELATED PATENT APPLICATIONS

The present application is a Continuation-in-Part (OP) of International Application No. PCT/US2015/033221, filed on May 29, 2015, and published as International Publication No. WO 2015/184283 A1, on Dec. 3, 2015, which International Application claims the benefit of priority under 35 U.S.C. § 119(e), to U.S. Provisional Application No. 62/004,863, filed on May 29, 2014, the contents of which applications are incorporated herein by reference in their entireties. The present application claims the benefit of priority under 35 U.S.C. § 119(e), to U.S. Provisional Application No. 62/331,784, filed on May 4, 2016 and to U.S. Provisional Application No. 62/362,923, filed on Jul. 15, 2016, the contents of which applications are incorporated herein by reference in their entireties.

STATEMENT REGARDING FEDERALLY SPONSORED RESEARCH OR DEVELOPMENT

This invention was made with government support under N66001-12-C-4211, (Subcontract C13K11518 (K00184) Yale University to Northwestern University) awarded by the Space and Naval Warfare Systems Center-Pacific (DARPA). The government has certain rights in the invention.

FIELD

This invention pertains to engineered polynucleotides, engineered ribosomes comprising the engineered polynucleotides, and methods of making and using the engineered polynucleotides and engineered ribosomes. The engineered ribosomes may be utilized to prepare a sequence defined polymers in cells.

BACKGROUND

The ribosome is a ribonucleoprotein machine responsible for protein synthesis. In all kingdoms of life it is composed of two subunits, each built on its own ribosomal RNA (rRNA) scaffold. The independent but coordinated functions of the subunits, including their ability to associate at initiation, rotate during elongation, and dissociate after protein release, are an established paradigm of protein synthesis. Furthermore, the bipartite nature of the ribosome is presumed essential for biogenesis since dedicated assembly factors keep immature ribosomal subunits apart and prevent them from translation initiation [Karbstein 2013]. Free exchange of the subunits limits the development of specialized orthogonal genetic systems that could be engineered or evolved for novel functions without interfering with native translation.

The ribosome is an extraordinary complex machine. This large particle, in which RNA is the main structural and functional component, is invariably comprised of two subunits that coordinate distinct but complementary functions: the small subunit decodes the mRNA, while the large subunit catalyzes peptide-bond formation and provides the exit tunnel for the polypeptide. The association of the subunits is tightly regulated throughout the cycle of translation. First, several assembly factors prevent the two subunits from associating during maturation of the ribonucleoproteins. Later on, the initiation of translation is also strictly controlled such that small subunit is involved in the first steps of initiation, while the large subunit is kept apart. Initiation factors, mRNA and fMet-tRNA$^{fMet}$ sequentially join the small subunit to form a pre-initiation complex before recruiting the large subunit. During elongation, the subunits ratchet relative to each other with an angle of about 6 degrees. Upon termination, the newly synthesized protein is released from the ribosome and the subunits dissociate during an active process called ribosome recycling to prepare for subsequent rounds of translation. Thus, the requirement for programmed subunit association and dissociation at specific stages of translation is considered a prerequisite for protein synthesis and likely explains why the ribosome has been maintained as two subunits during the course of evolution. Although initiation at the leaderless mRNAs was suggested to be carried out by the 70S ribosome with pre-associated subunits, no experimental evidence exists showing that the full cycle of protein synthesis could be accomplished by the ribosome with inseparable subunits.

The random exchange of ribosomal subunits between recurrent acts of protein biosynthesis presents an obstacle for making fully orthogonal ribosomes, a task with important implications for both fundamental science and bioengineering. Previously, it was possible to redirect a subpopulation of the small ribosomal subunits from translating indigenous mRNA to translation of a specific mRNA by placing an alternative Shine-Dalgarno (SD) sequence in a reporter mRNA and introducing the complementary changes in the anti-SD region in 16S rRNA [Hui 1987; Rackham 2005], which enabled selection of mutant 30S subunits with new decoding properties [Wang 2007]. However, because large subunits freely exchange between native and orthogonal small subunits, creating a fully orthogonal ribosome has been impossible thereby limiting the engineering of the 50S subunit, including the peptidyl transferase center (PTC) and the nascent peptide exit tunnel, for specialized new properties.

The engineering of a tethered ribosome, in which the subunits are linked to each other, opens new venues preparing orthogonal translation systems, evolving the ribosome for the incorporation of unnatural amino acids in synthetic biology, and molecularly characterizing mutations of functionally critical nucleotides which are often associated with lethal phenotype. Previously, we and others disclosed tethered ribosomes and methods of making and using tethered ribosomes. (See International Published Application WO 2015/184283, "Tethered Ribosomes and Methods of Making and Using Thereof," and Orelle et al., "Protein synthesis by ribosomes with tethered subunits," Nature, 6 Aug. 2015, Vol. 524, page 119). Here, with disclose improvements to ribosomes with tethered subunits including ribosomes having tether sequences with improved functionality and orthogonal Shine-Dalgarno/anti Shine-Dalgarno pairs for improved orthogonal performance.

SUMMARY

Disclosed herein are engineered ribosomes, the engineered ribosomes comprising a small subunit, a large subunit, and a linking moiety, wherein the linking moiety tethers the small subunit with the large subunit and wherein the engineered ribosome is capable of supporting translation of a sequence defined polymer.

In certain embodiments, the small subunit comprises rRNA, the large subunit comprises rRNA, and the linking moiety tethers the rRNA of the small subunit with the rRNA of the large subunit. In certain embodiments, the large subunit comprises a permuted variant of a 23S rRNA. In certain embodiments, the small subunit comprises a permuted variant of a 16S rRNA. As such, in certain embodiments, the engineered ribosomes comprise a fusion of: (a) 16S rRNA, a permuted variant thereof, or fragments thereof; and (b) 23S rRNA, a permuted variant thereof, or fragments thereof. In certain embodiments, the small subunit comprises a modified anti-Shine-Dalgarno sequence to permit translation of templates having a complementary Shine-Dalgarno sequence difference from an endogenous cellular mRNAs.

In certain embodiments, the linking moiety covalently bonds a helix of the large subunit to a helix of the small subunit. In certain embodiments, the linking moiety covalently bonds helix 10, helix 38, helix 42, helix 54, helix 58, helix 63, helix 78, or helix 101 of the permuted variant of the 23S rRNA. In certain embodiments, the linking moiety covalently bonds helix 11, helix 26, helix 33, or helix 44 of the permuted variant of the 16S rRNA.

In certain embodiments, the large subunit comprises a L1 polynucleotide domain, a L2 polynucleotide domain, and a C polynucleotide domain, wherein the L1 domain is followed, in order, by the C domain and the L2 domain, from 5' to 3'. In certain embodiments, the polynucleotide consisting essentially of the L2 domain followed by the L1 domain, from 5' to 3', is substantially identical to 23S rRNA. In certain embodiments, the polynucleotide consisting essentially of the L2 domain followed by the L1 domain, from 5' to 3', is at least 95% identical to a 23S rRNA. In certain embodiments, the C domain comprises a polynucleotide having a length ranging from 1-200 nucleotides. In certain embodiments, the C domain comprises a GAGA polynucleotide.

In certain embodiments, the small subunit comprises a S1 polynucleotide domain and a S2 polynucleotide domain, wherein the S1 domain is followed, in order, by the S2 domain, from 5' to 3'. In certain embodiments, the polynucleotide consisting essentially of the S1 domain followed by the S2 domain, from 5' to 3', is substantially identical to a 16S rRNA. In certain embodiments, the polynucleotide consisting essentially of the S1 domain followed by the S2 domain, from 5' to 3', is at least 95% identical to a 16S rRNA.

In certain embodiments, the linking moiety comprises a T1 polynucleotide domain and a T2 polynucleotide domain. In certain embodiments, the T1 domain links the S1 domain and the L1 domain and wherein the S1 domain is followed, in order, by the T1 domain and the L1 domain, from 5' to 3'. In certain embodiments, the T1 domain comprises a polynucleotide having a length ranging from 5 to 200 nucleotides. In certain embodiments, the T1 domain comprises a polynucleotide having a length ranging from 7 to 40 nucleotides. In certain embodiments, the T1 domain comprises a polyadenine polynucleotide. In certain embodiments, the T1 domain comprises a polyadenine polynucleotide having a length of 7 to 12 adenine nucleotides. In certain embodiments, the T2 domain links the S2 domain and the L2 domain and wherein the L2 domain is followed, in order, by the T2 domain and the S2 domain, from 5' to 3'. In certain embodiments, the T2 domain comprises a polynucleotide having a length ranging from 5 to 200 nucleotides. In certain embodiments, the T2 domain comprises a polynucleotide having a length ranging from 7 to 20 nucleotides. In certain embodiments, the T2 domain comprises a polyadenine polynucleotide. In certain embodiments, the T2 domain comprises a polyadenine polynucleotide having a length of 7 to 12 adenine nucleotides.

In certain embodiments, the engineered ribosome comprises the S1 domain followed, in order, by the T1 domain, the L1 domain, the C domain, the L2 domain, the T2 domain, and the S2 domain, from 5' to 3'. In certain embodiments, the engineered ribosome comprises a polynucleotide consisting essentially of the S1 domain is followed, in order, by the T1 domain, the L1 domain, the C domain, the L2 domain, the T2 domain, and the S2 domain, from 5' to 3'.

In certain embodiments, the engineered ribosome comprises a mutation, such as a change-of-function mutation in a peptidyl transferase center, a change-of-function mutation in the exit tunnel of the engineered ribosome, a change-of-function to the decoding center of the ribosome, a change-of-function mutation to an interaction site with elongation factors, a change-of-function mutation in tRNA binding sites, a change-of-function mutation in chaperone binding sites, a change-of-function mutation in nascent chain modifying enzyme binding sites, a change-of-function mutation in the GTPase center, and any combination thereof. In certain embodiments, the mutation is a change-of-function mutation. In certain embodiments, the change-of-function mutation is a gain-of-function mutation. In certain embodiments, the gain-of-function mutation is in a peptidyl transferase center. In certain embodiments, the gain-of-function mutation is in an A-site of the peptidyl transferase center. In certain embodiments, the gain-of-function mutation is in the exit tunnel of the engineered ribosome. In certain embodiments, the change-of-function mutation is in other sites of the ribosome. In certain embodiments, the engineered ribosome has an antibiotic resistance mutation.

Disclosed herein are polynucleotides, the polynucleotides encoding the rRNA of the engineered ribosome. In certain embodiments, the polynucleotide is a vector. In certain embodiments, the polynucleotide further comprises a gene to be expressed by the engineered ribosome. In certain embodiments, the gene is a reporter gene. In certain embodiments, the reporter gene is a green fluorescent protein gene. In certain embodiments, the engineered ribosome comprises a modified anti-Shine-Dalgarno sequence and the gene comprises a complementary or cognate modified Shine-Dalgarno sequence to the engineered ribosome. In certain embodiments, the gene comprises a codon and the codon encodes for an unnatural amino acid.

Disclosed herein are methods for preparing an engineered ribosome, the method comprising expressing a polynucleotide encoding the rRNA of the engineered ribosome. In certain embodiments, method further comprising selecting a mutant. In certain embodiments, the selection step comprises a negative selection step, a positive selection step, or both a negative and a positive selection step.

Disclosed here are cells, the cells comprising (i) a polynucleotide polynucleotides encoding the rRNA of the engineered ribosome, (ii) the engineered ribosome, or both (i) and (ii).

In another aspect of the invention, disclosed herein are cells, the cells comprising a first protein translation mechanism and a second protein translation mechanism, wherein the first protein translation mechanism comprises a ribosome, wherein the ribosome lacks a linking moiety between the large subunit and the small subunit and wherein the second protein translation mechanism comprises the engineered ribosome.

Disclosed herein are methods for preparing a sequence-defined polymer, the methods comprising (a) providing the engineered ribosome and (b) providing an mRNA or DNA template encoding the sequence-defined polymer, and preparing the sequence-defined polymer using the engineered ribosome and the mRNA or DNA template encoding the sequence-defined polymer. In certain embodiments, the sequence-defined polymer is prepared in vitro. In certain embodiments, the method further comprises providing (c) a ribosome-depleted cellular extract or purified translation system and using the ribosome-depleted cellular extract or purified translation system to preparing the sequence-defined polymer. In certain embodiments, the ribosome-depleted cellular extract comprises an 5150 extract prepared from mid- to late-exponential growth phase cell cultures or cultures having an O.D.600~3.0 at time of harvest.

In certain embodiments, the sequence defined polymer is prepared in vivo. In certain embodiments, the sequence defined polymer is prepared in the cell of any of claim 45 or 46. In certain embodiments, the mRNA or DNA encodes a modified Shine-Dalgarno sequence and the engineered ribosome comprises a modified anti-Shine-Dalgarno sequence complementary or cognate to the modified Shine-Dalgarno sequence.

In certain embodiments, the sequence-defined polymer comprises an amino acid. In certain embodiments, the amino acid is a natural amino acid. In certain embodiments, the amino acid is an unnatural amino acid.

BRIEF DESCRIPTION OF THE DRAWINGS

FIG. 4A illustrates a plasmid having a gene encoding for rRNA.

FIG. 4B illustrates a plasmid having a gene encoding for the rRNA of a tethered ribosome.

FIG. 5A shows agarose gel electrophoresis of total RNA prepared from SQ171fg cells expressing wild-type ribosomes or Ribo-T. (See Orelle, C., et al. *Nature*, 2015. 524(7563): p. 119-124).

FIG. 5B shows a sucrose gradient fractionation of polysomes prepared from cells expressing wild-type ribosomes.

FIG. 5C shows a sucrose gradient fractionation of polysomes prepared from cells expressing Ribo-T ribosomes.

FIG. 8A shows polyacrylamide gel electrophoresis of rRNA prepared from the isolated wild-type ribosomes or a tethered ribosome.

FIG. 8B shows the relative abundance of small and large subunit proteins in Ribo-T in comparison with wild-type ribosome as determined by mass-spectrometry.

FIG. 9A shows a sucrose gradient analysis of wild-type ribosomes at high $Mg^{2+}$ conditions (solid line) and low $Mg^{2+}$ subunit dissociation conditions (dotted line).

FIG. 9B shows a sucrose gradient analysis of tethered ribosomes at high $Mg^{2+}$ conditions (solid line) and low $Mg^{2+}$ subunit dissociation conditions (dotted line). The "X" denotes possible Ribo-T dimers forming in high $Mg^{2+}$ conditions.

FIG. 10A shows SDS gel electrophoresis analysis of the DHFR protein synthesized in the A ribosome PURExpress system supplemented with purified wt ribosomes (WT) or Ribo-T (T).

FIG. 10B shows the time course of expression of the sf-GFP protein in the A ribosome PURExpress system supplemented with purified wild-type ribosomes or a tethered ribosomes.

FIG. 11B shows in vitro translation of the orthogonal sf-gfp reporter by wild-type ribosomes and tethered ribosomes carrying A2058G mutation in the large subunit.

FIG. 11C shows in vitro translation of the orthogonal sf-gfp reporter by wild-type ribosomes and tethered ribosomes carrying G693A mutation in the small subunit.

FIG. 13B shows *E. coli* cells transformed with a secM-lacZα gene with different nucleotide combinations at the 2451 and 2452 positions.

FIG. 13C shows enhancement of the bypass of the SecM stalling sequence.

DETAILED DESCRIPTION

Ribosomes with tethered and thus inseparable subunits ("Ribo-T") that are capable of successfully carrying out protein synthesis are disclosed. Ribo-T may be prepared by engineering a ribosome comprising a small subunit, a large subunit, and a linking moiety that tethers the small subunit with the large subunit. The engineered ribosome may comprise a hybrid rRNA comprising a small subunit rRNA sequence, a large subunit rRNA sequence, and RNA linkers that may covalently link the small subunit rRNA sequence and the large subunit rRNA sequence into a single entity. The engineered ribosome may be prepared by expressing a polynucleotide encoding the rRNA of the engineered ribosome. The engineered ribosome may also be evolved by positively or negatively selecting mutations. Ribo-T is not only functional in vitro, but is able to support cell growth even in the absence of wild-type ("wt") ribosomes. As a result, Ribo-T has many uses. For example, Ribo-T may be used to prepare sequence-defined polymers, such as naturally occurring proteins or unnaturally occurring amino-acid polymers; create fully orthogonal ribosome-mRNA systems in vitro or in vivo; explore poorly understood functions of the ribosome; and engineer ribosomes with new functions.

Tethered Ribosome

The engineered ribosome comprises a small subunit, a large subunit, and a linking moiety, wherein the linking moiety tethers the small subunit with the large subunit. The engineered ribosome is capable of supporting translation of a sequence-defined polymer.

Figure 1:
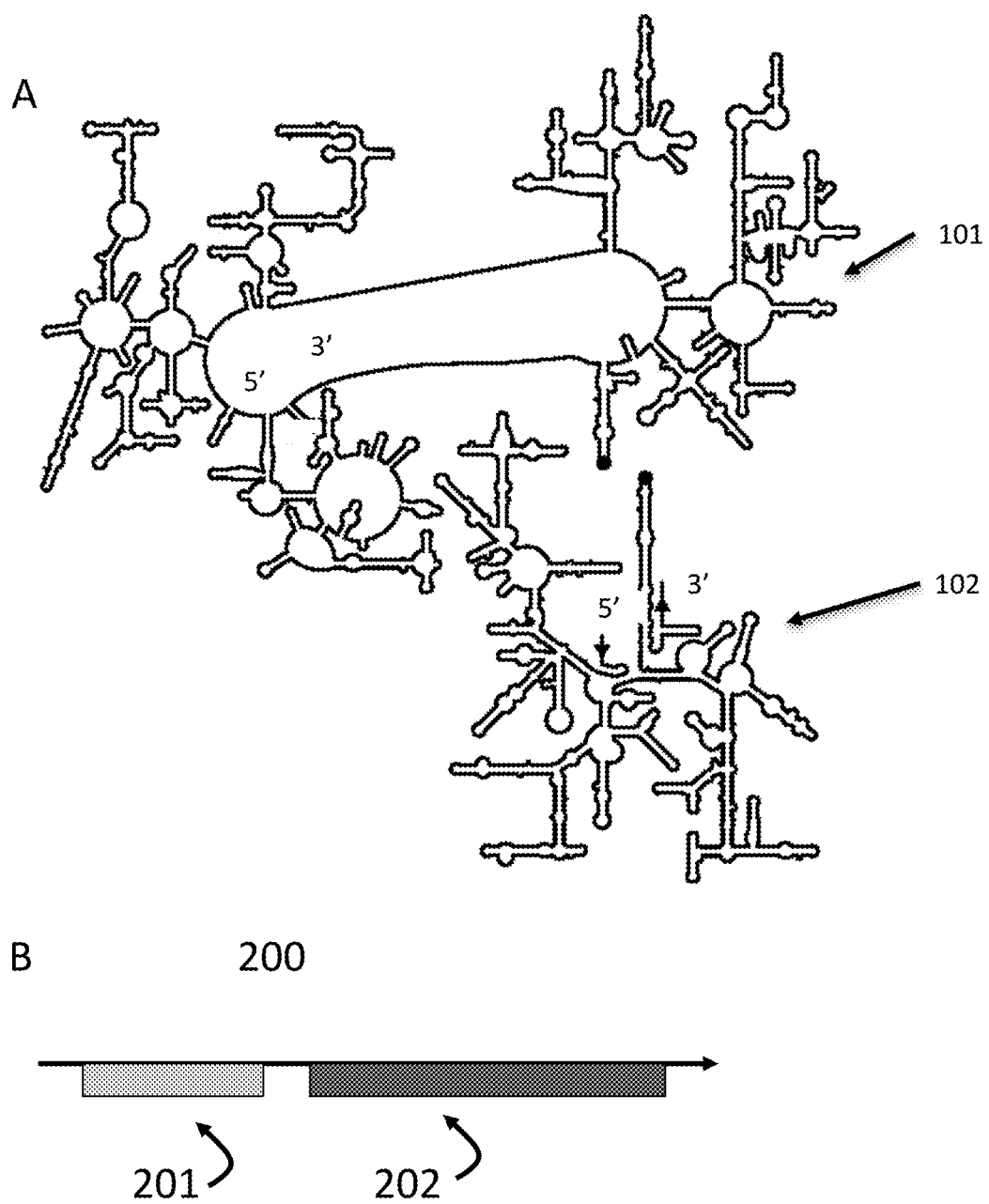
FIG. 1A illustrates the secondary structure of a large subunit rRNA and a small subunit rRNA.
FIG. 1B illustrates a gene encoding a large subunit rRNA and a small subunit rRNA.

In contrast to a naturally occurring ribosome, the engineered ribosome has a large and a small subunit that are not separable. FIG. 1 depicts a portion of a wild-type ribosome having a small subunit and a large subunit that are separable. FIG. 1A illustrates the secondary structure of a large subunit 101 and a small subunit rRNA 102 that together form a portion of a functional ribosome. FIG. 1B illustrates an rRNA gene 200 comprising the operon encoding the large subunit rRNA 202 and the operon encoding the small subunit rRNA 201. In the wild-type rRNA, the large and small subunit rRNAs are excised from the primary transcript and processed to mature individual subunits.

Figure 2:
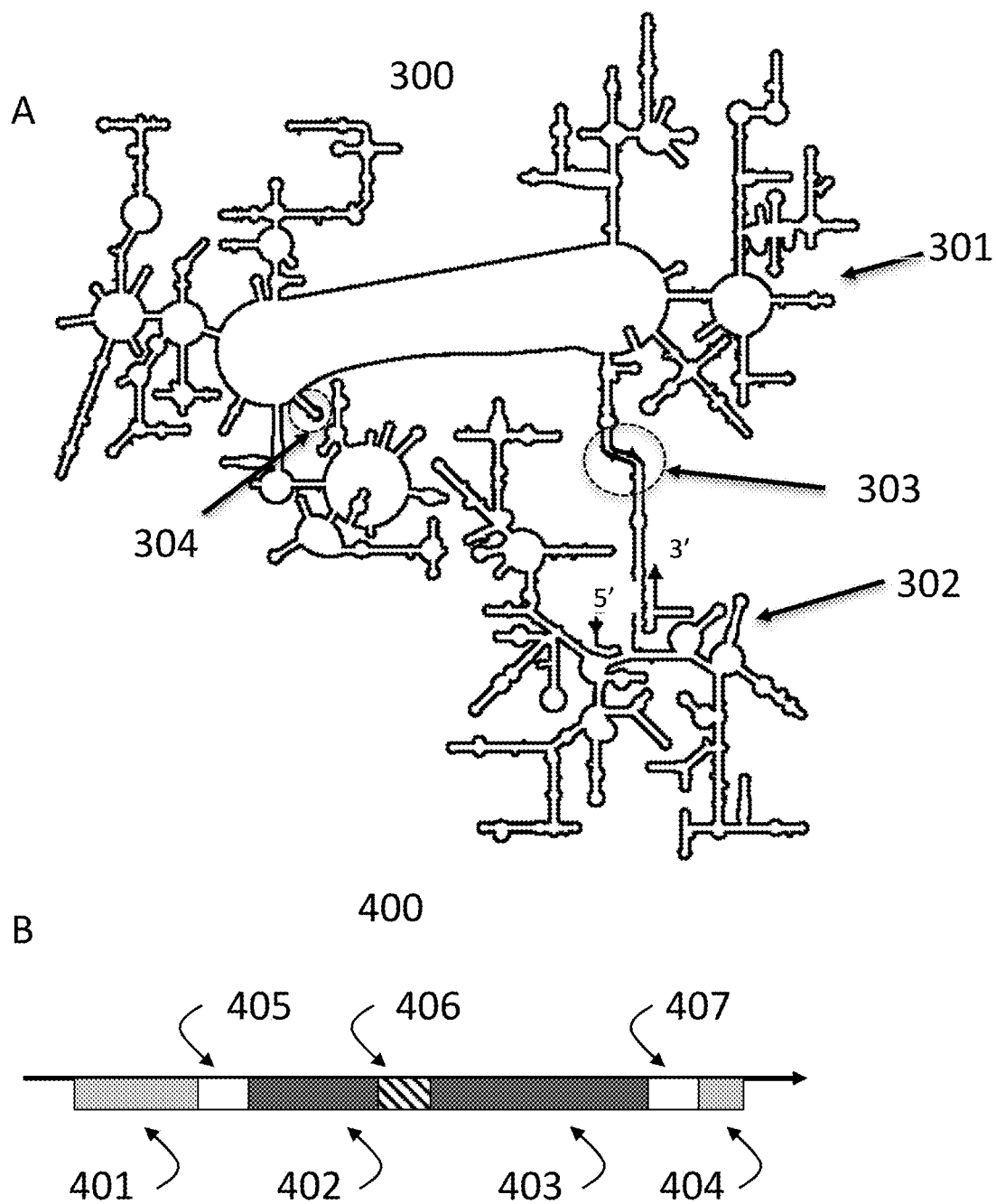
FIG. 2A illustrates a tethered ribosome having a large subunit, a small subunit, and a linking moiety.
FIG. 2B illustrates a gene encoding the tethered ribosome of FIG. 2A.

An embodiment of the engineered tethered ribosome is illustrated in FIG. 2. FIG. 2A illustrates the secondary structure of a portion of rRNA of the engineered ribosome 300. The engineered ribosome comprises a large subunit 301, a small subunit 302, and a linking moiety 303 that tethers the small subunit 302 with the large subunit 301. In the present example, the linking moiety 303 tethers the rRNA of the small subunit 302 with the rRNA of the large subunit 301. The engineered ribosome may also comprise a connector 304, that closes the ends of a native large subunit rRNA. FIG. 2B illustrates an example of an rRNA gene 400 and the operon encoding to the engineered ribosome 300.

Large Subunit

The large subunit 301 comprises a catalytic subunit capable of joining amino acids to form a polypeptide chain. The large subunit 301 may comprise a first large subunit domain ("L1 polynucleotide domain" or "L1 domain"), a second large subunit domain ("L2 polynucleotide domain" or "L2 domain"), and a connector domain ("C polynucleotide domain" or "C domain") 304, wherein the L1 domain is followed, in order, by the C domain and the L2 domain, from 5' to 3'.

FIG. 2B illustrates an example of an rRNA gene 400 that encodes the engineered ribosome 300, and provides an alternative representation for understanding the engineered ribosome. The encoding polynucleotide 400 may comprise difference sequences that encode for the various domains of the engineered ribosome 300. As illustrated in FIG. 2B, the polynucleotide encoding the large subunit rRNA 301 comprises the polynucleotide encoding the L1 domain 402, the polynucleotide encoding the C domain 406, and the polynucleotide encoding the L2 domain 403.

The large subunit rRNA 301 may be a permuted variant of a separable large subunit rRNA. In certain embodiments, the permuted variant is a circularly permuted variant of a separable large subunit rRNA. The separable large subunit may be any functional large subunit. In certain embodiments, the separable large subunit may be a 23S rRNA. In certain embodiments, the separable large subunit is a wild-type large subunit rRNA. In specific embodiments, the separable large subunit is a wild-type 23S rRNA.

If the large subunit 301 is a permuted variant of a large subunit rRNA, then the polynucleotide consisting essentially of the L2 domain followed by the L1 domain, from 5' to 3', may be substantially identical to a large subunit rRNA. In certain embodiments, the polynucleotide consisting essentially of the L2 domain followed by the L1 domain, from 5' to 3', is at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the large subunit rRNA.

In certain embodiments where the large subunit 301 is a permuted variant of a separable large subunit rRNA, the large subunit 301 may further comprise a C domain 304 that connects the native 5' and 3' ends of the separable large subunit rRNA. The C domain may comprise a polynucleotide having a length ranging from 1-200 nucleotides. In certain embodiments, the C domain 304 comprises a polynucleotide having a length ranging from 1-150 nucleotides 1-100 nucleotides, 1-90 nucleotides, from 1-80 nucleotides, 1-70 nucleotides, 1-60 nucleotides, 1-50 nucleotides, 1-40 nucleotides, 1-30 nucleotides, 1-20 nucleotides, 1-10 nucleotides, 1-9 nucleotides, 1-8 nucleotides, 1-7 nucleotides, 1-6 nucleotides, 1-5 nucleotides, 1-4 nucleotides, 1-3 nucleotides, or 1-2 nucleotides. In certain embodiments, the C domain comprises a GAGA polynucleotide.

Small Subunit

The small subunit 302 is capable of binding mRNA. The small subunit 302 comprises a first small subunit domain ("S1 polynucleotide domain" or "S1 domain") and a second small subunit domain ("S2 polynucleotide domain" or "S2 domain"), wherein the 51 domain is followed, in order, by S2 domain, from 5' to 3'. Referring again to FIG. 2B, the polynucleotide encoding the small subunit rRNA 302 comprises the polynucleotide encoding the S1 domain 401 and the polynucleotide encoding the S2 domain 404.

The small subunit rRNA 302 may be a permuted variant of a separable small subunit rRNA. In certain embodiments, the permuted variant is a circularly permuted variant of a separable small subunit rRNA. The separable small subunit may be any functional small subunit. In certain embodiments, the separable small subunit may be a 16S rRNA. In certain embodiments, the separable small subunit is a wild-type small subunit rRNA. In specific embodiments, the separable small subunit is a wild-type 23S rRNA.

If the small subunit 302 is a permuted variant of a small subunit rRNA, then the polynucleotide consisting essentially of the S1 domain followed by the S2 domain, from 5' to 3', may be substantially identical to a small subunit rRNA. In certain embodiments, the polynucleotide consisting essentially of the S1 domain followed by the S2 domain, from 5' to 3', is at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to the small subunit rRNA.

The small subunit may further comprise a modified-anti-Shine-Dalgarno sequence. The modified anti-Shine-Dalgarno sequence allows for translation of templates having a complementary or cognate Shine-Dalgarno sequence different from an endogenous cellular mRNA.

Linking Moiety

Referring again to FIG. 2B, the linking moiety 303 tethers the small subunit 302 with the large subunit 301. In certain embodiments that linking moiety covalently bonds a helix of the large subunit 301 to a helix of the small subunit 302.

The linking moiety may also comprise a first tether domain ("T1 polynucleotide domain" or "T1 domain") and a second tether domain ("T2 polynucleotide domain" or "T2 domain"). Referring again to FIG. 2B, the polynucleotide encoding the linking moiety 303 comprises the polynucleotide encoding the T1 domain 405 and the polynucleotide encoding the T2 domain 407.

The T1 domain links that S1 domain and the L1 domain, wherein the S1 domain is followed, in order, by the T1 domain and the L1 domain, from 5' to 3'. The T1 domain may comprise a polynucleotide having a length ranging from 5-200 nucleotide, 5-150 nucleotides, 5-100 nucleotides, 5-90 nucleotide, 5-80 nucleotides, 5-70 nucleotides, 5-60 nucleotides, 5-50 nucleotides, 5-40 nucleotides, 5-30 nucleotides, or 5-20 nucleotides, including polynucleotides having 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, or 20 nucleotides. In certain embodiments, T1 comprises polyadenine. In certain embodiments, T1 comprises polyuridine. In certain embodiments, T1 comprises an unstructured polynucleotide. In certain embodiments, T1 comprises nucleotides that base-pairs with the T2 domain.

The T2 domain links that L2 domain and the S2 domain, wherein the L2 domain is followed, in order, by the T2 domain and the S2 domain, from 5' to 3'. The T2 domain may comprise a polynucleotide having a length ranging from 5-200 nucleotides, 5-150 nucleotides, 5-100 nucleotides, 5-90 nucleotide, 5-80 nucleotides, 5-70 nucleotides, 5-60 nucleotides, 5-50 nucleotides, 5-40 nucleotides, 5-30 nucleotides, or 5-20 nucleotides, including polynucleotides having 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, or 20 nucleotides. In certain embodiments, T1 comprises polyadenine. In certain embodiments, T2 comprises polyuridine. In certain embodiments, T2 comprises an unstructured polynucleotide. In certain embodiments, T2 comprises nucleotides that base-pairs with the T1 domain.

In embodiments having a T1 domain and a T2 domain, the T1 domain and the T2 domain may have the same number of polynucleotides. In other embodiments, the T1 domain and the T2 domain may have a different number of polynucleotides.

In certain embodiments, the engineered ribosome may comprise a S1 domain followed, in order, by a T1 domain, a L1 domain, a C domain, a L2 domain, a T2 domain, and a S2 domain, from 5' to 3'. In specific embodiments, the engineered ribosome may consist essentially of a S1 domain followed, in order, by a T1 domain, a L1 domain, a C domain, a L2 domain, a T2 domain, and a S2 domain, from 5' to 3'.

Mutations

In certain embodiments, the engineered ribosome may comprise one or more mutations. In specific embodiments the mutation is a change-of-function mutation. A change-of-function mutation may be a gain-of-function mutation or a loss-of-function mutation. A gain-of-function mutation may be any mutation that confers a new function. A loss-of-function mutation may be any mutation that results in the loss of a function possessed by the parent.

In certain embodiments, the change-of-function mutation may be in the peptidyl transferase center of the ribosome. In specific embodiments, the change-of-function mutation may be in an A-site of the peptidyl transferase center. In other embodiments, the change-of-function mutation may be in the exit tunnel of the engineered ribosome.

In certain embodiments, the change-of-function mutation may be in the other functional sites of the ribosome, such as tRNA binding sites, chaperone binding sites, methionine-deformylase binding site, N-terminal peptidase bindings site, elongation factor binding sites, GTPase center and others.

In certain embodiments the change-of-function mutation may be an antibiotic resistance mutation. The antibiotic resistance mutation may be either in the large subunit or the small subunit. In certain embodiments antibiotic resistance mutation may render the engineered ribosome resistant to an aminoglycoside, a tetracycline, a pactamycin, a streptomycin, an edein, or any other antibiotic that targets the small ribosomal subunit. In certain embodiments antibiotic resistance mutation may render the engineered ribosome resistant to a macrolide, a chloramphenicol, a lincosamide, an oxazolidinone, a pleuromutilin, a streptogramin, or any other antibiotic that targets the large ribosomal subunit.

Designing the Tethered Ribosome

A successful chimeric construct that tethers a large subunit and a small subunit must i) properly interact with the ribosomal proteins and biogenesis factors for functional ribosome assembly; ii) avoid ribonuclease degradation; and iii) have a linker(s) sufficiently short to ensure subunit cis-association, yet long enough for minimal inhibition of subunit movement required for translation initiation, elongation, and peptide release. The native ends of the large subunit and the small subunit are unsuitable given the design constraints outlined above. For example, in a native prokaryotic ribosome, for example, the 5' and 3' ends of 16S and 23S rRNA are too far apart (>170 Å) to be connected with a nuclease resistant RNA linker. As a result, alternative designs are needed if functioning engineered ribosome are to be realized.

One approach for designing a tethered ribosome is to permute a large subunit to generate new 5' and 3' termini. In certain embodiments, a circular permutation (CP) approach is employed because the native ends on the large subunit are proximal to each other. Circular permutation can be illustrated in the following scheme:

```
ABCDEFGH
BCDEFGHA
CDEFGHAB
DEFGHABC
EFGHABCD
FGHABCDE
GHABCDEF
HAGCDEFG
```

As such, in circular permutations of a polynucleotide, the sequence of the polynucleotide is maintained in each permutation but each nucleotide is at the end of an individual permutation. Circular permutations or utilized to replace the end of a polynucleotide at a different position while maintaining the secondary structure of the polynucleotide.

Figure 3:
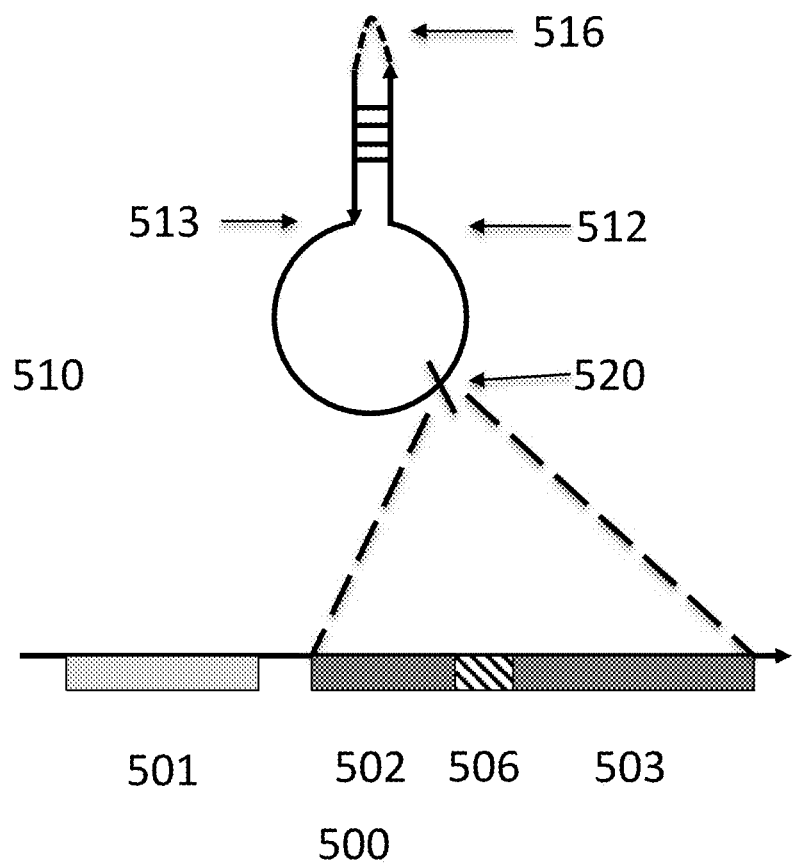
FIG. 3 illustrates the permutation of a ribosome subunit.

The CP approach has been pioneered in vitro by Polacek and coworkers [Erlacher 2005], and a subsequent pilot study showed that three 23S rRNA circularly permuted variants could assemble into a functional subunit in vivo [Kitahara 2009]. This approach is illustrated in FIG. 3. In FIG. 3, a native large subunit ribosome 510 comprises a second large subunit domain (L2 domain) 513 followed by a first large subunit domain (L1 domain), from 5' to 3'. The native ends of a large subunit ribosome 510 (which is a simplified representation of the large subunit rRNA 101 represented in FIG. 1A) are connected through a connector domain (C domain) 511 and new termini are prepared at 512. The permuted subunit prepared by this approach comprises the first large subunit domain (L1 domain), followed, in order, by the connector domain (C domain) and the second large subunit domain (L2 domain), from 5' to 3'. FIG. 3 also illustrates a portion of a gene 500 that encodes for the small subunit 501 and the new permuted large subunit comprising the L1 domain 502, followed, in order, by the C domain 506 and the L2 domain 503, from 5' to 3'.

Continuing the approach outlined above, new termini for the small subunit need to be prepared so that the new termini for the small unit can be joined with the new termini of the large subunit by the linking moiety, as shown in FIGS. 2A, B.

The approach outlined above can be used to generate collections of circularly permuted mutants with new termini. The new termini may be prepared at any location in the native subunit. Although some new termini result in permuted mutants may not be viable, the process disclosed herein is capable of generating and testing collections of permuted mutants.

In some embodiments, the location of the new termini of a small subunit or large subunit may be selected based on the secondary structure of a subunit, the proximity to the other subunit, the ribosome viability, or any combination thereof.

The secondary structure of either or both of the large subunit and the small subunit may be used to determine the location for new termini. In certain embodiments, the new termini are prepared in a helix of a native subunit. In some specific embodiments the new termini are prepared in hairpin of a native subunit.

The proximity to the other subunit may be used to select the location of the new termini in either or both of the large subunit or the small subunit. In certain embodiments, the new termini are located in the subunit solvent side of the native subunit. In some other embodiments the new termini are located close to the subunit interface rim. In certain specific embodiments the new termini are located in the subunit solvent side and close to the subunit interface rim.

Ribosome viability may be used to select the location of the new termini in either or both of the large subunit or the small subunit. For example, polynucleotide sequences or secondary structures that are in either or both of the large subunit or the small subunit that are not highly conserved in populations may be used to select the location for new termini.

In certain embodiments where the engineered ribosome is a 23S construct, the linking moiety may covalently bond helix 10, helix 38, helix 42, helix 54, helix 58, helix 63, helix 78, or helix 101 of a permuted variant of the 23S rRNA. In certain embodiments where the engineered ribosome is a 16S rRNA construct, the linking moiety may covalently bond helix 11, helix 26, helix 33, or helix 44 of a permuted variant of the 16S rRNA. In certain other embodiments where the engineered ribosome is a 16S construct, the linking moiety may covalently bond close to the E-site of a permuted variant of the 16S rRNA. In specific embodiments where the engineered ribosome is a 16S-23S construct, the linking moiety may covalently bond helix 44 of a permuted variant 16S rRNA with helix 101 of a permuted variant 23S rRNA, the linking moiety may covalently bond helix 26 of a permuted variant 16S rRNA with helix 10 of a permuted variant 23S rRNA, the linking moiety may covalently bond helix 33 of a permuted variant 16S rRNA with helix 38 of a permuted variant 23S rRNA, the linking moiety may covalently bond helix 11 of a permuted variant 16S rRNA with helix 58 of a permuted variant 23S rRNA, the linking moiety may covalently bond helix 44 of a permuted variant 16S rRNA with helix 58 of a permuted variant 23S rRNA, the linking moiety may covalently bond helix 26 of a permuted 1 variant 6S rRNA with helix 54 of a permuted variant 23S rRNA, the linking moiety may covalently bond helix 11 of a permuted variant 16S rRNA with helix 63 of a permuted variant 23S rRNA, or the linking moiety may covalently bond helix 44 of a permuted variant 16S rRNA with helix 63 of a permuted variant 23S rRNA.

As explained above, the linking moiety must be sufficiently short to prevent degradation and to ensure subunit cis-association while long enough for minimal inhibition of subunit movement required for translation initiation, elongation, and peptide release. As a result, the linking moiety must span tens of Angstroms between the new termini on the large subunit and the short subunit.

Polynucleotides Encoding the Tethered Ribosome

Polynucleotides encoding the tethered ribosome are also disclosed. The polynucleotide encoding for the tethered ribosome may be any polynucleotide capable of being expressed to produce the rRNA of the tethered ribosome. FIG. 2B illustrates a polynucleotide for preparing the rRNA of the tethered ribosome. The polynucleotide 400 comprises a sequence that encodes for the rRNA of a S1 domain 401 followed, in order, by a sequence that encodes for the rRNA of a T1 linker 405, a sequence that encodes for the rRNA of a L1 domain 402, a sequence that encodes for the rRNA of a C domain 406, a sequence that encodes for the rRNA of a L2 domain 403, a sequence that encodes for the rRNA of a T2 linker 407, and a sequence that encodes for the rRNA of a S2 domain 404, from 5' to 3'.

The polynucleotides encoding for the tethered ribosome may further comprise genes encoding for other rRNA subunits of the ribosome or ribosomal proteins. For example, the polynucleotide encoding for an engineered ribosome comprising a permuted 23S rRNA tethered to a permuted 16S rRNA, the polynucleotide may further comprise a gene encoding for a 5S rRNA.

In certain embodiments the polynucleotide is a vector that may introduce foreign genetic material into a host cell. The vector may be a plasmid, viral vector, cosmid, or artificial chromosome.

FIGS. 4A, B provide examples of plasmids that encode for a prokaryotic ribosome having separable subunits (FIG. 4A) and a polynucleotide encoding for a tethered ribosome (FIG. 4B). In a FIG. 4A, the plasmid 600 comprises a promoter 612, a gene encoding for a 16S subunit 601, including a representation of the processing stems indicated by the smaller rectangles, a tRNA gene 613, a gene encoding a 23S subunit 602, including a representation of the processing stems indicated by the smaller rectangles, a gene encoding a 5S subunit 611, a gene encoding antibiotic resistance 614, and a origin of replication gene 615.

In contrast to the plasmid encoding the ribosome having separable subunits, the plasmid encoding a tethered ribosome 700 has a chimeric gene encoding for a large subunit, a small subunit, and a linking moiety connecting the large subunit with the small subunit 701-707. Plasmid comprises the genes for the expression of the tethered ribosome 720. Optionally, the plasmid may further comprise one or more addition genes 740.

The gene encoding for the tethered subunits comprises the sequence that encodes for the rRNA of a S1 domain 701 followed, in order, by a sequence that encodes for the rRNA of a T1 linker 705, a sequence that encodes for the rRNA of a L1 domain 702, a sequence that encodes for the rRNA of a C domain 706, a sequence that encodes for the rRNA of a L2 domain 703, a sequence that encodes for the rRNA of a T2 linker 707, and a sequence that encodes for the rRNA of a S2 domain 704, from 5' to 3'. The processing sequences of a small subunit flanking the chimeric gene, indicated by the small rectangles, may be retained for proper maturation of the small subunit termini, whereas the processing sequences for the large subunit 716 may be moved to another location in the plasmid or eliminated entirely to prevent cleavage of the large subunit out of the hybrid.

In certain embodiments, the plasmid encoding the tethered subunits further comprises a gene encoding a 5S subunit 711, a gene encoding antibiotic resistance 714, and an origin of replication gene 715.

Optionally, the gene encoding the tethered subunits may comprise a modified anti-Shine-Dalgarno sequence 708 (circle). Although the modified anti-SD sequence is shown in FIG. 4B to be located within the sequence encoding the S2 domain, the modified anti-Shine Dalgarno sequence may be located in either of the small subunit domains, i.e. S1 or S2.

Optionally, the plasmid encoding the tethered subunits comprises one or more additional genes 740. The additional gene may comprise a modified Shine-Dalgarno sequence that is complimentary with a modified anti-Shine-Dalgarno sequence of the tethered ribosome. In certain embodiments that additional gene may be a reporter gene. In specific embodiments, the reporter gene is a green fluorescent protein.

Preparing the Polynucleotide

Methods of preparing the polynucleotide are also disclosed herein. The method comprises preparing a plasmid encoding a permuted subunit rRNA construct, identifying a viable permuted subunit rRNA constructs, and preparing a polynucleotide encoding the engineered ribosome comprising a large subunit, a small subunit, and a linking moiety that tethers the small subunit with the large subunit.

Preparation of a plasmid encoding a permuted subunit rRNA construct may be accomplished by the circular permutation approach that connects the native ends of the subunit and prepares new termini FIG. 3. Preparation of the plasmid may comprise the steps of template preparation, plasmid backbone preparation, and assembly. The template preparation step may be accomplished by plasmid digestion and ligation. By way of example, a CP23S template may be prepared from pCP23S-EagI plasmid by EagI digestion and ligation. Each CP23S variant is generated by PCR using a circularized 23S rRNA gene as a template and a unique primer pair, with added sequences overlapping the destination plasmid backbone. The plasmid backbone preparation step may be accomplished by digestion of a plasmid with a restriction enzyme that linearized the backbone at the subunit processing stem site. By way of example, Plasmid backbone is prepared by digestion of pAM552-23S-AflII with AflII restriction enzyme, which linearizes the backbone at the 23S processing stem site. The assembly step incorporates the template with the plasmid backbone to prepare the plasmid encoding the permuted subunit rRNA. The assembly step may be accomplished by Gibson assembly.

To identify permuted subunit rRNA viable constructs, the plasmid encoding the permuted subunit rRNA may be introduced in to host cell strains and a screening mechanism is used to identify transformants. The host cells comprise the plasmid as well as a plasmid encoding for the wild-type rRNA operon and may be spotted onto an agar plate along with an antibiotic. The selection mechanism includes identifying transformants resistant to the antibiotic. By way of example, the plasmids may be transformed into Δ7 rrn SQ171 strain carrying pCSacB plasmid with wild-type rRNA operon and transformants resistant to ampicillin, erythromycin and sucrose are selected. To confirm complete replacement of the wild-type rRNA operon with the plasmid encoding for the permuted subunit rRNA, a three-primer diagnostic PCR check may be performed on the total plasmid extract or total cellular RNA may be analyzed.

Preparing a polynucleotide encoding the engineered ribosome comprising a large subunit, a small subunit, and a linking moiety that tethers the small subunit with the large subunit comprises grafting the permuted subunit rRNA construct and the linking moiety into the other subunit. In certain embodiments the preparation step may also include preparing a plasmid comprising the polynucleotide encoding the engineered ribosome comprising a large subunit, a small subunit, and a linking moiety that tethers the small subunit with the large subunit. In other embodiments, the preparation step may also include preparing a plasmid comprising the polynucleotide encoding the engineered ribosome comprising a large subunit, a small subunit, and a linking moiety that tethers the small subunit with the large subunit and a polynucleotide encoding for an additional gene.

Preparing the Tethered Ribosome

Also disclosed are methods for preparing the tethered ribosome. The tethered ribosome may be prepared by expressing a polynucleotide encoding the engineered ribosome. In certain embodiments preparation of the tethered ribosome further comprises preparing the polynucleotide encoding the engineered ribosome. In other embodiments the preparation of the tethered ribosome further comprises transforming a cell with the polynucleotide encoding the engineered ribosome. In some specific embodiments, the preparation of the tethered ribosome further comprises preparing the polynucleotide and transforming a cell with the polynucleotide.

Tethered Ribosome Evolution

Also discloses are methods for evolving the tethered ribosome. Methods for tethered ribosome evolution include expressing a polynucleotide encoding for the engineered ribosome and selecting a mutant. The selection step may comprise a negative selection step, a positive selection step, or both a negative and a positive selection step. The mutant selected may comprise a tethered ribosome having a change-of-function mutation. The change-of-function mutation may be a gain-of-function mutation or a loss-of-function mutation.

Utility and Applications of Tethered Ribosomes

Some uses and applications of the tethered ribosomes are described below.

Artificial Cells

Artificial cells are disclosed. The artificial cell may comprise a polynucleotide encoding an engineered ribosome, the engineered ribosome comprising a small subunit, a large subunit, and a linking moiety, wherein the linking moiety tethers the small subunit with the large subunit. The artificial cell comprising a polynucleotide encoding the engineered ribosome may be capable of expressing the polynucleotide to prepare the engineered ribosome. In other embodiments, the artificial cell comprises the engineered ribosome. In some specific embodiments the artificial cell comprises a polynucleotide encoding the engineered ribosome and the engineered ribosome.

Artificial cells may comprise one or more translations mechanism. In a first embodiment, the artificial cell has one translation mechanism comprising an engineered ribosome, the engineered ribosome comprising a small subunit, a large subunit, and a linking moiety, wherein the linking moiety tethers the small subunit with the large subunit.

In another embodiment, the artificial cell may comprise two translation mechanisms. The first translation mechanism may comprise a ribosome wherein the ribosome lacks a linking moiety between the large subunit and the small subunit. The second translation mechanism comprises an engineered ribosome, the engineered ribosome comprising a small subunit, a large subunit, and a linking moiety, wherein the linking moiety tethers the small subunit with the large subunit. In some embodiments the second translation mechanism is an orthogonal translation mechanism. In some specific embodiments the first translation mechanism and the second translation mechanism are orthogonal translation mechanisms. An orthogonal translation mechanism may be prepared by modifying the anti-Shine Dalgarno sequence of the engineered ribosome to permit translation of templates having a complementary or cognate Shine-Dalgarno sequence different from the endogenous cellular mRNAs.

In another embodiment, a cell comprising a first mechanism and a second mechanism for protein translation is disclosed. The first mechanism is the natural translation mechanism wherein mRNA is translated by a ribosome in accordance with the natural genetic code (that is, triplet code endogenous to the cell). The second mechanism includes an artificial mechanism derived from a tethered ribosome that functions to allow for expression of a heterologous gene.

Preparation of Sequence-Defined Polymers

Methods for preparing sequence-defined polymers are also provided. In certain embodiments the method for preparing a sequence defined polymer comprises providing an engineered ribosome and providing an mRNA or DNA template encoding the sequence-defined polymer, wherein the engineered ribosome comprises a small subunit, a large subunit, and a linking moiety and wherein the linking moiety tethers the small subunit with the large subunit. In one aspect of the method, one of any of the steps includes adding at least one exogenous DNA template encoding an mRNA for the sequence-defined polymer.

In one aspect of the method, the sequence-defined polymer is a natural biopolymer. In another aspect of the method, the sequence-defined polymer is a non-natural biopolymer. In certain embodiments, the sequence-defined polymer comprises an amino acid. In certain embodiments the amino acid may be a natural amino acid. As used herein a natural amino acid is a proteinogenic amino acid encoded directly by a codon of the universal genetic code. In certain embodiments the amino acid may be an unnatural amino acid. As used here an unnatural amino acid is a nonproteinogenic amino acid. Examples of unnatural amino acids include, but are not limited to a p-acetyl-L-phenylalanine, a p-iodo-L-phenylalanine, an O-methyl-L-tyrosine, a p-propargyloxyphenylalanine, a p-propargyl-phenylalanine, an L-3-(2-naphthyl)alanine, a 3-methyl-phenylalanine, an O-4-allyl-L-tyrosine, a 4-propyl-L-tyrosine, a tri-O-acetyl-GlcNAcpβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an unnatural analogue of a methionine amino acid; an unnatural analogue of a leucine amino acid; an unnatural analogue of a isoleucine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an α-hydroxy containing acid; an amino thio acid; an α,α disubstituted amino acid; a β-amino acid; a D-amino acid; a γ-amino acid, a cyclic amino acid other than proline or histidine, and an aromatic amino acid other than phenylalanine, tyrosine or tryptophan. In certain embodiments the sequence-defined polymer is a polypeptide or protein.

In one aspect of the method, the tethered subunit arrangement comprises a linking moiety between the 23S and 16S rRNAs. In one respect of this aspect, the linking moiety covalently bonds helix 101 of the 23S rRNA to helix 44 of the 16S rRNA. In another respect of this aspect, the linking moiety comprises a polynucleotide having a length ranging from 5 nucleotides to 200 nucleotides. The engineered ribosome can further include an engineered 16S rRNA having a modified anti-Shine-Dalgarno sequence to permit translation in vitro of translation templates having a complementary or cognate SD sequence differing from endogenous cellular mRNAs. In this way, selective translation in vitro of mRNA to produce sequence defined biopolymers with high efficiency is possible.

In one aspect of the method, the mRNA or DNA template encodes a modified Shine-Dalgarno sequence. In certain embodiments the engineered ribosome comprises an anti-Shine-Dalgarno sequence complementary or cognate to the Shine-Dalgarno sequence encoded by the mRNA or DNA template.

Sequence-defined polymers may be prepared in vitro. The method for preparing a sequence-defined polymer in vitro further comprises providing a ribosome-depleted cellular extract or a purified translation system. In certain embodiments, the wherein the ribosome-depleted cellular extract comprises an S150 extract prepared from mid- to late-exponential growth phase cell cultures or cultures having an O.D.600~3.0 at time of harvest. In one aspect of the method, the ribosome-depleted extract is prepared with one or more polyamines, such as spermine, spermidine and putrescine, or combinations thereof. In one aspect of the method, the ribosome-depleted extract is prepared with a concentration of salts from about 50 mM to about 300 mM.

The preparation of ribosome-depleted cellular extracts and methods of using them for supporting translation in vitro of sequence-defined polymers is disclosed in International Patent Application No. PCT/US14/35376 to Michael Jewett et al., entitled IMPROVED METHODS FOR MAKING RIBOSOMES, filed Apr. 24, 2014, the contents of which are incorporated by reference herein in its entirety.

In one aspect of the method, mRNA encodes a modified Shine-Dalgarno sequence differing from endogenous cellular mRNAs present in the ribosome-depleted cellular extract. In one respect of this aspect, the engineered ribosome further includes an engineered 16S rRNA having a modified anti-Shine-Dalgarno sequence complementary or cognate to the modified Shine-Dalgarno sequence to permit translation in vitro of the mRNA to prepare the sequence defined biopolymer in vitro.

In one aspect, the method is configured for fed-batch operation or continuous operation. In another aspect of the method, at least one substrate is replenished during operation.

In one aspect of the method, at least one step includes a DNA-dependent RNA polymerase. In one aspect of the method, at least one macromolecular crowding agent is included in one of the steps. In one aspect of the method, at least one reducing agent (e.g., dithiothreitol, tris(2-carboxyethyl) phosphine hydrochloride, etc.) is included in one of the steps.

Sequence-defined polymers may be prepared in vivo. The method for preparing a sequence-defined polymer in vivo may occur in an artificial cell as disclosed above. The artificial cell may have a translation mechanism comprising an engineered ribosome, wherein the engineered ribosome comprises a small subunit, a large subunit, and a linking moiety and wherein the linking moiety tethers the small subunit with the large subunit. In certain embodiments the artificial cell has one translation mechanism. In other embodiments the cell has two translations mechanisms. In specific embodiments, the cell has two translations mechanisms, the first protein translation mechanism comprising a ribosome, wherein the ribosome lacks a linking moiety between the large subunit and the small subunit and the second protein translation mechanism comprises the engineered ribosome.

TERMINOLOGY

Unless defined otherwise, all technical and scientific terms used herein have the same meaning as commonly understood by one of skill in the art to which the invention pertains. All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

A range includes each individual member. Thus, for example, a group having 1-3 members refers to groups having 1, 2, or 3 members.

It should also be understood that, unless clearly indicated to the contrary, in any methods claimed herein that include more than one step or act, the order of the steps or acts of the method is not necessarily limited to the order in which the steps or acts of the method are recited.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use an aspect of a described embodiment or feature contained in the same, or a definitive decision to use a specific skill regarding a described embodiment or feature contained in the same. In this latter context, the modal verb "may" has the same meaning and connotation as the auxiliary verb "can."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The terms "nucleic acid" and "oligonucleotide," as used herein, refer to polydeoxyribonucleotides (containing 2-deoxy-DRibose), polyribonucleotides (containing DRibose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present invention, an oligonucleotide also can comprise nucleotide analogs in which the base, sugar or phosphate backbone is modified as well as non-purine or non-pyrimidine nucleotide analogs.

A "fragment" of a polynucleotide is a portion of a polynucleotide sequence which is identical in sequence to but shorter in length than a reference sequence. A fragment may comprise up to the entire length of the reference sequence, minus at least one nucleotide. For example, a fragment may comprise from 5 to 1000 contiguous nucleotides of a reference polynucleotide. In some embodiments, a fragment may comprise at least 5, 10, 15, 20, 25, 30, 40, 50, 60, 70, 80, 90, 100, 150, 250, or 500 contiguous nucleotides of a reference polynucleotide. Fragments may be preferentially selected from certain regions of a molecule. The term "at least a fragment" encompasses the full length polynucleotide. A "variant," "mutant," or "derivative" of a reference polynucleotide sequence may include a fragment of the reference polynucleotide sequence.

Regarding polynucleotide sequences, percent identity may be measured over the length of an entire defined polynucleotide sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Regarding polynucleotide sequences, "variant," "mutant," or "derivative" may be defined as a nucleic acid sequence having at least 50% sequence identity to the particular nucleic acid sequence over a certain length of one of the nucleic acid sequences using blastn with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of nucleic acids may show, for example, at least 20%, at least 30%, at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques known in the art. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

The nucleic acids disclosed herein may be "substantially isolated or purified." The term "substantially isolated or purified" refers to a nucleic acid that is removed from its natural environment, and is at least 60% free, preferably at least 75% free, and more preferably at least 90% free, even more preferably at least 95% free from other components with which it is naturally associated.

Oligonucleotides can be prepared by any suitable method, including direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Letters 22:1859-1862; and the solid support method of U.S. Pat. No. 4,458,066, each incorporated herein by reference. A review of synthesis methods of conjugates of oligonucleotides and modified nucleotides is provided in Goodchild, 1990, Bioconjugate Chemistry 1(3): 165-187, incorporated herein by reference.

The term "primer," as used herein, refers to an oligonucleotide capable of acting as a point of initiation of DNA synthesis under suitable conditions. Such conditions include those in which synthesis of a primer extension product complementary or cognate to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary (i.e., "cognate") to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly(A)n sequence, where n is in the range from about 20 to about 200). The region of the primer that is sufficiently complementary to the template to hybridize is referred to herein as the hybridizing region.

The term "promoter" refers to a cis-acting DNA sequence that directs RNA polymerase and other trans-acting transcription factors to initiate RNA transcription from the DNA template that includes the cis-acting DNA sequence.

The terms "target, "target sequence", "target region", and "target nucleic acid," as used herein, are synonymous and refer to a region or sequence of a nucleic acid which is to be amplified, sequenced or detected.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions; the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, N.Y.; Wetmur, 1991, Critical Review in Biochem. and Mol. Biol. 26(3/4):227-259; and Owczarzy et al., 2008, Biochemistry, 47: 5336-5353, which are incorporated herein by reference).

As used herein, the term "complementary" in reference to a first polynucleotide sequence and a second polynucleotide sequence means that the first polynucleotide sequence will base-pair exactly with the second polynucleotide sequence throughout a stretch of nucleotides without mismatch. The term "cognate" may in reference to a first polynucleotide sequence and a second polynucleotide sequence means that the first polynucleotide sequence will base-pair with the second polynucleotide sequence throughout a stretch of nucleotides but may include one or more mismatches within the stretch of nucleotides.

The term "amplification reaction" refers to any chemical reaction, including an enzymatic reaction, which results in increased copies of a template nucleic acid sequence or results in transcription of a template nucleic acid. Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, T3 RNA polymerase, T7 RNA polymerase, SP6 RNA polymerase and *E. coli* RNA polymerase, among others. The foregoing examples of RNA polymerases are also known as DNA-dependent RNA polymerase. The polymerase activity of any of the above enzymes can be determined by means well known in the art.

As used herein, the term "sequence defined polymer" refers to a polymer having a specific primary sequence. A sequence defined polymer can be equivalent to a genetically-encoded defined polymer in cases where a gene encodes the polymer having a specific primary sequence.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, "expression template" refers to a nucleic acid that serves as substrate for transcribing at least one RNA that can be translated into a polypeptide or protein. Expression templates include nucleic acids composed of DNA or RNA. Suitable sources of DNA for use a nucleic acid for an expression template include genomic DNA, plasmid DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

As used herein, "tethered," "conjoined," "linked," "connected," "coupled" and "covalently-bonded" have the same meaning as modifiers.

As used herein, "tethered ribosome," "engineered ribosome," and "Ribo-T" will be used interchangeably.

As used here, "CP" refers to a circularly permuted subunit. As used herein, when CP is followed by "23S" that refers to a circularly permuted 23S rRNA. As used herein, when CP followed by a number may refer to the location of the new 5' end in a secondary structure, e.g. CP101 means the new 5' end is in helix 101 of the 23S rRNA, or to the location of the new 5' nucleotide, e.g. CP2861 means the new 5' nucleotide is the nucleotide 2861 of the 23 rRNA, depending on context.

As used herein, "translation template" refers to an RNA product of transcription from an expression template that can be used by ribosomes to synthesize polypeptide or protein.

As used herein, a "ribosomal binding site" or "RBS" is a sequence of nucleotides upstream of the start codon of an mRNA transcript that is responsible for the recruitment of a ribosome during the initiation of protein translation. The RBS may include the Shine-Dalgarno sequence. The Shine-Dalgarno (SD) sequence is a ribosomal binding site in prokaryotic messenger RNA, which generally is located approximately 8 bases upstream of the start codon AUG. The SD sequence helps recruit the ribosome to the messenger RNA (mRNA) to initiate protein synthesis by aligning the ribosome with the start codon. The six-base consensus sequence is AGGAGG and in *E. coli* the sequence is AGGAGGU.

Miscellaneous

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

ILLUSTRATIVE EMBODIMENTS

The following embodiments are illustrative and should be interpreted to limit the scope of the claimed subject matter.

Embodiment 1

Figure 15:
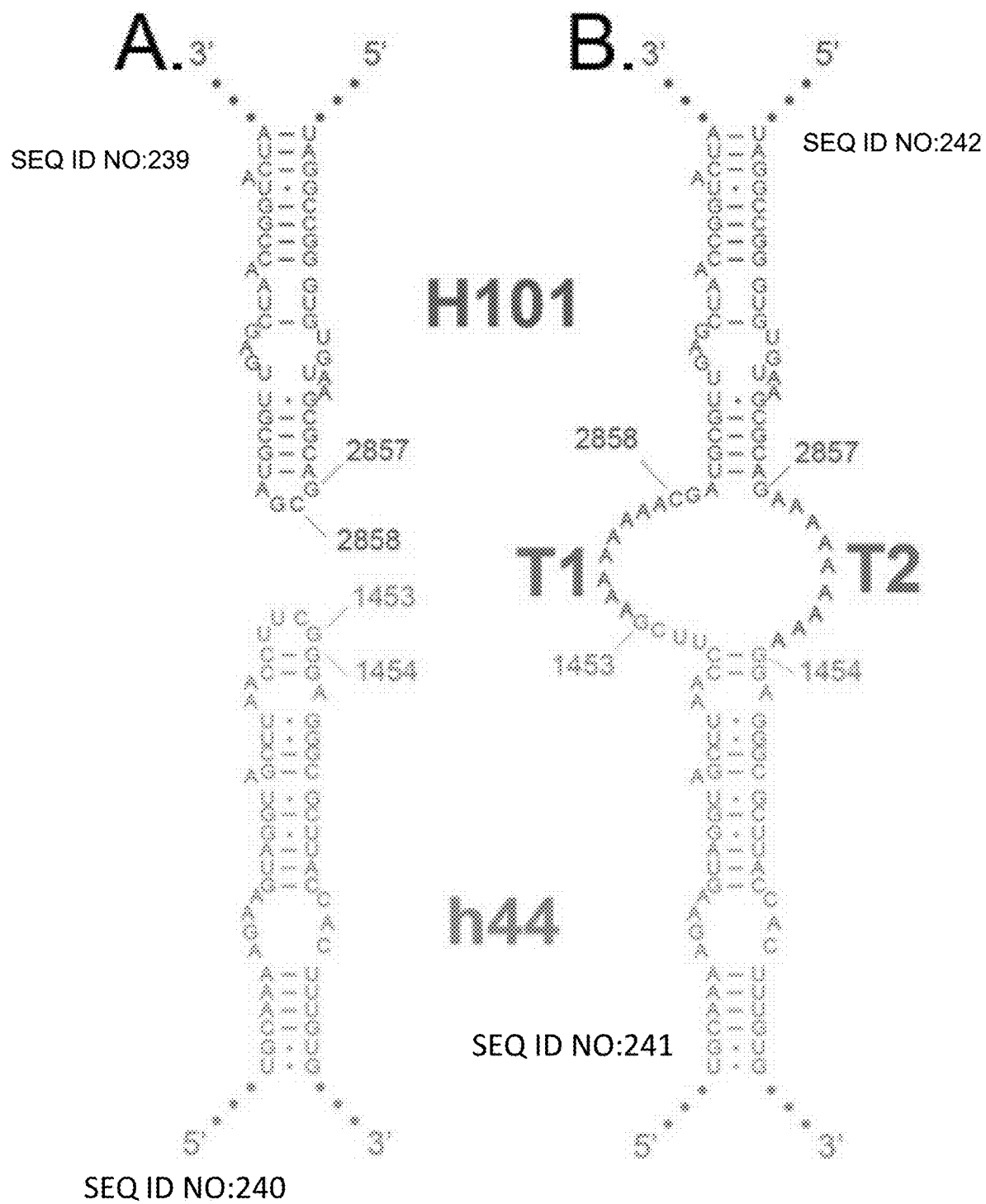
FIG. 15 shows one embodiment of a tether placement and design including libraries for optimization. A. wild-type helices, H101 on 23S rRNA and h44 on 16S rRNA. B. Tethered ribosome design per Example 1, UUCG native loop sequence+8A+CGA native loop for 5' tether, T1; and G+9A for 3' tether, T2. C. and D. Optimizing tether length. C. Library L1: paired 5' tether T1 poly A from 7-20 nucleotides and 3' tether T2 poly T from 7-20 nucleotides. D, Library L2: unpaired polyA on both T1 and T2, ranging in 7-20 nucleotides long. E. and F. Optimizing tether composition. E. Library L3: T1, UUCG native loop sequence+8N randomized sequence+CGA native loop; T2 G+9N randomized sequence. F. Library L4: randomized T1 (15N) and T2 (10N) of tether. G. Exemplary performing tether sequence isolated from Library L4 referred to as Ribo-T-v2.
Figure 15:
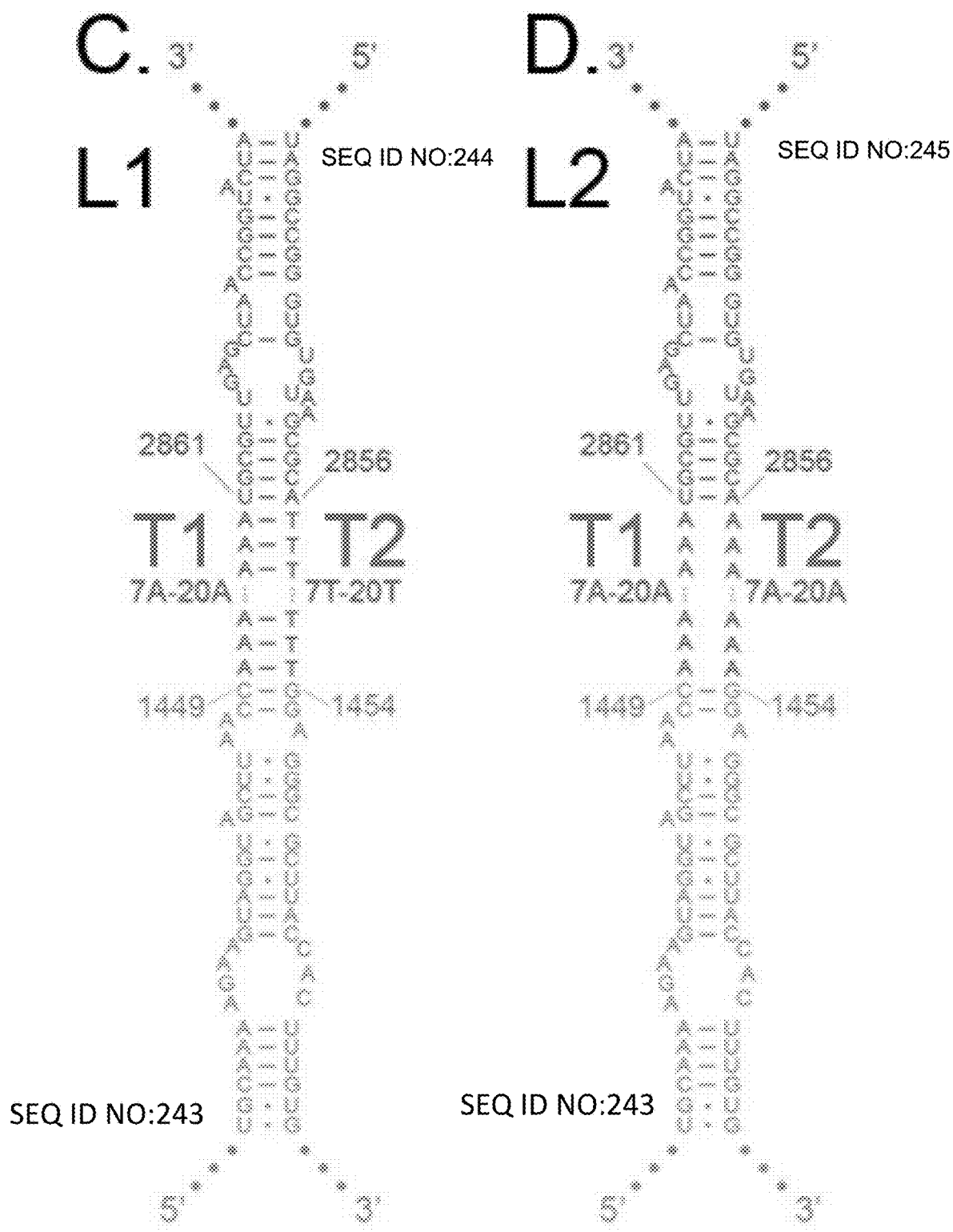
Figure 15:
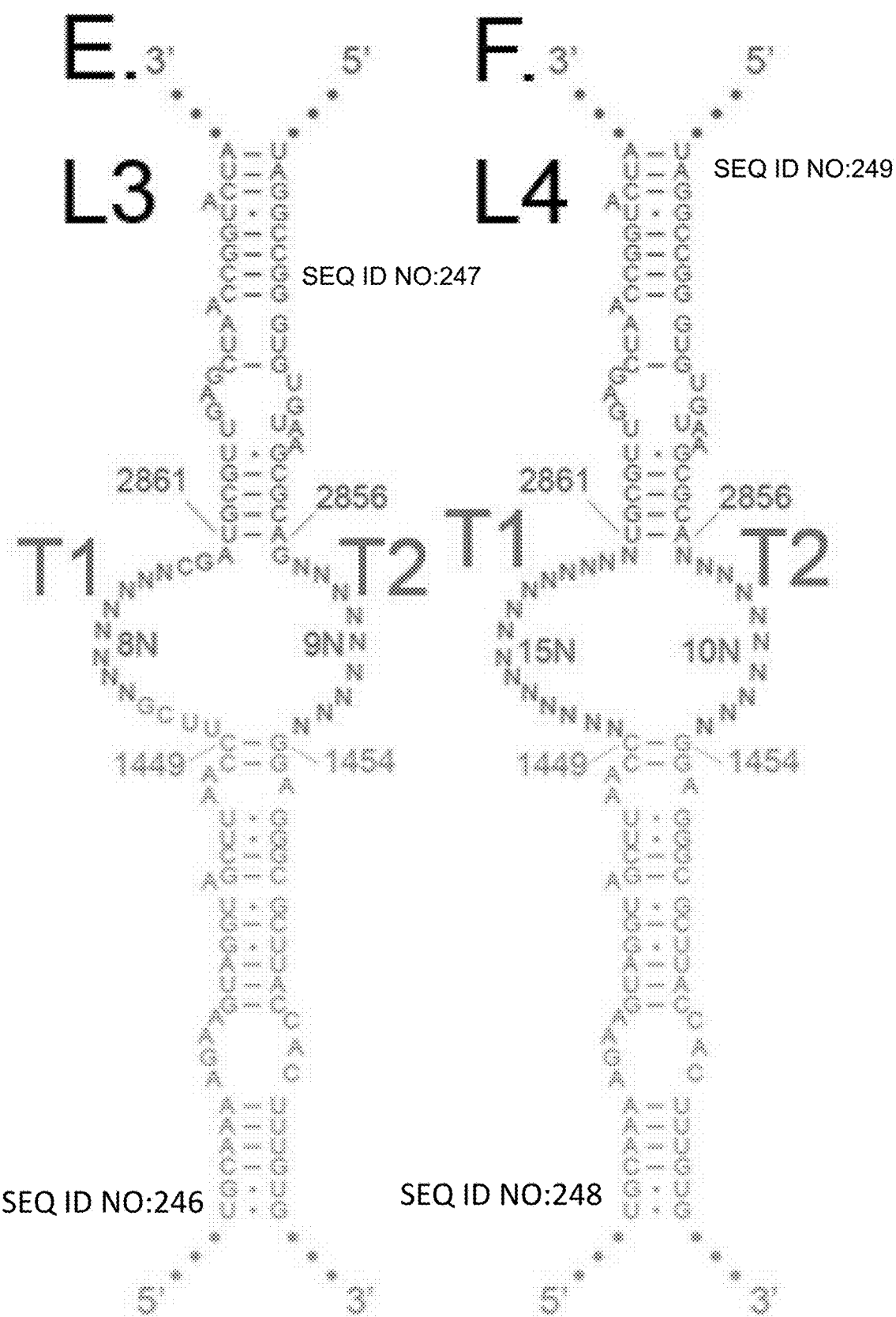
Figure 15:
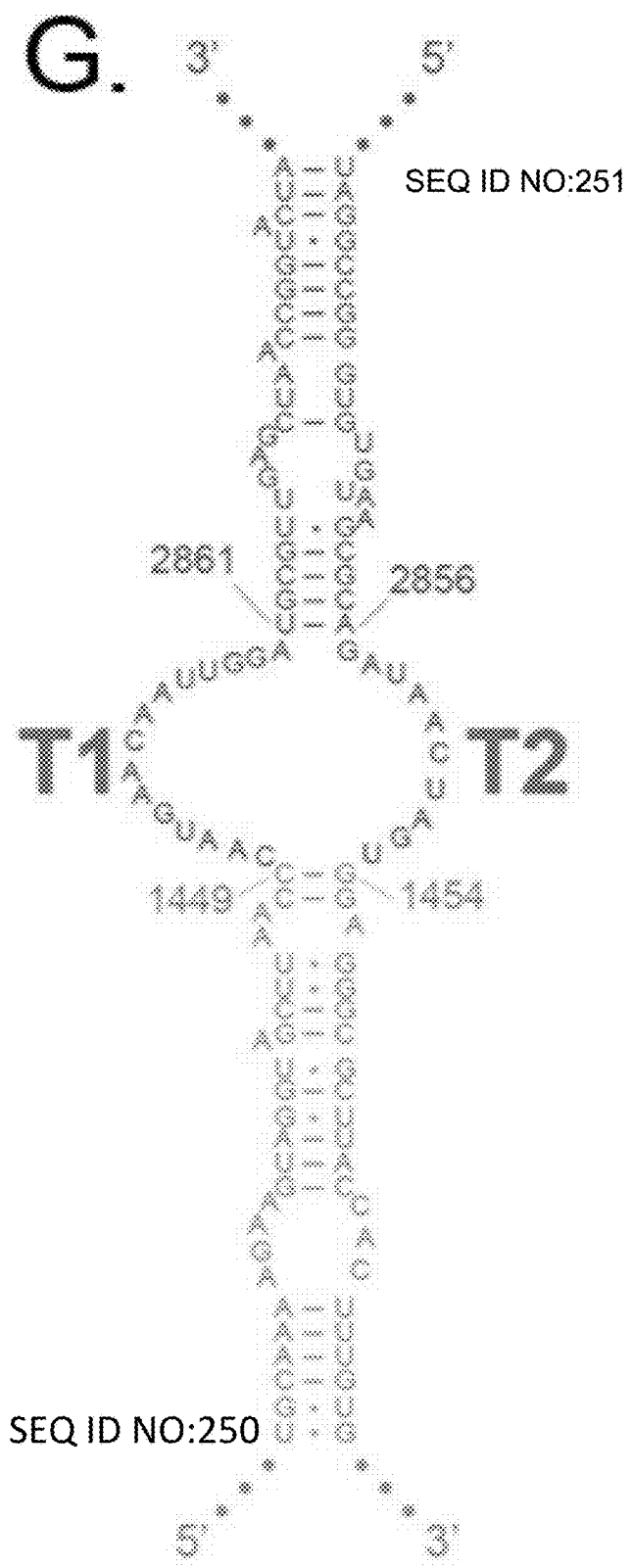
Figure 17:
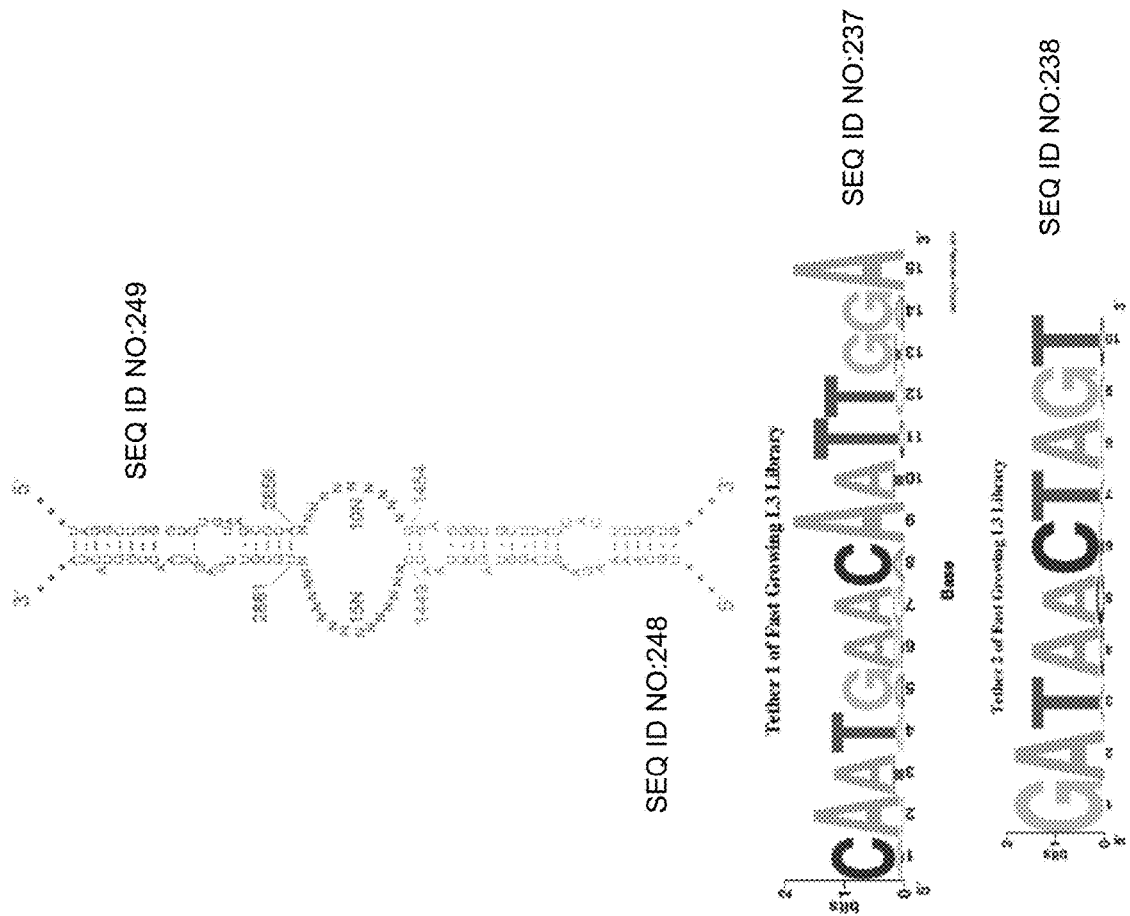
FIG. 17 provides the sequences of the fastest growing constructs of Library L4, as compared to the untethered wild-type control (pAM552) and the original pRibo-T system.

An engineered ribosome, the engineered ribosome comprising a small subunit, a large subunit, and a linking moiety, a. wherein the linking moiety tethers the small subunit with the large subunit and b. wherein the engineered ribosome is capable of supporting translation of a sequence defined polymer, and optionally where the linking moiety comprises a polynucleotide sequence selected from the sequences in FIG. 15 or 17.

Embodiment 2

The engineered ribosome of embodiment 1, wherein the small subunit comprises rRNA, wherein the large subunit comprises rRNA, and wherein the linking moiety tethers the rRNA of the small subunit with the rRNA of the large subunit, and optionally where the linking moiety comprises a polynucleotide sequence selected from the sequences in FIG. 15 or 17.

Embodiment 3

The engineered ribosome of embodiment 1 or 2, wherein the large subunit comprises a permuted variant of a 23S rRNA (e.g., a circularly permuted variant of 23 rRNA).

Embodiment 4

The engineered ribosome of any of embodiments 1-3, wherein the small subunit comprises a permuted variant of a 16S rRNA (e.g., a circularly permuted variant of 23 rRNA).

Embodiment 5

The engineered ribosome of any of embodiments 1-4, wherein the small subunit comprises a modified anti-Shine-Dalgarno sequence to permit translation of templates having a complementary and/or cognate Shine-Dalgarno sequence different from endogenous cellular mRNAs (e.g., wherein the modified anti-Shine-Dalgarno sequence of the small subunit is complementary and/or cognate to the Shine-Dalgarno sequence different from endogenous cellular mRNAs).

Embodiment 6

The engineered ribosome of any of embodiments 1-5, wherein the linking moiety covalently bonds a helix of the large subunit to a helix of the small subunit (e.g., as illustrated in FIG. 15 or 17).

Embodiment 7

The engineered ribosome of any of embodiments 3-6, wherein the linking moiety covalently bonds helix 10, helix 38, helix 42, helix 54, helix 58, helix 63, helix 78, or helix 101 of the permuted variant of the 23S rRNA (e.g., as illustrated in FIG. 15 or 17).

Embodiment 8

The engineered ribosome of any of embodiments 4-7, wherein the linking moiety covalently bonds helix 11, helix 26, helix 33, or helix 44 of the permuted variant of the 16S rRNA (e.g., as illustrated in FIG. 15 or 17).

Embodiment 9

The engineered ribosome of any of embodiments 1-8, wherein the large subunit comprises or consists essentially of a L1 polynucleotide domain (e.g., a fragment of 23S rRNA), a L2 polynucleotide domain (e.g., a fragment of 23S rRNA), and a C polynucleotide domain, wherein the L1 domain is followed, in order, by the C domain and the L2 domain, from 5' to 3'.

Embodiment 10

The engineered ribosome of embodiment 9, wherein the polynucleotide comprising or consisting essentially of the L2 domain followed by the L1 domain, from 5' to 3', is substantially identical to 23S rRNA or a fragment of 23S rRNA.

Embodiment 11

The engineered ribosome of embodiment 9 or 10, wherein the polynucleotide comprising or consisting essentially of the L2 domain followed by the L1 domain, from 5' to 3', is at least 75%, 80%, 85%, 90%, or 95% identical to 23S rRNA or a fragment of 23S rRNA (or at least 96%, 97%, 98%, or 99% identical to 23S rRNA or a fragment of 23S rRNA).

Embodiment 12

The engineered ribosome of any of embodiments 9-11, wherein the C domain comprises a polynucleotide having a length ranging from 1-200 nucleotides.

Embodiment 13

The engineered ribosome of any of embodiments 9-12, wherein the C domain comprises a GAGA polynucleotide.

Embodiment 14

The engineered ribosome of any of embodiments 1-13, wherein the small subunit comprises or consists essentially of a S1 polynucleotide domain (e.g., a fragment of 16S rRNA) and a S2 polynucleotide domain (e.g., a fragment of 16S rRNA), wherein the S1 domain is followed, in order, by the S2 domain, from 5' to 3'.

Embodiment 15

The engineered ribosome of embodiment 14, wherein the polynucleotide comprising or consisting essentially of the S1 domain followed by the S2 domain, from 5' to 3', is substantially identical to a 16S rRNA (or a fragment of 16S rRNA).

Embodiment 16

The engineered ribosome of embodiment 14 or 15, wherein the polynucleotide comprising or consisting essentially of the S1 domain followed by the S2 domain, from 5' to 3', is at least 75%, 80%, 85%, 90%, or 95% identical to a 16S rRNA (or at least 96%, 97%, 98%, or 99% identical to 16S rRNA or a fragment of 16S rRNA).

Embodiment 17

The engineered ribosome of any of embodiments 1-16, wherein the linking moiety comprises a T1 polynucleotide domain and a T2 polynucleotide domain, optionally wherein the T1 polynucleotide domain and/or the T2 polynucleotide domain comprises or consists essentially of a polynucleotide sequence of FIG. 15 or 17.

Embodiment 18

The engineered ribosome of embodiment 17, wherein the T1 domain links the S1 domain and the L1 domain and wherein the S1 domain is followed, in order, by the T1 domain and the L1 domain, from 5' to 3'.

Embodiment 19

The engineered ribosome of embodiment 17 or 18, wherein the T1 domain comprises a polynucleotide having a length ranging from 5 to 200 nucleotides.

Embodiment 20

The engineered ribosome of embodiment 19, wherein the T1 domain comprises a polynucleotide having a length ranging from 7 to 20 nucleotides.

Embodiment 21

The engineered ribosome of any of embodiments 17-20, wherein the T1 domain comprises a polyadenine polynucleotide.

Embodiment 22

The engineered ribosome of any of embodiments 17-20, wherein the T1 domain comprises a polyadenine polynucleotide having a length of 7 to 12 adenine nucleotides.

Embodiment 23

The engineered ribosome of any of embodiments 17-22, wherein the T2 domain links the S2 domain and the L2 domain and wherein the L2 domain is followed, in order, by the T2 domain and the S2 domain, from 5' to 3'.

Embodiment 24

The engineered ribosome of any of embodiments 17-24, wherein the T2 domain comprises a polynucleotide having a length ranging from 5 to 200 nucleotides.

Embodiment 25

The engineered ribosome of embodiment 17, 23, or 24, wherein the T2 domain comprises a polynucleotide having a length ranging from 7 to 20 nucleotides.

Embodiment 26

The engineered ribosome of any of embodiments 17-25, wherein the T2 domain comprises a polyadenine polynucleotide.

Embodiment 27

The engineered ribosome of any of embodiments 17-26, wherein the T2 domain comprises a polyadenine polynucleotide having a length of 7 to 12 adenine nucleotides.

Embodiment 28

The engineered ribosome of any of embodiments 17-27, wherein the ribosome comprises the S1 domain followed, in order, by the T1 domain, the L1 domain, the C domain, the L2 domain, the T2 domain, and the S2 domain, from 5' to 3'.

Embodiment 29

The engineered ribosome of any of embodiments 17-28, wherein the ribosome comprises a polynucleotide consisting essentially of the S1 domain is followed, in order, by the T1 domain, the L1 domain, the C domain, the L2 domain, the T2 domain, and the S2 domain, from 5' to 3'.

Embodiment 30

The engineered ribosome of any of embodiments 1-29, wherein the engineered ribosome comprises a mutation.

Embodiment 31

The engineered ribosome of embodiment 30, wherein the mutation is a change-of-function mutation.

Embodiment 32

The engineered ribosome of embodiment 31, wherein the change-of-function mutation is in a peptidyl transferase center.

Embodiment 33

The engineered ribosome of embodiment 31, wherein the change-of-function mutation is in an A-site of the peptidyl transferase center.

Embodiment 34

The engineered ribosome of embodiment 31, wherein the change-of-function mutation is in the exit tunnel of the engineered ribosome.

Embodiment 35

The engineered ribosome of any of embodiments 1-35, wherein the engineered ribosome has an antibiotic resistance mutation.

Embodiment 36

A polynucleotide, the polynucleotide encoding the rRNA of the engineered ribosome of any of embodiments 1-35.

Embodiment 37

The polynucleotide of embodiment 36, wherein the polynucleotide is a vector.

Embodiment 38

The polynucleotide of embodiment 36 or 37, wherein the polynucleotide further comprises a gene to be expressed by the engineered ribosome.

Embodiment 39

The polynucleotide of embodiment 38, wherein the gene is a reporter gene.

Embodiment 40

The polynucleotide of embodiment 39, wherein the reporter gene is a green fluorescent protein gene.

Embodiment 41

Figure 21:
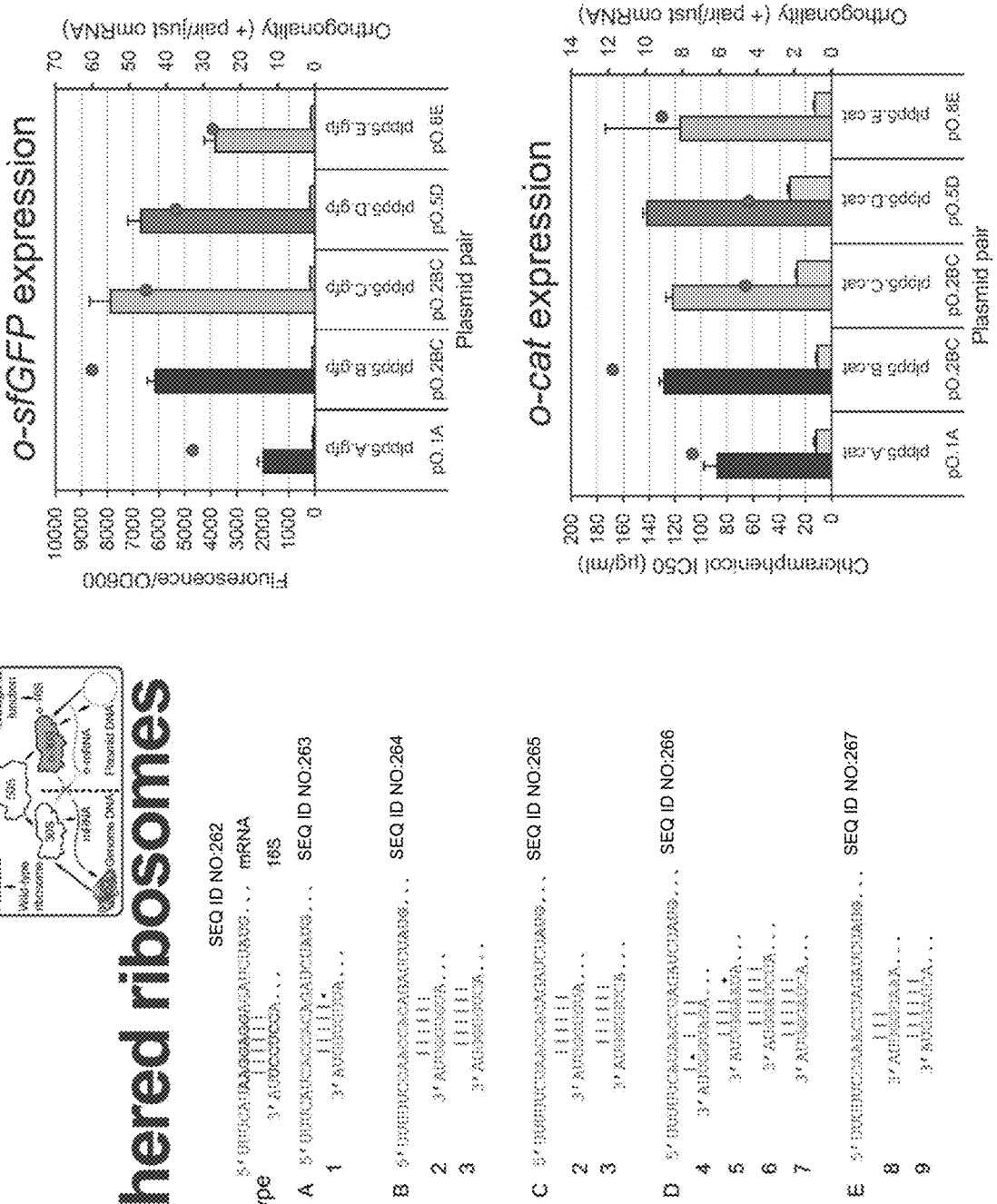
FIG. 21 shows testing of identified orthogonal pairs A, B, C, D, and E using untethered ribosomes.

The polynucleotide of any of embodiments 36-40, wherein the engineered ribosome comprises a modified anti-Shine-Dalgarno sequence and the gene comprises a complementary and/or cognate Shine-Dalgarno sequence to the engineered ribosome, optionally wherein the anti-Shine-Dalgarno sequence and/or the complementary and/or cognate Shine-Dalgarno sequence comprise a polynucleotide of FIG. 21.

Embodiment 42

The polynucleotide of any of embodiments 36-41, wherein the gene comprises a codon and the codon encodes for an unnatural amino acid.

Embodiment 43

A method for preparing an engineered ribosome, the method comprising expressing the polynucleotide of any of embodiments 36-42.

Embodiment 44

The method of embodiment 43, the method further comprising selecting a mutant.

Embodiment 45

The method of embodiment 44, wherein the selection step comprises a negative selection step, a positive selection step, or both a negative and a positive selection step.

Embodiment 46

A cell, the cell comprising (i) the polynucleotide of any of embodiments 36-42, (ii) the engineered ribosome of any of embodiments 1-35, or both (i) and (ii).

Embodiment 47

A cell, the cell comprising a first protein translation mechanism and a second protein translation mechanism, a. wherein the first protein translation mechanism comprises a ribosome, wherein the ribosome lacks a linking moiety between the large subunit and the small subunit and b. wherein the second protein translation mechanism comprises the engineered ribosome of any of embodiments 1-35.

Embodiment 48

A method for preparing a sequence-defined polymer, the method comprising (a) providing the engineered ribosome of any of embodiments 1-35 and (b) providing an mRNA or DNA template encoding the sequence-defined polymer.

Embodiment 49

The method of embodiment 48, wherein the sequence-defined polymer is prepared in vitro.

Embodiment 50

The method of embodiment 49, the method further comprising providing a ribosome-depleted cellular extract or purified translation system.

Embodiment 51

The method of embodiment 50, wherein the ribosome-depleted cellular extract comprises an S150 extract prepared from mid- to late-exponential growth phase cell cultures or cultures having an O.D.600~3.0 at time of harvest.

Embodiment 52

The method of embodiment 48, wherein the sequence defined polymer is prepared in vivo.

Embodiment 53

The method of embodiment 48 or 52, wherein the sequence defined polymer is prepared in the cell of any of embodiments 46 or 47.

Embodiment 54

The method of any of embodiments 48-53, wherein the mRNA or DNA encodes a modified Shine-Dalgarno sequence and the engineered ribosome comprises an anti-Shine-Dalgarno sequence complementary and/or cognate to the modified Shine-Dalgarno sequence, optionally wherein the anti-Shine-Dalgarno sequence and/or the complementary and/or cognate Shine-Dalgarno sequence comprise a polynucleotide of FIG. 21.

Embodiment 55

The method of any of embodiments 48-54, wherein the sequence-defined polymer comprises an amino acid.

Embodiment 56

The method of embodiment 55, wherein the amino acid is a natural amino acid.

Embodiment 57

The method of embodiment 55, wherein the amino acid is an unnatural amino acid.

EXAMPLES

The following Examples are illustrative and should not be interpreted to limit the claimed subject matter.

Example 1—Protein Synthesis by Ribosomes with Tethered Subunits

Reference is made to International Published Application WO 2015/184283, "Tethered Ribosomes and Methods of Making and Using Thereof," and Orelle et al., "Protein synthesis by ribosomes with tethered subunits," Nature, 6 Aug. 2015, Vol. 524, page 119, the contents of which are incorporated herein by reference in their entireties.

Viable Variants of Permuted Large Subunits

A comprehensive collection of 91 cp23S rDNA mutants with new ends placed at nearly every 23S rRNA hairpin was prepared (FIG. 1A). The CP23S sequences were introduced in place of the wild-type 23S gene of pAM552 plasmid (FIG. 3) and the resulting constructs were transformed in the E. coli SQ171 cells lacking chromosomal rRNA alleles [Asai 1999]. Twenty-two constructs were able to replace the resident plasmid pCSacB carrying wild-type rRNA operon. Most of the viable CP variants had new 23S rRNA ends at the subunit solvent side, including several locations close to the interface rim. Table 1 characterizes the growth of E. coli SQ171 cells pressing a pure population of ribosomes with circularly permuted 23S rRNA.

TABLE 1

Characterization of the growth of E. coli SQ171 cells expressing a pure population of ribosomes with circularly permuted 23S rRNA

| | Doubling time (min)[a] | | Cell Density ($OD_{600}$) at saturation[b] | | n[f] |
|---|---|---|---|---|---|
| | 30° C. | 30° C. | 30° C. | 30° C. | |
| pAM552[c] | 61.0 ± 3.2 | 53.9 ± 1.0 | 1.04 ± 0.06 | 0.93 ± 0.03 | 4 |
| pAM552-AflII[d] | 67.4 ± 1.0 | 53.3 ± 2.4 | 1.07 ± 0.01 | 0.97 ± 0.00 | 4 |
| CP67[e] | 106.4 ± 5.4 | 69.6 ± 2.1 | 0.83 ± 0.05 | 0.41 ± 0.07 | 3 |
| CP95 | 144.9 ± 35.9 | 82.4 ± 24.4 | 0.66 ± 0.31 | 0.51 ± 0.18 | 6 |
| CP104 | 90.8 ± 10.3 | 52.7 ± 3.2 | 0.98 ± 0.03 | 0.95 ± 0.02 | 3 |
| CP168 | 123.8 ± 27.9 | 57.7 ± 1.9 | 0.70 ± 0.22 | 0.88 ± 0.12 | 10 |
| CP281 | 100.1 ± 11.0 | 54.6 ± 10.1 | 1.01 ± 0.04 | 0.93 ± 0.13 | 3 |
| CP549 | 101.7 ± 18.2 | 46.5 ± 3.9 | 1.00 ± 0.02 | 0.98 ± 0.03 | 3 |
| CP617 | 231.7 ± 20.5 | 91.5 ± 18.5 | 0.16 ± 0.03 | 0.85 ± 0.05 | 4 |
| CP634 | 162.0 ± 34.2 | 212.5 ± 58.1 | 0.46 ± 0.19 | 0.50 ± 0.10 | 3 |
| CP879 | 106.6 ± 4.7 | 51.4 ± 4.6 | 1.03 ± 0.02 | 0.99 ± 0.04 | 3 |
| CP891 | 144.5 ± 41.8 | 60.7 ± 4.1 | 0.56 ± 0.43 | 0.76 ± 0.23 | 6 |
| CP1112 | 89.6 ± 6.0 | 57.8 ± 12.2 | 0.96 ± 0.02 | 0.91 ± 0.12 | 3 |
| CP1178 | 102.5 ± 11.0 | 46.2 ± 1.3 | 0.96 ± 0.02 | 0.99 ± 0.01 | 3 |
| CP1498 | 167.5 ± 17.5 | 118.0 ± 17.1 | 0.56 ± 0.32 | 0.52 ± 0.19 | 3 |
| CP1511 | 131.5 ± 4.2 | 76.7 ± 1.5 | 0.88 ± 0.01 | 0.88 ± 0.01 | 3 |
| CP1587 | 98.1 ± 12.4 | 55.1 ± 6.6 | 0.93 ± 0.05 | 0.92 ± 0.08 | 3 |
| CP1716 | 174.4 ± 31.9 | 117.8 ± 16.5 | 0.44 ± 0.16 | 0.62 ± 0.34 | 3 |
| CP1733 | 117.3 ± 8.2 | 83.8 ± 2.2 | 0.95 ± 0.01 | 0.80 ± 0.01 | 3 |
| CP1741 | 230.0 ± 14.7 | 269.0 ± 50.3 | 0.28 ± 0.00 | 0.66 ± 0.09 | 3 |
| CP1873 | 108.4 ± 6.5 | 52.9 ± 0.8 | 0.94 ± 0.01 | 0.91 ± 0.01 | 3 |
| CP2148 | 83.0 ± 2.9 | 52.4 ± 3.9 | 0.73 ± 0.09 | 0.82 ± 0.02 | 4 |
| CP2800 | 85.9 ± 15.7 | 53.5 ± 9.7 | 1.04 ± 0.03 | 0.91 ± 0.12 | 3 |
| CP2861 | 138.4 ± 10.7 | 93.7 ± 4.5 | 0.88 ± 0.00 | 0.83 ± 0.04 | 3 |

[a]Growth in 100 μL LB media supplemented with 50 μg/ml carbenicillin in 96-well plate with shaking.
[b]After 18 hours of growth.
[c]pAM552: wild type rrnB operon.
[d]pAM552-AflII: rrnB operon with the 23S rRNA mutations G2C and C2901G used to introduce the AflII restriction sites.
[e]CPx: rrnB with 23S circular permutations and G2C/C2901G mutations; x indicates the 5' starting nucleotide of the circularly permuted 23S gene, n: number of individual colonies used for growth analysis.
[f]Biological replicates are indicated in the "n" column, which is number of separate colonies that were used for each number average and standard deviation.

One of the viable mutants (CP2861) had 23S rRNA ends within the loop of helix 101 (11101), near the apex loop of the 16S rRNA helix 44 (h44) (FIG. 1A). Since h44 length varies among different species and its terminal loop sequence can tolerate significant alterations [Dorywalska 2005], h44 was a promising site for grafting the CP2861 23S rRNA and generating a hybrid 16S-23S rRNA molecule (FIG. 2A). In the chimeric rRNA, the processing sequences flanking the mature 16S rRNA would remain intact for proper maturation of the 16S rRNA termini, whereas endonuclease processing signals of 23S rRNA would be eliminated thereby preventing its cleavage from the hybrid molecule.

Ribosomes with Tethered Subunits can Support Protein Synthesis and Cell Growth

The RNA linkers must span the 30 Å-40 Å distance between h44 and 11101 loops and allow for ~10 Å subunit ratcheting during protein synthesis [Yusupov 2001; Voorhees 2009; Dunkle 2011; Frank 2000]. We prepared a library of constructs, pRibo-T, in which the length of two tethers, T1 connecting 16S rRNA G1453 with 23S rRNA C2858 and T2 linking 23S C2857 with 16S G1454, varied from 7 to 12 adenine residues (Table 2). Plasmid exchange in SQ171 cells yielded several very slowly growing colonies, and the pattern of extracted RNA showed a single major RNA species corresponding to the 16S-23S chimera instead of the individual 16S and 23S bands (FIG. 6A). This result suggested that translation in these cells was carried out exclusively by Ribo-T and revealed for the first time that the bipartite nature of the ribosome is dispensable for successful protein synthesis and cell viability.

TABLE 2

The results of sequencing of the oligo(A) linkers T1 and T2 in pRibo-T isolated from randomly picked POP2136 clones transformed with the linker library

| T1 | T2 | No. of clones |
|---|---|---|
| 5A | 10A | 1 |
| 7A | 9A | 1 |
| 7A | 10A | 1 |
| 7A | 11A | 1 |
| 8A | 10A | 1 |
| 9A | 9A | 1 |
| 9A | 11A | 2 |
| 9A | 12A | 1 |
| 10A | 8A | 1 |
| 10A | 10A | 2 |
| 10A | 11A | 1 |
| 11A | 9A | 1 |
| 11A | 12A | 1 |
| 12A | 8A | 1 |
| 12A | 12A | 1 |

Figure 6:
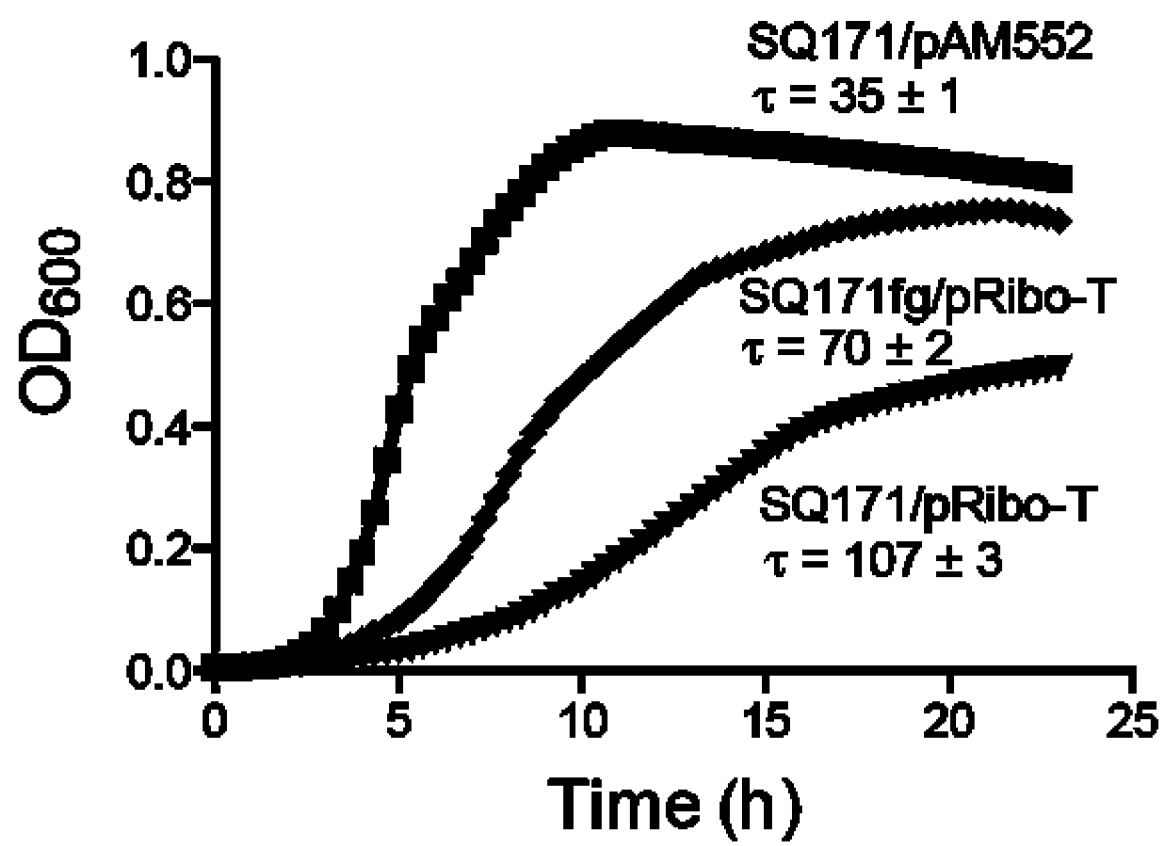
FIG. 6 shows growth curves for cells expressing wild-type or tethered ribosomes and for fast-growing mutant cells expressing tethered ribosomes.

The linker combinations 8A/9A or 9A/8A (for T1/T2) were found in the 6 best-growing clones. The first combination showed slightly better behavior in some subsequent experiments and was chosen for further investigation. In the pRibo-T plasmid the native 5' and 3' ends of the 23S rRNA were linked via a tetranucleotide sequence GAGA (connector C), and circularly permuted 23 rRNA gene, 'opened' in the apex loop of 11101, and inserted in the apex loop of 16S rRNA helix h44 via an A8 linker T1 and an A9 linker T2. The original SQ171/pRibo-T clones, although viable, grew slowly (doubling time 107±3 min compared to 35±1 min for SQ171 cells expressing wild-type ribosomes), exhibited poor recovery from the stationary phase, and low cell density at saturation (FIG. 6). By passaging cells in liquid culture for approximately 100 generations, we isolated faster growing mutants. One such clone, SQ171fg/pRibo-T (for fast growing), exhibited better growth characteristics and shorter doubling time (70±2 min) (FIG. 6). PCR and primer extension analysis showed the lack of wild-type rDNA and rRNA respectively, confirming the notion that every ribosome in this strain was assembled with the tethered rRNA. Because pRibo-T plasmid from the SQ171fg clone was unaltered, we sequenced the entire genome and found a nonsense mutation in the Leu codon 22 of the ybeX gene encoding a putative $Mg^{2+}/Co^{2+}$ transporter and a missense mutation in the codon 549 of the rpsA gene encoding ribosomal protein S1. Either one of these mutations or their combined effect must account for the faster growth of SQ171fg/pRibo-T cells (henceforth called Ribo-T cells).

Figure 5D:
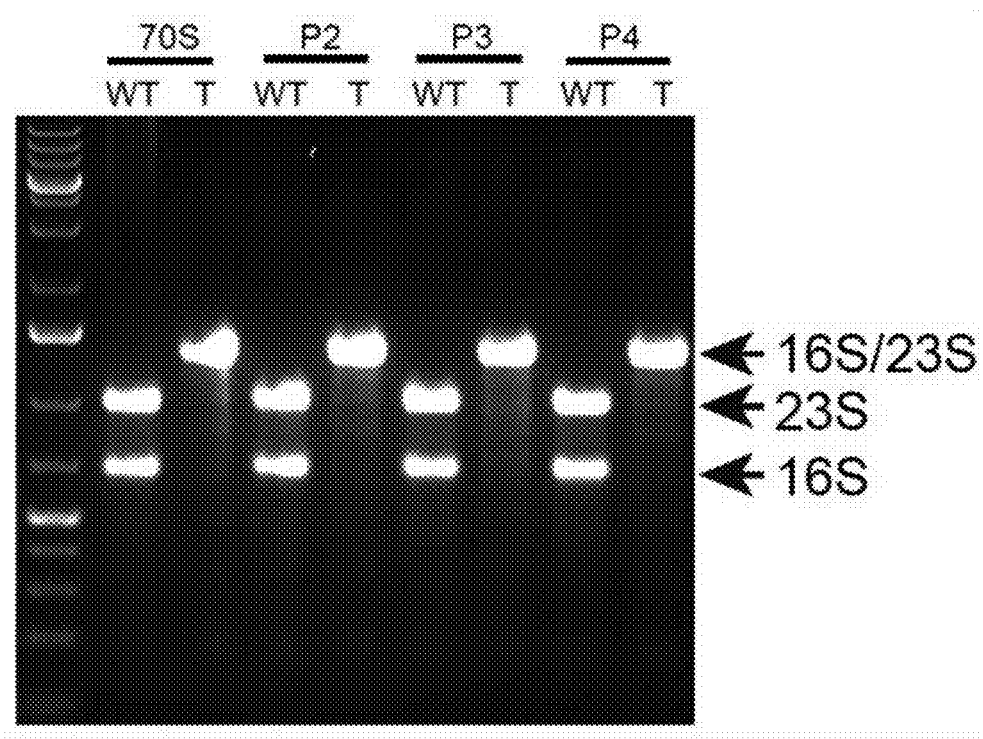
FIG. 5D shows the agarose electrophoresis analysis of RNA extracted from corresponding sucrose gradient peaks for wild-type ribosomes (WT) and Ribo-T (T).
Figure 7:
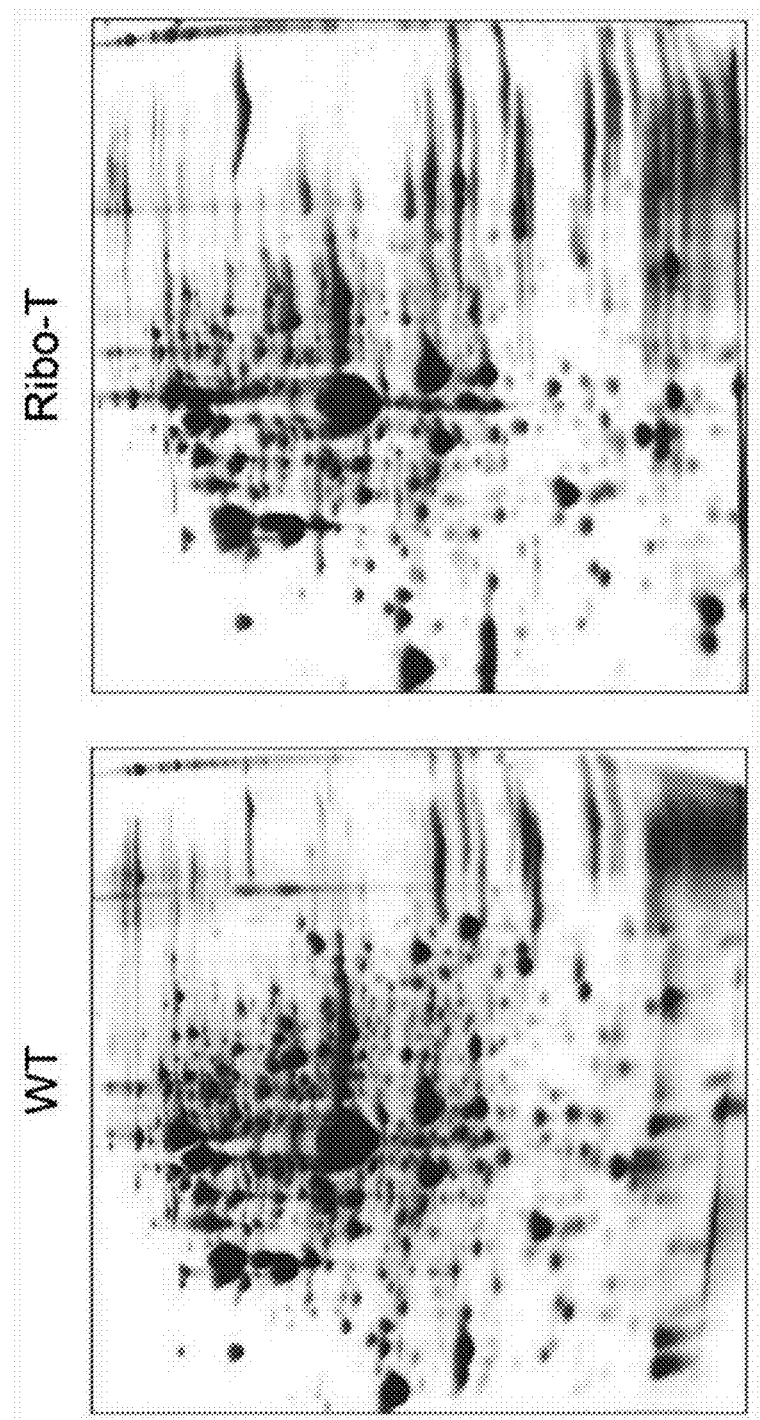
FIG. 7 shows a 2D electrophoresis analysis of cellular proteins expressed by wild type untethered ribosomes (WT) and tethered ribosomes (Ribo-T).

To firmly establish that protein synthesis in Ribo-T cells was carried out by ribosomes with tethered subunits, we carefully examined the integrity of Ribo-T rRNA. Analysis of Ribo-T preparations in a denaturing gel showed only very faint 16S and 23S-like rRNA bands possibly reflecting the linker cleavage either in the cell or during Ribo-T isolation. In most of the multiple Ribo-T preparations, these cleavage products accounted for less than 4% of the total Ribo-T rRNA. In some of the preparations, these bands were completely absent showing that more than 99% of Ribo-T remained intact. Consistently, primer extension across the T1 and T2 linkers did not show any major stops attesting to the general stability of the oligo(A) connectors. Protein synthesis rate in Ribo-T cells reached 50.5±3.5% of that in cells with wild type ribosomes and thus cannot be accounted for by a small fraction of Ribo-T with cleaved tethers. Unequivocal proof of active Ribo-T translation in vivo came from analysis of polysomes prepared from Ribo-T cells, where intact 16S-23S hybrid rRNA (rather than the products of its cleavage) was associated with the heavy polysomal fractions (FIGS. 5B-D). This result provided clear evidence that intact Ribo-T composed of covalently-linked subunits is responsible for protein synthesis in the Ribo-T cells. 2D-gel analysis showed that the absolute majority of the proteins present in SQ171 cells that express wild-type ribosomes are efficiently synthesized in the Ribo-T cells (FIG. 7).

Compositions and Properties of Ribo-T

We isolated ribosomes with tethered subunits from Ribo-T cells and characterized their composition and properties. The tethered ribosome contains an apparently equimolar amount of 5S rRNA and the full complement of ribosomal proteins in quantities closely matching the composition of wild-type ribosome (FIGS. 8A, B). Chemical probing showed that the rRNA hairpins h44 and H101 remain largely unperturbed, while both linkers were highly accessible to chemical modification, indicating that they are solvent-exposed.

Sucrose gradient analysis of Ribo-T showed that at 15 mM $Mg^{2+}$ the majority of the ribosomal material sedimented as a 70S peak with a minor faster-sedimenting peak likely representing Ribo-T dimers due to crossRibosome subunit association at a high $Mg^{2+}$ concentration (FIG. 9). At lower $Mg^{2+}$ concentration (1.5 mM), when the native ribosome completely dissociates into subunits, Ribo-T still sediments as a single peak with an apparent sedimentation velocity of 65S (FIG. 9). The distinctive resistance of Ribo-T to subunit dissociation offers a venue for isolating Ribo-T if it is expressed in cells concomitantly with wild type ribosomes.

Ribo-T Functions in Cell-Free Protein Synthesis

We tested the activity of Ribo-T in the PURExpress in vitro translation system [Shimizu 2001] lacking native ribosomes. Ribo-T efficiently synthesized the 18 kDa dihydrofolate reductase (DHFR) (FIG. 10A). By following the kinetics of accumulation of the functional 27 kDa super folder green fluorescence protein (sf-GFP) [Pedelacq 2006], we calculated that the rate of Ribo-T-catalyzed protein synthesis reaches ca. 45% of that of the wild-type ribosomes (FIG. 10B). To assess which translation step is the most problematic for Ribo-T, progression of Ribo-T through a short synthetic gene [Orelle 2013] was analyzed by toe-printing. A more pronounced band of the ribosomes at the ORF start codon indicated that Ribo-T is somewhat impaired in translation initiation at a step subsequent to the start codon recognition. Similarly slow initiation was observed during in vitro translation of several other genes. Because increasing the concentration of initiation factors could not rescue the initiation defect, it is unlikely to stem from a lower affinity of the factors for Ribo-T.

Orthogonal Ribo-T Translates an Orthogonal Reporter In Vivo and In Vitro

Figure 11A:
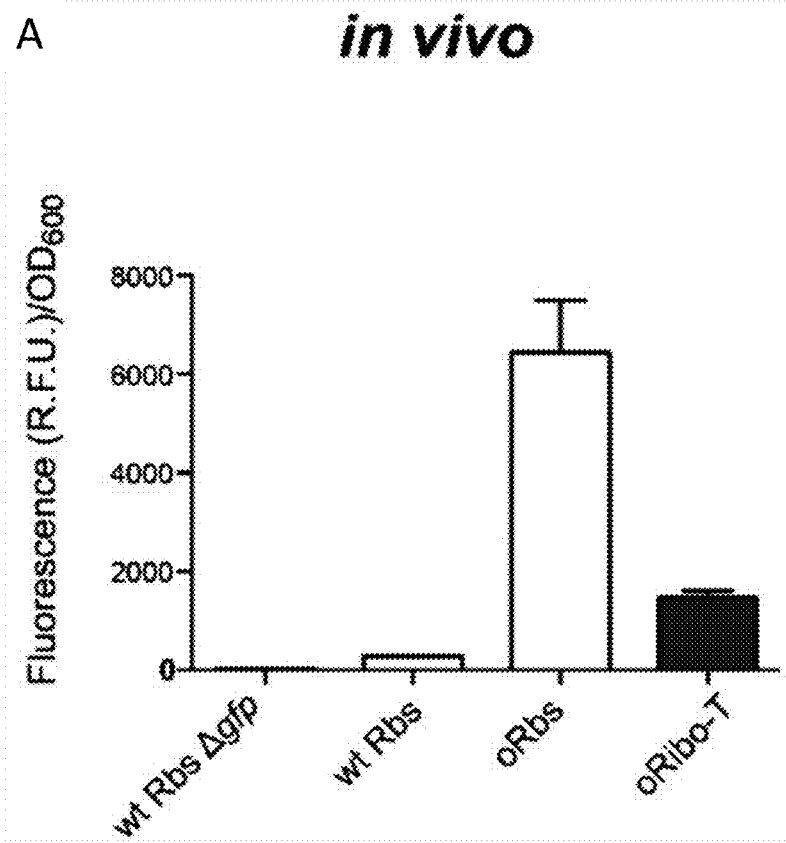
FIG. 11A shows in vivo translation of the orthogonal sf-gfp reporter by untethered ribosomes with corresponding orthogonal small subunits (oRbs) and tethered ribosomes with corresponding orthogonal small subunits (oRibo-T).

To enable a fully orthogonal ribosome system, we next engineered a Ribo-T version (oRibo-T) committed to translation of a particular orthogonal cellular mRNA. The wild-type 16S anti-SD region was altered from ACCUCCUUA to AUUGUGGUA [Rackham 2005] producing a poRibo-T1 construct. When poRibo-T1 was introduced in *E. coli* carrying the sf-gfp gene with the SD sequence CACCAC cognate to oRibo-T, notable sfGFP expression was observed (FIG. 11A), demonstrating the activity of oRibo-T.

Ribosome preparation from poRibo-T1 transformed cells (containing a mixture of wild-type ribosomes and oRibo-T) translated an orthogonal sf-gfp gene in a cell-free system (FIG. 11B). However, because the orthogonal sf-gfp transcript is the only mRNA available during in vitro translation and no native mRNA engage wild-type 30S subunits, a fraction of orthogonal sf-gfp translation is accounted for by wild-type ribosomes (FIG. 11B). Therefore, to isolate oRibo-T1 activity in vitro, we used the A2058G mutation in the 23S rRNA portion of oRibo-T, which rendered ribosomes resistant to macrolide (e.g., erythromycin) and lincosamide (e.g., clindamycin) antibiotics. Addition of clindamycin to the reaction with wild-type ribosomes completely inhibited expression of the reporter (FIG. 11B), whereas significant expression of GFP was observed in the reaction carrying the oRibo-T preparation (FIG. 11B), fully attributable to the in vitro activity of the engineered orthogonal ribosome.

Selective inhibition of the wild-type ribosomes in the oRibo-T preparation could be a useful tool for in vitro applications. Importantly, the unique nature of Ribo-T allows for utilizing antibiotic resistance mutations in any of the ribosomal subunits. We demonstrated this by introducing a G693A mutation in the small subunit moiety of oRibo-T, rendering oRibo-T resistant to pactamycin [Mankin 1997; Orelle 2013]. Pactamycin (100 µM) completely inhibited the activity of the wild-type ribosomes in the PURE translation system, whereas oRibo-T (G693A) remained fully active (FIG. 11C). The combination of an orthogonal translation initiation signal with the antibiotic resistance mutations embedded in oRibo-T allows for exploring unique properties of oRibo-T in cell-free system even in preparations carrying a substantial fraction of wild-type ribosomes.

The Evolvability of oRibo-T

We next used the oRibo-T system to search for gain-of Function mutations in the PTC, which could facilitate translation of a problematic protein sequence by the ribosome. Such experiments would require highly efficient transformation of the recipient cells with poRibo-T constructs. We noted, however, that in contrast to the selected SQ171fg cells, transformation of several *E. coli* strains (e.g. JM109, BL21 or C41 26) with poRibo-T1 was rather poor and resulted in slowly growing colonies, which varied significantly in size. Fortuitously, in the course of these experiments we isolated a spontaneous mutant plasmid, poRibo-T2, which showed notably improved transformation efficiency and produced evenly-sized colonies which appeared on the plate after an overnight incubation (as opposed to a 36 hr incubation for the poRibo-T1 transformants). Sequencing showed that poRibo-T2 acquired a single mutation in the PL promoter that controls Ribo-T expression, which altered its '-10' box from GATACT to TATACT bringing it closer to the TATAAT consensus. Although we do not fully understand why the promoter mutation improves performance of poRibo-T (as well as of non-orthogonal pRibo-T) in the 'unselected' *E. coli* cells, all the subsequent in vivo experiments were carried out using the poRibo-T2-derived constructs.

Figure 12:
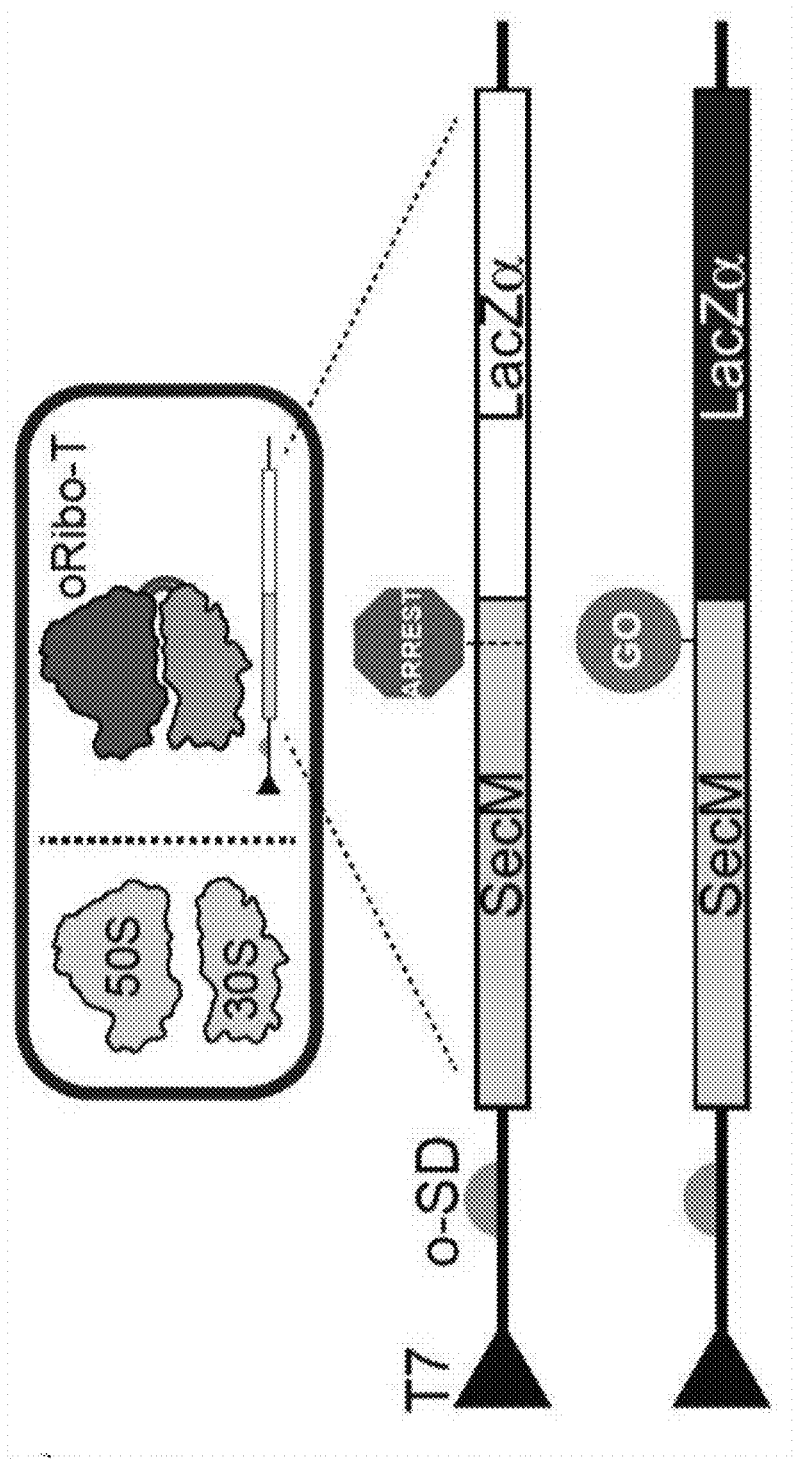
FIG. 12 shows an orthogonal secM-LacZα reporter gene.

Translation of the secM gene, which regulates the expression of the essential SecA ATPase involved in protein secretion, is controlled by nascent peptide-dependent translation arrest. The ribosome stalls when it reaches the Pro166 codon of secM because specific interactions of the SecM nascent chain with the ribosomal exit tunnel impair the PTC function preventing the transfer of the 165-amino acid long peptide to the incoming Pro-tRNA 27-29. Thus, the SecM polypeptide represents a classic example of an amino acid sequence whose translation is problematic for the ribosome. Several mutations in the ribosomal exit tunnel (e.g., A2058G) have been previously identified as relieving translation arrest possibly by disrupting the nascent chainRibosome interactions [Nakatogawa 2002; Cruz-Vera 2005; Vazquez-Laslop 2010]. However, exploring the role of the PTC in the mechanism of the translation arrest and identifying the catalytic center mutations alleviating ribosome stalling during SecM translation has been impossible so far because of the lethal nature of the mutations in the PTC active site [Thompson 2001; Sato 2006]. To search for the translation arrest bypass mutations in the PTC, we removed the A2058G mutation from poRibo-T2 and engineered an orthogonal SecM-based reporter, poSML. In the pACYC177-based poSML, the reporter gene, equipped with an orthogonal SD sequence, includes 46 codons of secM, encoding the problematic amino acid sequence, fused in frame in front of the lacZα gene [Nakatogawa 2002] (FIG. 12). When the reporter plasmid was introduced in the poRibo-T2 transformed C41(DE3) cells capable of α-complementation, colonies formed on the indicator plates were white, likely because SecM-induced translation arrest prevents oRibo-T from reaching the lacZα segment of the reporter mRNA.

We then engineered a library of oRibo-T mutants with alterations in rRNA residues in the PTC A site since it has been proposed to play a key role in the mechanism of ribosome stalling [Ramu 2011; Gong 2002; Muto 2006; Arenz 2014]. In addition, the ability to manipulate the ribosomal A-site could be crucial for future efforts to engineer ribosomes capable of programmed polymerization of unnatural amino acids and backbone-modified analogs. Two splayed-out residues, A2451 and C2452, whose mutations are dominantly lethal in *E. coli* [Thompson 2001; Sato 2006], form the pocket that accommodates the amino acid side chain of the A site-bound aminoacyl-tRNA. Thus, the poRibo-T2 library we prepared contained each of the 16 possible dinucleotide combinations at positions 2451-2452 in the 23S rRNA segment of oRibo-T.

Figure 13A:
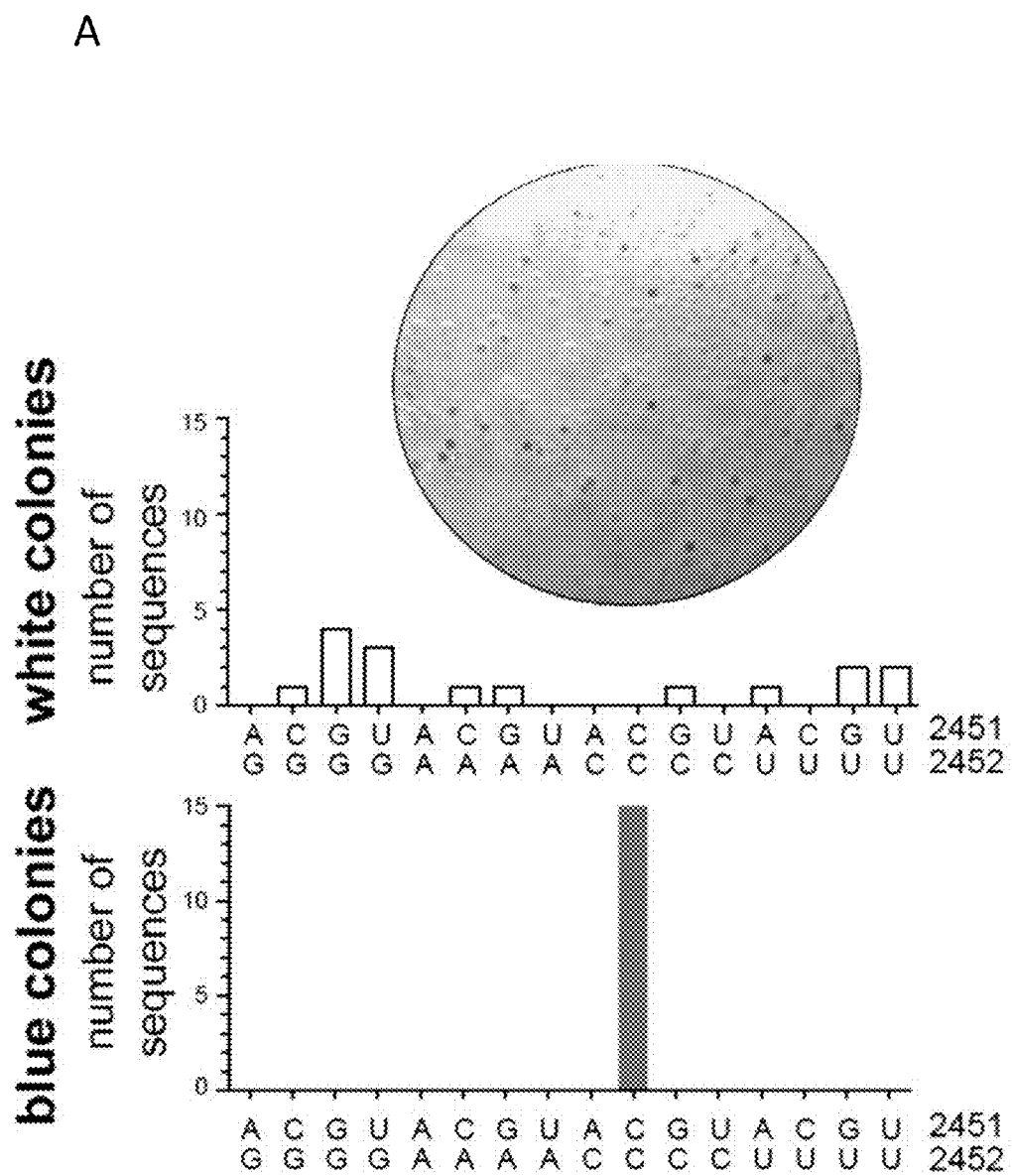
FIG. 13A shows *E. coli* cells transformed with an orthogonal sects-lacZα gene and a library of tethered ribosomes with different nucleotide combinations at the 2451 and 2452 positions of the large tethered subunit.

Strikingly, when the C41(DE3) cells with the poSML plasmid were transformed with the poRibo-T2 2451/2452 library and plated on indicator plates, some of the colonies appeared notably blue-colored (FIG. 13A). This meant that some of the oRibo-T mutants were able to bypass the SecM-induced arrest and continue active translation through the lacZα segment of the reporter. Sequencing 15 blue colonies showed that they all carried a C2451-C2452 sequence (the A2451C mutation) in the PTC. In contrast, none of the 16 analyzed 'white' colonies had this sequence and instead exhibited a variety of dinucleotide combinations at positions 2451-2452 (FIG. 13A). Because of the relatively small size of the 2451/2452 mutant library, we verified these results by introducing 16 individual poRibo-T2 plasmids with all possible 2451-2452 mutations into poSML-transformed C41(DE3) cells. Importantly, all the individual oRibo-T 2451/2452 mutants were viable confirming that oRibo-T is suitable for expression of dominantly lethal 23S rRNA mutations and indicating a low degree of cross-association of Ribo-T with free wild-type 30S subunits. Three transformants of each type were then tested on the indicator plate. Consistent with the previous result (FIG. 13A), the A2451C mutation confers the most pronounced blue color of the transformants, comparable to that seen in cells expressing oRibo-T with the tunnel mutation A2058G (FIG. 13B). The A2451U mutation also increased the blue hue of the cells although to a lesser extent. Our results suggested that the A2451C (and A2451U) mutants were not only functional in cellular protein synthesis but in addition gained the ability to bypass translation arrest caused by the problematic SecM sequence. Interestingly, a mutation of another essential nucleotide in the PTC (U2585G), which has been proposed to be implicated in some translation arrest scenarios [Arnez 2014] showed no effect on SecM arrest. We verified the discovered role of A2451 in the mechanism of SecM translation arrest by testing the expression of the orthogonal secM-lacZ reporter in vitro by isolated wild-type or A2451C mutant oRibo-T. In order to assure that the in vitro effects are attributed exclusively to oRibo-T, a pactamycin resistance mutation G693A was introduced in the 16S segment of oRibo-T constructs and cell-free translation in the PURE system was carried out in the presence of pactamycin. Under our experimental conditions, only a small fraction of original oRibo-T were able to bypass the SecM arrest signal and synthesize the full-size hybrid protein (FIG. 4E, lane oRibo-T(A2451). In contrast the A2451C mutant was able to bypass the SecM arrest site twice as efficiently as the unmodified oRibo-T (FIG. 13C), confirming that the selected (and otherwise lethal) mutation has altered the functional properties of the PTC and improved the ability of oRibo-T to polymerize a polypeptide sequence problematic for wild-type ribosome.

Preparation of Circularly Permuted Variants of the 23S rRNA

The A2058G mutation was introduced into the pAM552 plasmid by inverse PCR using primers CCGTCTTGC-CGCGGGTAC (SEQ ID NO: 1) and (SEQ ID NO: 2)
<u>GTGTACCCGCGGCAAGACGG</u>*G*AAGACCCCGTGAACC sequence is complementary to the second primer and the mutation is shown by italicized bold character) followed by re-circularization by Gibson assembly reaction [Gibson 2009] (all primers used in this study were synthesized by Integrated DNA Technology). A 23S-A2058G gene with native 5' and 3' ends linked by a GAGA tetra-loop was generated by inverse PCR using primers GGTTAAGCCT-CACGGTTC (SEQ ID NO: 3) and (SEQ ID NO: 4)
CCGTGAGGCTTAACCGAGAGGTTAAGCGACTAAGCGTAC tetra loop in bold) and pAM552-A2058G as template. Purified PCR product (50 ng) was circularized by Gibson assembly reaction for 1 hour at 50° C. The resulting circular 23S rRNA gene was then cloned at its native unique EagI restriction site (position 1905 in wild-type 23S rRNA gene) into T7FLAG-4 plasmid (Sigma Aldrich) as follows. The circularized 23S rRNA gene was amplified by inverse PCR using primers (SEQ ID NO: 5)
GAGACACAACGTGGCTTTCCGGCCGTAACTATAACG
and (SEQ ID NO: 6)
CACTCGTCGAGATCGATCTTCGGCCGCCGTTTACC (added homology to the T7FLAG™-4 vector underlined) and Gibson-assembled with the T7FLAG™-4 vector amplified with the primers AAGATCGATCTCGACGAGTG (SEQ ID NO: 7) and GAAAGCCACGTTGTGTCTC (SEQ ID NO: 8). The cloned circularly permuted 23S rRNA gene in the resulting plasmid pCP23S-EagI containing a pBR322 origin of replication and KanR selective marker was fully sequenced.

The pCP23S-EagI plasmid was then digested with EagI (New England Biolabs) for 1 hour at 37° C., and the CP 23S rRNA gene was isolated from a SYBRSafe-stained 0.7% agarose gel using an E.Z.N.A. Gel Extraction kit (Omega). The 23S rRNA was circularized by T4 DNA ligase (New England Biolabs) in a 50 µl reaction with 2.5 ng/µl DNA for 14 Ms at 16° C., followed by heat inactivation at 65° C. for 10 minutes. The reaction was diluted 1:100 for use as a template in the PCR reactions for generating the circular permutants.

Ninety-one CP23S mutants were designed by introducing new 23S rRNA 5' and 3' ends at most of the apex loops and some internal loops of rRNA helices in order to assure spatial proximity of the new rRNA termini in the fully assembled 50S ribosomal subunit. Each CP23S rRNA gene was PCR-amplified in a 40 µl reaction using Phusion High Fidelity DNA polymerase (New England Biolabs) with primer pairs SEQ. ID NOS: 9-190 (Table 3) and 4 µl of the 1:100 diluted 23S circular ligation reaction as template. Each primer pair adds to the 5' and 3' ends of the amplified CP23S gene 20 bp of homology to the 23S rRNA processing stem retained in the target vector pAM552-Δ235-AflII (described below). PCR reactions catalyzed by the Phusion High Fidelity DNA polymerase were run under the following conditions: 98° C., 10 min followed by 25 cycles (98° C., 30 sec; 60° C., 30 sec; 72° C., 180 sec), followed by the final incubation for 15 min at 72° C. The reaction product was purified using E.Z.N.A. Cycle Pure kit (Omega) and the size of the amplified DNA was confirmed by electrophoresis in a 1% agarose gel. For CPs with off target bands (12 CPs total), the PCR product of the correct size was extracted from the agarose gel.

TABLE 3

| Primer pairs used for construction of circularly permuted 23S rRNA genes. | | |
|---|---|---|
| Primer[a] | Primer sequence[b] | SEQ ID NO |
| 67_60F | AACATCTTCGGGTTGTGAGcTTAAGCTGCGATAAGCGTCG | 9 |
| 67_60R | ACAGCTTCGGCGTTGTAAGCTTAAGCCACGTCCTTCATCG | 10 |
| 95_87F | AACATCTTCGGGTTGTGAGcTTAAGCACCGTTATAACCGGCGATTTC | 11 |
| 95_87R | ACAGCTTCGGCGTTGTAAGCTTAAGCACCTTACCGACGCTTATC | 12 |
| 104_97F | AACATCTTCGGGTTGTGAGcTTAAGCACCGGCGATTTCCG | 13 |
| 104_97R | ACAGCTTCGGCGTTGTAAGCTTAAGCGGTTCATATCACCTTACC | 14 |
| 128_123F | AACATCTTCGGGTTGTGAGcTTAAGCCCCAGTGTGTTTCGAC | 15 |
| 128_123R | ACAGCTTCGGCGTTGTAAGCTTAAGCCCCATTCGGAAATCG | 16 |
| 142_137F | AACATCTTCGGGTTGTGAGcTTAAGCACACACTATCATTAACTGAATC | 17 |
| 142_137R | ACAGCTTCGGCGTTGTAAGCTTAAGCACACACTGGGTTTCC | 18 |
| 168_158F | AACATCTTCGGGTTGTGAGcTTAAGCGGTTAATGAGGCGAAC | 19 |
| 168_158R | ACAGCTTCGGCGTTGTAAGCTTAAGCAGTTAATGATAGTGTGTC | 20 |
| 200_195F | AACATCTTCGGGTTGTGAGcTTAAGCTCTAAGTACCCCGAGG | 21 |
| 200_195R | ACAGCTTCGGCGTTGTAAGCTTAAGCTCAGTTCCCCCGGTTC | 22 |
| 230_225F | AACATCTTCGGGTTGTGAGcTTAAGCGAGATTCCCCCAGTAG | 23 |
| 230_225R | ACAGCTTCGGCGTTGTAAGCTTAAGCGATTTCTTTTCCTCGGGGTAC | 24 |

TABLE 3-continued

Primer pairs used for construction of circularly permuted 23S rRNA genes.

| Primer[a] | Primer sequence[b] | SEQ ID NO |
|---|---|---|
| 252_246F | AACATCTTCGGGTTGTGAGcTTAAGCGCGAACGGGGAGCAG | 25 |
| 252_246R | ACAGCTTCGGCGTTGTAAGcTTAAGCGCTACTGGGGAATCTC | 26 |
| 281_274F | AACATCTTCGGGTTGTGAGcTTAAGCCAGTGTGTGTTAGTG | 27 |
| 281_274R | ACAGCTTCGGCGTTGTAAGcTTAAGCGCTCTGGGCTGCTC | 28 |
| 312_305F | AACATCTTCGGGTTGTGAGcTTAAGCGGCGCGCGATACAG | 29 |
| 312_305R | ACAGCTTCGGCGTTGTAAGcTTAAGCGACGCTTCCACTAACAC | 30 |
| 335_327F | AACATCTTCGGGTTGTGAGcTTAAGCCCCGTACACAAAAATGCAC | 31 |
| 335_327R | ACAGCTTCGGCGTTGTAAGcTTAAGCCCCTGTATCGCGCGCCTTTC | 32 |
| 347_343F | AACATCTTCGGGTTGTGAGcTTAAGCAATGCACATGCTGTGAG | 33 |
| 347_343R | ACAGCTTCGGCGTTGTAAGcTTAAGCGTGTACGGGGCTGTC | 34 |
| 391_383F | AACATCTTCGGGTTGTGAGcTTAAGCATCCTGTCTGAATATGG | 35 |
| 391_383R | ACAGCTTCGGCGTTGTAAGcTTAAGCGTCCCGCCCTACTC | 36 |
| 416_411F | AACATCTTCGGGTTGTGAGcTTAAGCTCCTCCAAGGCTAAATAC | 37 |
| 416_411R | ACAGCTTCGGCGTTGTAAGcTTAAGCCCCCCCATATTCAGACAG | 38 |
| 467_462F | AACATCTTCGGGTTGTGAGcTTAAGCGGGAAAGGCGAAAAGAAC | 39 |
| 467_462R | ACAGCTTCGGCGTTGTAAGcTTAAGCGGTACTGGTTCACTATCG | 40 |
| 493_487F | AACATCTTCGGGTTGTGAGcTTAAGCGGGGAGTGAAAAAGAAC | 41 |
| 493_487R | ACAGCTTCGGCGTTGTAAGcTTAAGCGGGGTTCTTTTCGCCTTTC | 42 |
| 502_497F | AACATCTTCGGGTTGTGAGcTTAAGCAAAAGAACCTGAAACCGTG | 43 |
| 502_497R | ACAGCTTCGGCGTTGTAAGcTTAAGCTCCCCTCGCCGGGGTTC | 44 |
| 549_544F | AACATCTTCGGGTTGTGAGcTTAAGCGCGTGTGACTGCGTACC | 45 |
| 549_544R | ACAGCTTCGGCGTTGTAAGcTTAAGCGCGTGCTCCCACTG | 46 |
| 617_611F | AACATCTTCGGGTTGTGAGcTTAAGCGGGGAGCCGAAGG | 47 |
| 617_611R | ACAGCTTCGGCGTTGTAAGcTTAAGCGGTTAACCTTGCTACAG | 48 |
| 634_629F | AACATCTTCGGGTTGTGAGcTTAAGCCCGAGTCTTAACTGG | 49 |
| 634_629R | ACAGCTTCGGCGTTGTAAGcTTAAGCCCTTCGGCTCCCCTATTC | 50 |
| 647_641F | AACATCTTCGGGTTGTGAGcTTAAGCGGGCGTTAAGTTGCAGG | 51 |
| 647_641R | ACAGCTTCGGCGTTGTAAGcTTAAGCAGACTCGTTTCCCTTC | 52 |
| 719_712F | AACATCTTCGGGTTGTGAGcTTAAGCCTAACTGGAGGACC | 53 |
| 719_712R | ACAGCTTCGGCGTTGTAAGcTTAAGCCCAACCTTCAACCTG | 54 |
| 753_744F | AACATCTTCGGGTTGTGAGcTTAAGCATTAGCGGATGACTTGTG | 55 |
| 753_744R | ACAGCTTCGGCGTTGTAAGcTTAAGCATTAGTCGGTCGGTCC | 56 |
| 785_779F | AACATCTTCGGGTTGTGAGcTTAAGCGCCAATCAAACCGGGAG | 57 |
| 785_779R | ACAGCTTCGGCGTTGTAAGcTTAAGCACCCCCAGCCACAAG | 58 |

TABLE 3-continued

Primer pairs used for construction of circularly permuted 23S rRNA genes.

| Primer[a] | Primer sequence[b] | SEQ ID NO |
|---|---|---|
| 831_826F | AACATCTTCGGGTTGTGAGcTTAAGCGTAGCGCCTCGTGAATTC | 59 |
| 831_826R | ACAGCTTCGGCGTTGTAAGcTTAAGCATAGCTTTCGGGGAGAACC | 60 |
| 879_875F | AACATCTTCGGGTTGTGAGcTTAAGCGGGGGTCATCCCGAC | 61 |
| 879_875R | ACAGCTTCGGCGTTGTAAGcTTAAGCCCGAAACAGTGCTCTACC | 62 |
| 891_885F | AACATCTTCGGGTTGTGAGcTTAAGCGACTTACCAACCCGATG | 63 |
| 891_885R | ACAGCTTCGGCGTTGTAAGcTTAAGCGACCCCCTTGCCGAAAC | 64 |
| 962_955F | AACATCTTCGGGTTGTGAGcTTAAGCGTCCGTCGTGAAGAGG | 65 |
| 962_955R | ACAGCTTCGGCGTTGTAAGcTTAAGCACCCGCCGTGTGTC | 66 |
| 985_978F | AACATCTTCGGGTTGTGAGcTTAAGCCCCAGACCGCCAGC | 67 |
| 985_978R | ACAGCTTCGGCGTTGTAAGcTTAAGCCCCTCTTCACGACGGAC | 68 |
| 1011_1004F | AACATCTTCGGGTTGTGAGcTTAAGCGTCATGGTTAAGTGGGAAAC | 69 |
| 1011_1004R | ACAGCTTCGGCGTTGTAAGcTTAAGCACCTTAGCTGGCGGTC | 70 |
| 1051_1043F | AACATCTTCGGGTTGTGAGcTTAAGCGCCAGGATGTTGGCTTAG | 71 |
| 1051_1043R | ACAGCTTCGGCGTTGTAAGcTTAAGCGCCTTCCCACATCGTTTC | 72 |
| 1074_1064F | AACATCTTCGGGTTGTGAGcTTAAGCGCCATCATTTAAAGAAAGC | 73 |
| 1074_1064R | ACAGCTTCGGCGTTGTAAGcTTAAGCGCCAACATCCTGGCTG | 74 |
| 1086_1082F | AACATCTTCGGGTTGTGAGcTTAAGCAGAAAGCGTAATAGCTCAC | 75 |
| 1086_1082R | ACAGCTTCGGCGTTGTAAGcTTAAGCAATGATGGCTGCTTCTAAG | 76 |
| 1099_1092F | AACATCTTCGGGTTGTGAGcTTAAGCGCTCACTGGTCGAG | 77 |
| 1099_1092R | ACAGCTTCGGCGTTGTAAGcTTAAGCGCTTTCTTTAAATGATGGCTG | 78 |
| 1112_1108F | AACATCTTCGGGTTGTGAGcTTAAGCGTCGGCCTGCGCGGAAG | 79 |
| 1112_1108R | ACAGCTTCGGCGTTGTAAGcTTAAGCACCAGTGAGCTATTACGCTTTC | 80 |
| 1177_1172F | AACATCTTCGGGTTGTGAGcTTAAGCGCGTTGTTGGGTAGG | 81 |
| 1177_1172R | ACAGCTTCGGCGTTGTAAGcTTAAGCGCGTCGCTGCC | 82 |
| 1215_1208F | AACATCTTCGGGTTGTGAGcTTAAGCGGTGTGCTGTGAGG | 83 |
| 1215_1208R | ACAGCTTCGGCGTTGTAAGcTTAAGCGGCTTACAGAACGCTC | 84 |
| 1227_1222F | AACATCTTCGGGTTGTGAGcTTAAGCGGCATGCTGGAGG | 85 |
| 1227_1222R | ACAGCTTCGGCGTTGTAAGcTTAAGCAGCACACCTTCGCAG | 86 |
| 1289_1281F | AACATCTTCGGGTTGTGAGcTTAAGCCCCGCTCGCCGGAAG | 87 |
| 1289_1281R | ACAGCTTCGGCGTTGTAAGcTTAAGCCCCGCTTTATCGTTACTTATG | 88 |
| 1330_1324F | AACATCTTCGGGTTGTGAGcTTAAGCCGGGGCAGGGTG | 89 |
| 1330_1324R | ACAGCTTCGGCGTTGTAAGcTTAAGCCGTTGGACAGGAACC | 90 |

TABLE 3-continued

Primer pairs used for construction of circularly permuted 23S rRNA genes.

| Primer[a] | Primer sequence[b] | SEQ ID NO |
|---|---|---|
| 1368_1363F | AACATCTTCGGGTTGTGAGcTTAAGCGGCGTAGTCGATGG | 91 |
| 1368_1363R | ACAGCTTCGGCGTTGTAAGcTTAAGCGGCCTCGCCTTAGG | 92 |
| 1398_1389F | AACATCTTCGGGTTGTGAGcTTAAGCCCTGTACTTGGTGTTAC | 93 |
| 1398_1389R | ACAGCTTCGGCGTTGTAAGcTTAAGCCCTGTTTCCCATCGAC | 94 |
| 1420_1417F | AACATCTTCGGGTTGTGAGcTTAAGCAGGGGGGACGGAG | 95 |
| 1420_1417R | ACAGCTTCGGCGTTGTAAGcTTAAGCGCAGTAACACCAAGTACAG | 96 |
| 1461_1450F | AACATCTTCGGGTTGTGAGcTTAAGCCCCGGTTTAAGCGTG | 97 |
| 1461_1450R | ACAGCTTCGGCGTTGTAAGcTTAAGCCCCGGCCAACATAG | 98 |
| 1478_1474F | AACATCTTCGGGTTGTGAGcTTAAGCGGCTGGTTTTCCAGG | 99 |
| 1478_1474R | ACAGCTTCGGCGTTGTAAGcTTAAGCACGCTTAAACCGGGAC | 100 |
| 1498_1492F | AACATCTTCGGGTTGTGAGcTTAAGCCCGGAAAATCAAGGCTG | 101 |
| 1498_1492R | ACAGCTTCGGCGTTGTAAGcTTAAGCCCTGGAAAACCAGCCTAC | 102 |
| 1511_1508F | AACATCTTCGGGTTGTGAGcTTAAGCGCTGAGGCGTGATG | 103 |
| 1511_1508R | ACAGCTTCGGCGTTGTAAGcTTAAGCTGATTTTCCGGATTTGC | 104 |
| 1523_1520F | AACATCTTCGGGTTGTGAGcTTAAGCTGACGAGGCACTACG | 105 |
| 1523_1520R | ACAGCTTCGGCGTTGTAAGcTTAAGCACGCCTCAGCCTTG | 106 |
| 1538_1533F | AACATCTTCGGGTTGTGAGcTTAAGCGTGCTGAAGCAACAAATG | 107 |
| 1538_1533R | ACAGCTTCGGCGTTGTAAGcTTAAGCGTGCCTCGTCATCACG | 108 |
| 1547_1543F | AACATCTTCGGGTTGTGAGcTTAAGCCAACAAATGCCCTGC | 109 |
| 1547_1543R | ACAGCTTCGGCGTTGTAAGcTTAAGCCAGCACCGTAGTGC | 110 |
| 1587_1582F | AACATCTTCGGGTTGTGAGcTTAAGCGGTAACATCAAATCGTAC | 111 |
| 1587_1582R | ACAGCTTCGGCGTTGTAAGcTTAAGCGCTTAGAGGCTTTTCC | 112 |
| 1619_1612F | AACATCTTCGGGTTGTGAGcTTAAGCGGTGGTCAGGTAGAG | 113 |
| 1619_1612R | ACAGCTTCGGCGTTGTAAGcTTAAGCGGTTTGGGGTACGATTTG | 114 |
| 1636_1630F | AACATCTTCGGGTTGTGAGcTTAAGCTACCAAGGCGCTTG | 115 |
| 1636_1630R | ACAGCTTCGGCGTTGTAAGcTTAAGCTACCTGACCACCTGTG | 116 |
| 1696_1691F | AACATCTTCGGGTTGTGAGcTTAAGCGGAGAAGGCACGCTG | 117 |
| 1696_1691R | ACAGCTTCGGCGTTGTAAGcTTAAGCGTTACGGCACCATTTTG | 118 |
| 1716_1712F | AACATCTTCGGGTTGTGAGcTTAAGCTAGGTGAGGTCCCTC | 119 |
| 1716_1712R | ACAGCTTCGGCGTTGTAAGcTTAAGCATCAGCGTGCCTTC | 120 |
| 1733_1727F | AACATCTTCGGGTTGTGAGcTTAAGCGGATGGAGCTGAAATC | 121 |
| 1733_1727R | ACAGCTTCGGCGTTGTAAGcTTAAGCGGACCTCACCTACATATC | 122 |
| 1741_1736F | AACATCTTCGGGTTGTGAGcTTAAGCCTGAAATCAGTCGAAGATAC | 123 |
| 1741_1736R | ACAGCTTCGGCGTTGTAAGcTTAAGCATCCGCGAGGGACCTC | 124 |

TABLE 3-continued

Primer pairs used for construction of circularly permuted 23S rRNA genes.

| Primer[a] | Primer sequence[b] | SEQ ID NO |
|---|---|---|
| 1756_1752F | AACATCTTCGGGTTGTGAGcTTAAGCGATACCAGCTGGCTG | 125 |
| 1756_1752R | ACAGCTTCGGCGTTGTAAGcTTAAGCGACTGATTTCAGCTCC | 126 |
| 1787_1777F | AACATCTTCGGGTTGTGAGcTTAAGCACACAGCACTGTGC | 127 |
| 1787_1777R | ACAGCTTCGGCGTTGTAAGcTTAAGCACAGTTGCAGCCAG | 128 |
| 1811_1806F | AACATCTTCGGGTTGTGAGcTTAAGCGTGGACGTATACGGTG | 129 |
| 1811_1806R | ACAGCTTCGGCGTTGTAAGcTTAAGCGTGTTTGCACAGTGC | 130 |
| 1840_1837F | AACATCTTCGGGTTGTGAGcTTAAGCGTGCCGGAAGGTTAATTG | 131 |
| 1840_1837R | ACAGCTTCGGCGTTGTAAGcTTAAGCGGCAGGCGTCACAC | 132 |
| 1849_1846F | AACATCTTCGGGTTGTGAGcTTAAGCGGTTAATTGATGGGGTTAG | 133 |
| 1849_1846R | ACAGCTTCGGCGTTGTAAGcTTAAGCCCGGCACCGGGCAG | 134 |
| 1873_1868F | AACATCTTCGGGTTGTGAGcTTAAGCGCGAAGCTCTTGATC | 135 |
| 1873_1868R | ACAGCTTCGGCGTTGTAAGcTTAAGCGCTAACCCCATCAATTAAC | 136 |
| 1919_1911F | AACATCTTCGGGTTGTGAGcTTAAGCACGGTCCTAAGGTAGC | 137 |
| 1919_1911R | ACAGCTTCGGCGTTGTAAGcTTAAGCACGGCCGCCGTTAC | 138 |
| 1931_1926F | AACATCTTCGGGTTGTGAGcTTAAGCTAGCGAAATTCCTTGTCG | 139 |
| 1931_1926R | ACAGCTTCGGCGTTGTAAGcTTAAGCAGGACCGTTATAGTTACG | 140 |
| 1956_1950F | AACATCTTCGGGTTGTGAGcTTAAGCTCCGACCTGCACG | 141 |
| 1956_1950R | ACAGCTTCGGCGTTGTAAGcTTAAGCCCCGACAAGGAATTTC | 142 |
| 1991_1988F | AACATCTTCGGGTTGTGAGcTTAAGCTGTCTCCACCCGAG | 143 |
| 1991_1988R | ACAGCTTCGGCGTTGTAAGcTTAAGCCTGGCCATCATTACG | 144 |
| 2036_2027F | AACATCTTCGGGTTGTGAGcTTAAGCCAGTGTACCCGCGGCAAG | 145 |
| 2036_2027R | ACAGCTTCGGCGTTGTAAGcTTAAGCCAGCGAGTTCAATTTCACTG | 146 |
| 2147_2144F | AACATCTTCGGGTTGTGAGcTTAAGCAGTCTGCATGGAGC | 147 |
| 2147_2144R | ACAGCTTCGGCGTTGTAAGcTTAAGCCGTCCACACTTCAAAG | 148 |
| 2148_2143F | AACATCTTCGGGTTGTGAGcTTAAGCGTCTGCATGGAGCCGAC | 149 |
| 2148_2143R | ACAGCTTCGGCGTTGTAAGcTTAAGCGTCCACACTTCAAAGCCTC | 150 |
| 2215_2209F | AACATCTTCGGGTTGTGAGcTTAAGCCGGGTTGCGGACAG | 151 |
| 2215_2209R | ACAGCTTCGGCGTTGTAAGcTTAAGCCGGGTCAACGTTAGAAC | 152 |
| 2254_2250F | AACATCTTCGGGTTGTGAGcTTAAGCCGGTCTCCTCCTAAAGAG | 153 |
| 2254_2250R | ACAGCTTCGGCGTTGTAAGcTTAAGCCAGTCAAACTACCCACC | 154 |
| 2276_2264F | AACATCTTCGGGTTGTGAGcTTAAGCGGAGGAGCACGAAGG | 155 |
| 2276_2264R | ACAGCTTCGGCGTTGTAAGcTTAAGCGGAGGAGACCGCCCCAG | 156 |
| 2312_2304F | AACATCTTCGGGTTGTGAGcTTAAGCTCAGGAGGTTAGTGC | 157 |
| 2312_2304R | ACAGCTTCGGCGTTGTAAGcTTAAGCCCAGGATTAGCCAACC | 158 |

TABLE 3-continued

Primer pairs used for construction of circularly permuted 23S rRNA genes.

| Primer[a] | Primer sequence[b] | SEQ ID NO |
|---|---|---|
| 2331_2324F | AACATCTTCGGGTTGTGAGcTTAAGCGCATAAGCCAGCTTGAC | 159 |
| 2331_2324R | ACAGCTTCGGCGTTGTAAGcTTAAGCACTAACCTCCTGATGTCC | 160 |
| 2362_2355F | AACATCTTCGGGTTGTGAGcTTAAGCCGCGAGCAGGTGC | 161 |
| 2362_2355R | ACAGCTTCGGCGTTGTAAGcTTAAGCCGCTCGCAGTCAAG | 162 |
| 2379_2374F | AACATCTTCGGGTTGTGAGcTTAAGCGCAGGTCATAGTGATCC | 163 |
| 2379_2374R | ACAGCTTCGGCGTTGTAAGcTTAAGCGCACCTGCTCGCGCCGTC | 164 |
| 2413_2404F | AACATCTTCGGGTTGTGAGcTTAAGCGGGCCATCGCTCAAC | 165 |
| 2413_2404R | ACAGCTTCGGCGTTGTAAGcTTAAGCAGAACCACCGGATC | 166 |
| 2479_2471F | AACATCTTCGGGTTGTGAGcTTAAGCTCGACGGCGGTGTTG | 167 |
| 2479_2471R | ACAGCTTCGGCGTTGTAAGcTTAAGCTCTTGGGCGGTATCAG | 168 |
| 2534_2529F | AACATCTTCGGGTTGTGAGcTTAAGCAGGTCCCAAGGGTATG | 169 |
| 2534_2529R | ACAGCTTCGGCGTTGTAAGcTTAAGCCAGCCCCAGGATGTG | 170 |
| 2557_2551F | AACATCTTCGGGTTGTGAGcTTAAGCGCCATTTAAAGTGGTACG | 171 |
| 2557_2551R | ACAGCTTCGGCGTTGTAAGcTTAAGCGCCATACCCTTGGGAC | 172 |
| 2567_2561F | AACATCTTCGGGTTGTGAGcTTAAGCGTGGTACGCGAGCTG | 173 |
| 2567_2561R | ACAGCTTCGGCGTTGTAAGcTTAAGCATGGCGAACAGCCATAC | 174 |
| 2599_2594F | AACATCTTCGGGTTGTGAGcTTAAGCGACAGTTCGGTCCCTATC | 175 |
| 2599_2594R | ACAGCTTCGGCGTTGTAAGcTTAAGCGACGTTCTAAACCCAGC | 176 |
| 2663_2658F | AACATCTTCGGGTTGTGAGcTTAAGCGGACCGGAGTGGAC | 177 |
| 2663_2658R | ACAGCTTCGGCGTTGTAAGcTTAAGCGTACTAGGAGCAGC | 178 |
| 2706_2701F | AACATCTTCGGGTTGTGAGcTTAAGCATGGCACTGCCCGGTAG | 179 |
| 2706_2701R | ACAGCTTCGGCGTTGTAAGcTTAAGCATGACAACCCGAACACC | 180 |
| 2742_2737F | AACATCTTCGGGTTGTGAGcTTAAGCGTGCTGAAAGCATCTAAG | 181 |
| 2742_2737R | ACAGCTTCGGCGTTGTAAGcTTAAGCCTCTTCCGCATTTAGCTAC | 182 |
| 2758_2746F | AACATCTTCGGGTTGTGAGcTTAAGCAGCACGAAACTTGC | 183 |
| 2758_2746R | ACAGCTTCGGCGTTGTAAGcTTAAGCAGCACTTATCTCTTCC | 184 |
| 2800_2796F | AACATCTTCGGGTTGTGAGcTTAAGCAGGGTCCTGAAGGAAC | 185 |
| 2800_2796R | ACAGCTTCGGCGTTGTAAGcTTAAGCAGGGTCAGGGAGAAC | 186 |
| 2827_2819F | AACATCTTCGGUTTGTGAGcTTAAGCCGACGTTGATAGG | 187 |
| 2827_2819R | ACAGCTTCGGCGTTGTAAGcTTAAGCCAACGTCCTTCAGG | 188 |
| 2861_2856F | AACATCTTCGGUTTGTGAGcTTAAGCTGCGTTGAGCTAAC | 189 |
| 2861_2856R | ACAGCTTCGGCGTTGTAAGcTTAAGCTGCGCTTACACAC | 190 |

[a] F: forward primer, R: reverse primer.
[b] In each primer name, the first number indicates the new 5' nucleotide for the target circular permutant, and the second number indicates the new 3' nucleotide, both in reference to the wild-type 23S rRNA nucleotide numbering scheme. Non-underlined nucleotides indicate added homology to pAM-A23S-AflII linearized backbone. Underlined nucleotides indicate primer segments that anneal to CP23S template.

To minimize PCR errors in generating the vector backbone, which carried 16S and 5S rRNA sequences, and prevent carry-through of the wild-type rrnB operon, universal backbone vector pAM552-Δ23S-AflII lacking the 23S rRNA gene and containing added AflII restriction site for cloning of CP23S was prepared. The plasmid pAM552-AflII was constructed from pAM552 by adding AflIII restriction sites within the terminal stem of the wild-type 23S rRNA gene by introducing the G2C and C2901G mutations. First the G2C mutation was introduced by inverse PCR using 5'-phosphorylated primers CTTAAGCGACTAAGCGTACAC (SEQ ID NO: 191) and CTCACAACCCGAAGATGTTTC (SEQ ID NO: 192), followed by blunt-end ligation, transformation into E. coli POP2136 electrocompetent cells, plating on LB-agar plates supplemented with 50 µg/ml carbenicillin, growth overnight at 30° C., single colony isolation and sequencing. The C2901G mutation was added by the same method using 5'-phosphorylated primers GCTTACAACGCCGAAGCTG (SEQ ID NO: 193) and TTAAGCCTCACGGTTCATTAG (SEQ ID NO: 194). The introduced mutations preserved the integrity of the 23S rRNA terminal stem and did not affect growth of SQ171 cells expressing only ribosomes with the pAM552-AflII-encoded rRNA (growth rates 53.9±1.0 min for SQ171 cells transformed with pAM552 and 53.3±2.4 min for SQ171 transformed with pAM552-AflII, as determined from 4 separate colonies each on Biotek Synergy H1 plate readers in 96 well flat bottom plates (Costar) in 100 µl LB supplemented with 50 µg/ml carbenicillin, 37° C., linear shaking with 2 mm amplitude, at 731 cycles per min). In order to remove the 23S rRNA gene, pAM552-AflII was digested with AflII (New England Biolabs) for 1 hr at 37° C., the backbone portion of the vector was gel-purified and ligated with T4 DNA ligase (New England Biolabs) overnight at 16° C. It was then transformed into POP2136 cells, plated on LB/agar plates supplemented with 50 µg/ml carbenicillin, and grown at 30° C. Plasmids from several colonies were isolated and fully sequenced. The resulting pAM552-Δ23S-AflII plasmid contains the 16S rRNA, 23S processing stems with an added AflII restriction site, 5S rRNA, and β-lactamase resistance gene and ColE1 ori. Vector backbone was prepared by digesting pAM552-Δ23S-AflII with AflII restriction enzyme at 37° C. for 2 Ms and purification using an E.Z.N.A. Cycle Pure kit.

All the CP23S constructs were assembled in parallel by Gibson assembly reaction in a 96-well PCR plate. For each CP23S target, 50 ng of AflII-digested purified backbone was added to 3Fold molar excess of the PCR-amplified and purified CP23S insert. Gibson assembly mix [Gibson 2009] (15 µl) was added, the final volumes brought to 48 µl with nucleaseFree water, and incubated at 50° C. for 1 hr in the PCR machine. No CP23S insert was added to the negative control reaction. To check the efficiency of DNA assembly, 2 µl of selected assembly reactions were transformed into electrocompetent POP2136 cells. Following 1 hour recovery at 37° C. in SOC media, a quarter of each transformation was plated on LB-agar plates supplemented with 50 µg/ml carbenicillin and grown for 20 hours at 30° C. A typical CP23S assembly reaction generated 30-120 POP2136 colonies with the control reaction generating only few colonies.

Testing cp23S rRNA Constructs

Transformation of SQ171/pCSacB rubidium chloride-competent cells was carried out in a 96-well plate. Two µl of the Gibson Assembly reactions were added to 20 µl competent cells in the pre-chilled plate. After 45 min incubation in ice/water bath, 45 sec at 42° C. and 2 min on ice, 130 µl of SOC medium were added to the wells and the plate was incubated 2 hr at 37° C. with shaking at 600 rpm on a microplate shaker. Forty µl of medium were then transferred from each well to the wells of another 96-well plate containing 120 µl SOC supplemented with 100 µg/ml ampicillin and 0.25% sucrose. The plate was incubated overnight at 37° C. with shaking at 600 rpm. A 96-pin replicator was used to spot aliquots of the cultures onto a rectangular LB agar plate containing 100 µg/ml ampicillin, 5% sucrose and 1 mg/ml erythromycin. The plate was incubated overnight at 37° C. and the appearance of $Amp^r/Ery^r$ transformants was recorded. The completeness of the replacement of the wild type pCSacB plasmid with the plasmids carrying circularly permuted 23S rRNA gene was verified by PCR using a mixture of three primers: primer 1 (GCAGATTAGCACGTCCTTCA [SEQ ID NO: 195]) complementary to the 23S rRNA segment 50-69), primer 2 (CGTTGAGCTAACCGGTACTA [SEQ ID NO: 196]) containing the sequence of the 23S rRNA segment 2863-2882, and primer 3 (GGGTGATGTTTGAGATATTTGCT [SEQ ID NO: 197]) corresponding to the sequence of the 16S/23S intergenic spacer 139-116 bp upstream from the 23S rRNA gene in rrnB. The combination of the primers 1 and 3 produces a 207 bp PCR band if wild type rrn operon is present; the combination of the primers 1 and 2 produces a 112 bp PCR band on the templates with circularly permuted 23S rRNA gene.

In order to reduce the number of false-negative cp23S rRNA variants, the experiment was repeated one more time using de novo assembled Gibson reactions with the cp23S rRNA constructs that failed to replace pCSacB in the first experiment. Two additional functional cp23S rRNA constructs were recovered from the second attempt. Altogether, 22 cp23S rRNA variants were able to replace pCSacB in the SQ171 cells. CP23S identity was confirmed by plasmid sequencing. Growth rates were analyzed on Biotek Synergy H1 plate readers in 96 well flat bottom plates (Costar) in 100 µL LB with 50 µg/ml carbenicillin. Doubling times and final OD600 after 18 hours are shown in Table 1.

Construction of pRibo-T

In order to avoid generation of mutations in the 23S rRNA gene during PCR amplification for Gibson assembly, the 23S rRNA gene variant circularly permuted at 11101 (corresponding to CP2861) was first cloned in the pUC18 vector. For that, the 23S rRNA gene circularly permuted at was PCR-amplified from circularized 23S rRNA gene prepared in the circular permutation study (above) by using the highFidelity AccuPrime Taq polymerase (Life Technologies) and primers containing BamHI restriction sites (shown in bold) TATTGGATCCGATGCGTTGAGCTAACCGGTA (SEQ ID NO: 198) and TTATGGATCCTGCGCTTACACACCCGGCCTAT (SEQ ID NO: 199). The amplified fragment was cut with BamHI and cloned in dephosphorylated BamHI-cut pUC18 plasmid. A plasmid containing CP101 23S rRNA (pUC23S) was fully sequenced to verify the lack of mutations in the 23S rRNA gene.

For preparation of pRibo-T (FIG. 4B), pAM552-Δ235-AflII plasmid (see above) served as a recipient for the CP101 23S rRNA gene. The CP101 23S RNA gene was excised from the pUC23S plasmid by BamHI digestion and gel purified. In order to graft the CP101 23S rRNA gene into the 16S rRNA gene, the plasmid backbone was prepared by PCR-amplifying the plasmid pAM552-Δ235-AflII (5 ng in 50 µl reaction) using primers introducing poly-A linkers and sequences corresponding to 11101 of 23S rRNA (underlined) and h44 in 16S rRNA (italicized)

(reverse primer with tether T1)
(SEQ ID NO: 200)
TTAGTACCGGTTAGCTCAACGCATCG(T)$_{7-12}$CGAAGGTTAAGC
TACCTACTTCTTTTGC
and (forward primer with tether T2)
(SEQ ID NO: 201)
TTGATAGGCCGGGTGTGTAAGCGCAG(A)$_{7-12}$GGAGGGCGCTTA
CCACTTTGT.

The PCR reaction, which was catalyzed by Phusion High Fidelity DNA polymerase, was carried out under the following conditions: 98° C. for 2 min followed by 30 cycles of (98° C., 30 sec; 62° C., 30 sec; 72° C., 2 min) followed by 72° C. for 5 min. The resulting 4.6 kb PCR fragment was treated with DpnI for 4 hr at 37° C. and purified using Wizard SV Gel and PCR Clean-Up kit (Promega). The PCR-amplified plasmid backbone and the gel-purified CP101 23S rRNA gene fragment were combined in a Gibson Assembly reaction. Five µl of the reaction mixture was transformed into 50 µl electrocompetent POP2136 E. coli cells. Cells were plated onto LB/agar plate supplemented with 100 µg/ml ampicillin. After 24 hr incubation at 30° C., the colonies appeared. Seventeen colonies were picked, grown in LB/ampicillin at 30° C., plasmids were isolated and linkers were sequenced using the primers GAACCT-TACCTGGTCTTGACATC (SEQ ID NO: 202) (corresponding to the 16S rRNA sequence 976-998) and ATATC-GACGGCGGTGTTTG (SEQ ID NO: 203) (corresponding to the 23S rRNA sequence 2476-2495) to verify the complexity of the linker library (Table 2). All the colonies were then washed off the plate and total plasmid was extracted and used to transform SQ171 competent cells.

Functional Replacement of the Wild-Type Ribosome by Ribo-T

SQ171 cells carrying pCSacB plasmid, which contains wild-type rrnB operon, were transformed with the total pRibo-T preparation isolated from the POP2136 cells. Briefly, 250 ng of plasmid preparation were added to 250 µl of rubidium chloride-competent cells. Cells were incubated 45 min on ice, 45 sec at 42° C. and 2 more min on ice followed by addition of 1 ml SOC medium and incubation at 37° C. for 2 hours with shaking. A 150 µl aliquot of the culture was transferred to 1.85 ml SOC supplemented with 100 µg/ml ampicillin and 0.25% sucrose (final concentrations) and grown overnight at 37° C. with shaking. Cells were spun down and plated on an LB agar plate containing 100 µg/ml ampicillin, 5% sucrose and 1 mg/ml erythromycin. Eighty of the colonies that appeared after 48 hrs incubation of the plate at 37° C. were inoculated in 2 ml LB supplemented with 100 µg/ml ampicillin and grown for 48 hrs. The growth rate of ~30 clones that managed to grow during that period was then assessed in LB/ampicillin medium in the 96-well plate. Plasmids were isolated from 6 faster growing clones and linkers were sequenced. The linker T1 in five sequenced clones was composed of 9 adenines and linker T2 was composed of 8 adenines, while one clone had the reverse combination. Total RNA was extracted from these clones using RNeasy Mini Kit (Qiagen) and analyzed by agarose electrophoresis. The successful replacement of the wild type pCSacB plasmid with the pRibo-T plasmids carrying Ribo-T was verified by PCR using primers GACAGTTCGGTCCCTATCTG (SEQ ID NO: 204)(corresponding to the 23S rRNA sequence 2599-2618) and TTAAGCCTCACGGTTCATTAG (SEQ ID NO: 205) (complementary to the 23S rRNA sequence 2880-2900) and additionally verified by primer extension on the total cellular rRNA. The growth of the cells was monitored at 37° C. in 150 µl of LB supplemented with 100 µg/ml of ampicillin in the wells of a 96-well plate in the TECAN microplate reader (15 mM orbital shaking with a 3 mm amplitude followed by 5 min rest prior to reading). The doubling time (τ) values estimated from the logarithmic parts of the growth curves are indicated in FIG. 6.

Polysome Analysis

The cultures of cells (250 ml) of the SQ171fg strain transformed with either pAM552 (WILD-TYPE) or pRibo-T8/9 were grown at 37° C. with vigorous shaking. When the optical density reached $A_{600}$ 0.4-0.7, chloramphenicol solution was added to obtain final concentration of 125 µg/ml and, after 5 min, cells were pelleted by centrifugation at 4° C. Polysomes were prepared following the published protocol [Fredick 2000] by freezing-thawing in the lysis buffer (20 mM Tris-HCl, pH 7.5, 15 mM $MgCl_2$) supplemented with 1 mg/ml lysozyme 0.25% sodium deoxycholate and 2 U of RQ1 DNase (Promega). The lysates were centrifuged at 20,000 g for 30 mM at 4° C. and polysomes-containing supernatants (20 $A_{260}$) were loaded onto the 12 ml 10%-50% sucrose gradient (buffer: 20 mM Tris-HCl, pH 7.5, 10 mM $MgCl_2$, 100 mM $NH_4Cl_2$, 2 mM β-mercaptoethanol). Polysomes were resolved by centrifugation in a SW-41 rotor (39,000 rpm, 3 hr, 4° C.). Gradients were fractionated using BioComp Instrument gradient fractionator and fractions were collected in the wells of a 96-well plate. Appropriate fractions were pooled, ribosomes were ethanol-precipitated and resuspended in 200 µl of buffer containing 300 mM sodium acetate, pH 5.5, 5 mM EDTA, 0.5% SDS. rRNA was isolated by successive extractions with phenol (pH 6.6), phenol/chloroform and chloroform. After ethanol precipitation, RNA was analyzed by non-denaturing agarose gel electrophoresis.

Analysis of Protein Synthesis Rate and Proteins Synthesized in Ribo-T Cells

Protein synthesis rate in SQ171fg cells expressing either wild-type ribosomes (plasmid pAM552) or Ribo-T (pRibo-T plasmid) was measured by following incorporation of [$^{35}$S]-methionine into proteins as described [Kannan et al., Cell 2012]. Specifically, 0.25 µCi of [$^{35}$S]-methionine (specific activity 1,175 Ci/mmol) (ARC) was added to 1 ml of exponentially growing cells at 37° C. and after 45 sec incubation proteins were precipitated by addition of 1 ml of ice-cold 25% trichloroacetic acid (TCA) containing 2% casamino acids. After incubating for 30 min on ice and then 30 min at 100° C., samples were passed through G4 glass fiber filters. The filters were washed three times with 3 ml of ice cold 5% TCA, and once with 3 ml of acetone and air dried, and the amount of retained radioactivity was determined by scintillation counting. Preliminary measurements of the time course of [$^{35}$S]-methionine incorporation in the faster-growing SQ171fg/pAM552 cells showed that radioactivity curve plateaus after 120 sec of incubation of cells with [$^{35}$S]-methionine.

Exponential cultures (250 ml) of the SQ171fg strain transformed with either pAM552 (A2058G) or pRibo-T8/9 growing in LB medium supplemented with 100 µg/ml of ampicillin and 50 µg/ml of spectinomycin were harvested by centrifugation and cells were flashFrozen in liquid nitrogen. Protein isolation and two-dimensional gel electrophoresis was performed by Kendrick Labs, Inc. (Madison, Wis.).

Preparation of Ribo-T and Wild Type Ribosomes and Analysis of their RNA and Protein Content Ribosomes were prepared from the exponentially growing cells of the SQ171fg strain transformed with either pAM552 (WILD-TYPE) or pRibo-T8/9 as described[31].

RNA was phenol extracted, precipitated as previously described and resolved by electrophoresis in a denaturing 6% (acrylamide:bis-acrylamide ratio 1:19 w/w) polyacrylamide gel (for the 5S rRNA analysis) or 4% (acrylamide:bis-acrylamide ratio 1:29 w/w) polyacrylamide gel (for the analysis of large rRNAs).

Ribo-T associated ribosomal proteins were analyzed by mass spectrometry at the Proteomics Center of Excellence, Northwestern University. Ribosomes were precipitated by incubation in 20% trichloracetic acid at 4° C. overnight and centrifugation at 14,000 g for 10 min. Precipitated ribosomes were washed once with cold 10% trichloracetic acid and twice with acetone. The pellet was air dried for 10-20 min prior to resuspension in 20 µl 8 M urea. Proteins were reduced with 10 mM dithiothreitol and cysteine residues alkylated with 50 mM iodoacetamide in the final volume of 160 µl. Sequencing grade trypsin (Promega) was added at a 1:50 enzyme:protein ratio and after overnight digestion at room temperature, the reaction was stopped by addition of formic acid to 1%. Following digestion, peptides were desalted using C18 Spin columns (Pierce, cat #89870) and lyophilized. Amino reactive TMT reagents (126/127, Thermo Scientific, cat #90065) was used for peptide labeling. The reagents were dissolved in 41 µl acetonitrile and added to the lyophilized peptides dissolved in 100 µl of 100 mM triethylammonium bicarbonate. After 1 hr at room temperature, the reaction was quenched by adding 8 µl of 5% hydroxylamine. Following labeling, the two samples under analysis were mixed in 1:1 ratio. Peptides were desalted using C18 ZipTip Pipette Tips (EMD Millipore) and resuspended in 30 µL of solvent A (95% water, 5% acetonitrile, 0.2% formic acid).

Peptides were analyzed using nanoelectrospray ionization on an Orbitrap Elite mass spectrometer (Thermo Scientific). Proteome Discoverer (Thermo Scientific) and the Sequest algorithm was used for data analysis. Data was searched against a custom database containing UniProt entries using *Escherichia coli* taxonomy, allowing 3 missed cleavages, 10 ppm precursor tolerance, and carbamidomethylation of cysteine as a static modification. Variable modifications included oxidation of methionine, TMT of lysine and N-terminal TMT. For quantification via the reporter ions the intensity of the signal closest to the theoretical m/z, within a ±10 ppm window, was recorded. Reporter ion intensities were adjusted based on the overlap of isotopic envelopes of all reporter ions as recommended by the manufacturer. Only peptides with high confidence were used for quantification. Ratios of 126/127 were normalized based on median.

Sucrose Gradient Analysis of Ribosomes and Ribosomal Subunits

Wild type 70S ribosomes or Ribo-T isolated from SQ171fg cells as described above were diluted ca. 70 fold in high $Mg^{2+}$ buffer (20 mM Tris-HCl, pH 7.5, 100 mM $NH_4Cl$, 2 mM 2-mercaptoethanol, 15 mM $MgCl_2$) or low $Mg^{2+}$ buffer (20 mM Tris-HCl, pH 7.5, 100 mM $NH_4Cl$, 2 mM 2-mercaptoethanol, 1.5 mM $MgCl_2$). After incubation for 30 mM at 4° C., ribosomes and subunits were resolved in 10-40% 12 ml sucrose gradients prepared with the same buffers. Gradients were centrifuged in the SW41 rotor at 38,000 rpm for 3 hr at 4° C. Ribosome profiles were then analyzed using gradient fractionator (BioComp Instrument).

Probing the Structure of the Ribo-T Tethers

The structure of the tethers was probed by dimethylsulfate (DMS) modification following a published protocol [Merryman 1998]. Briefly, 10 pmol of Ribo-T or WILD-TYPE ribosomes were activated by incubation for 5 min at 42° C. in 50 µl of buffer 80 mM HEPES-KOH, pH 7.6, 15 mM $MgCl_2$, 100 mM $NH_4Cl$ containing 20 U of RiboLock RI RNase inhibitor (Thermo Fisher Scientific). Two µl of DMS (SIGMA) diluted 1:10 in ethanol were added (2 µl of ethanol were added to the unmodified controls) and samples were incubated for 10 min at 37° C. The modification reaction was stopped and rRNA extracted as described [Merryman 1998]. Primer extensions were carried out using the primers GACTGCCAGGGCATCCACCG (SEQ ID NO: 206) and AAGGTTAAGCCTCACGG (SEQ ID NO: 207) (for tether T1) or CCCTACGGTTACCTTGTTACG (SEQ ID NO: 208) for tether T2.

Additionally, the integrity of the tethers in the Ribo-T preparation was tested by extension of the primers annealing immediately 3' to the tether. Primer GTACCGGTTAGCT-CAACGCATC (SEQ ID NO: 209) was extended by reverse transcriptase across tether T1 in the presence of dATP, dTTP, dGTP and ddCTP and primer CACAAAGTGGTAAGCGC-CCTCCT (SEQ ID NO: 210) was extended across tether T2 in the presence of dATP, dTTP, dCTP and ddGTP.

Testing Ribo-T Activity in Cell-Free Translation System

DNA template containing the T7 promoter and the gene of the superfolder green fluorescence protein [Pedelac1 2006] was PCR amplified from a pY71-sfGFP plasmid [Bundy 2010] using primers TAATACGACTCACTATAGGG (SEQ ID NO: 211) and CTTCCTTTCGGGCTTTGTT. (SEQ ID NO: 212) GFP mRNA was prepared by in vitro transcription and purified by size-exclusion chromatography on a Sephadex G50 mini-column, phenol extraction and ethanol precipitation. The transcript was translated in the Δ(ribosome, amino acid, tRNA) PURExpress system kit (New England Biolabs). A typical translation reaction was assembled in a total volume of 10 µl and contained 2 µl of the kit solution A, 1.2 µl of factor mixture, 1 µl amino acid mixture (3 mM each), 1 µl tRNA (20 µg/ml), 0.4 µl Ribolock RNase inhibitor (40 U/µl), 5 µg (~20 pmol) GFP transcript and 22 pmol of wild type ribosomes or Ribo-T. Samples were placed in wells of a 384-well black wall/clear flat bottom tissue-culture plate (BD Biosciences) and covered with the lid. Reactions were incubated at 37° C. in a microplate reader (Tecan), and fluorescence values were recorded every 20 min at $\lambda_{Exc}$=488 nm and $\lambda_{Em}$=520 nm over 7 hrs. Protein synthesis rates were calculated by linear regression over the time points 0, 40 and 60 min with a $R^2$>0.9 using the trendline function of Excel (Microsoft). Time point 20 min was not taken into consideration because the plate was switched from ice to 37° C. at time 0.

Transcription/translation of the DHFR template supplied with the Δ(ribosome, amino acid, tRNA) PURExpress kit (New England Biolabs) was carried in the presence of [$^{35}$S] L-methionine (1175 Ci/mmol) using manufacturers protocol. A typical 5 µl reaction, assembled as described above but using 50 ng of the DNA template, was supplemented with 5 µCi [$^{35}$S] L-methionine and 10 pmol of wild type or Ribo-T ribosomes. When needed, the reactions were supplemented with 50 µM erythromycin. Reactions were incubated 2 hours at 37° C. and protein products were analyzed by SDS gel electrophoresis in 16.5% Bis-Tris gels (Biorad) using NuPAGE MES/SDS running buffer (Invitrogen). Gels were stained, dried and exposed to a phosphorimager screen overnight. Radioactive bands were visualized by Typhoon phosphorimager (GE Healthcare).

Toe-Printing Analysis

Toe-printing was performed as previously described [Vazquez-Lasop 2008; Orelle 2013]. When needed, the threonyl-tRNA synthetase inhibitor borrelidin or the initiation inhibitor thiostrepton were added to the reactions to the final concentrations of 50 µM.

Construction of the Plasmids for Testing oRibo-T Activity In Vivo

The backbone plasmid pT7wtK was first prepared from the commercial plasmid T7FLAG™-4 (Sigma Aldrich) by introducing the following changes. First, the bla gene was deleted using inverse PCR with phosphorylated primers TAACTGTCAGACCAAGTTTACTC (SEQ ID NO: 213) and ACTCTTCCTTTTTCAATATTATTGAAG (SEQ ID NO: 214) and Phusion High Fidelity DNA polymerase. Following purification with E.Z.N.A. Cycle Pure kit, DNA was blunt-end ligated for 14 hours at 16° C. using T4 DNA ligase, and transformed into electrocompetent DH5α E. coli cells and plated on LB-agar supplemented with 30 µg/ml kanamycin. Next, a BglII-NotI cloning site was introduced using phosphorylated primers AGATCTGTTGCTACGCA-GCGTTGCGGCCGCTGAAGATCGATCTCGACG (SEQ ID NO: 215) and

```
                                    (SEQ ID NO: 216)
GCCTCCTATGAAAAAATAACAGATATAGTCTCCCTATAGTGAGT
CGTATTAGG,
``` with BglII and NotI sites in bold. A sequence 3' of the T7 promoter, termed N15 (underlined), optimized for T7 expression of an orthogonal gene [An 2009] was introduced on one of the primers. Purified PCR product was blunt-end ligated with T4 DNA ligase for 14 hours at 16° C., transformed into DH5α electrocompetent cells and plated on LB-agar supplemented with 30 µg/ml kanamycin. The resulting plasmid pT7wtK contains a T7 promoter, wild-type SD sequence, a BglII-NotI cloning site, T1/T2 terminator, pMB1 origin of replication, a lac/gene and a kanamycin resistance gene.

To create plasmid pT7wtGFP, primers GGTGGTAGATC-TATGAGCAAAGGTGAAGAAC (SEQ ID NO: 217) and GGTGGTGCGGCCGCGGGCTTTGTTAGCAG (SEQ ID NO: 218) were used to PCR amplify the sf-gfp gene from pY71-sfGFP [Bundy 2010], adding BglII and NotI restriction sites (bold) at the ends of the sf-gfp PCR product. Purified PCR product and plasmid pT7wtK were digested with BglII and NotI (New England Biolabs) for 1 hour at 37° C. The pT7wtK digested vector was treated with alkaline phosphatase CIP (New England Biolabs) for 1 hour at 37° C. Both reactions were purified with E.Z.N.A. Cycle Pure kit. The sf-gfp insert was added in 3Fold molar excess to 50 ng pT7wtK backbone, and ligated with T4 DNA ligase (NEB) for 14 hrs at 16° C., transformed into DH5α electrocompetent cells and plated on LB-agar supplemented with 30 µg/ml kanamycin.

To create pT7oGFP containing sf-gfp whose translation is controlled by an orthogonal SD sequence, the wild-type SD sequence of pT7wtGFP (AGGAGG) was mutated to an orthogonal sequence CACCAC [Rackham 2005] by inverse PCR using phosphorylated primers ATGAGCAAAGGT-GAAGAAC (SEQ ID NO: 219) and AGATCTGTGGTGT-GAAAAAATAACAGATATAGTCTC (SEQ ID NO: 220). PCR product purified with E.Z.N.A. Cycle Pure kit was blunt-end ligated with T4 DNA ligase for 14 hours at 16° C., transformed into electrocompetent DH5α cells and plated on LB-agar supplemented with 30 µg/ml kanamycin.

Finally, the T7 promoter was replaced with the lpp5 promoter [An 2009]. To achieve that, inverse PCR was performed using pT7oGFP as template and phosphorylated primers

```
                                    (SEQ ID NO: 221)
TATACTTGTGGAATTGTGAGCGGATAACAATTCTATATCTGTTA
TTTTTTCA
and
                                    (SEQ ID NO: 222)
ACACAAAGTTTTTTATGTTGTCAATATTTTTTTGATAGTGAGTC
GTATTAGGATC,
```

(the lpp promoter is underlined). The lacO site (bold) was included in order to provide for inducible expression in POP2136 strain controlled with isopropyl β-D-1-thiogalactopyranoside (IPTG). DNA was purified, blunt-end ligated, transformed into DH5α cells and plated on LB-agar supplemented with 30 µg/ml kanamycin. The resulting plasmid pLpp5oGFP contains a lpp5 promoter, lacO site, orthogonal SD sequence, sf-gfp gene, T1/T2 terminator, pMB1 origin of replication, a lac/gene and a kanamycin resistance gene.

The anti-Shine-Dalgarno sequence of pRibo-T 16S rRNA was mutated from wild-type (5'-ACCUCCUUA-3' [SEQ ID NO: 223]) to an orthogonal sequence (5'-AUUGUGGUA-3' [SEQ ID NO: 224]) [Rackham 2005] by inverse PCR using phosphorylated primers CCTTAAAGAAGCGTACTTTG-TAG (SEQ ID NO: 225) and TACCACAATGATCCAAC-CGCAGG (SEQ ID NO: 226), pRibo-T as template and Phusion High Fidelity DNA polymerase. PCR was run at the following conditions: 98° C., 3 min followed by 25 cycles (98° C., 30 sec; 55° C., 30 sec; 72° C., 120 sec), followed by final extension 72° C., 10 min. Correct size band was purified by agarose gel electrophoresis and extracted using the E.Z.N.A. Gel Extraction kit. It was circularized by blunt-end ligation and transformed into POP2136 electrocompetent cells. Cells were plated on LB/agar plates supplemented with 50 µg/ml carbenicillin and grown at 30° C. overnight. Colonies were isolated and poRibo-T was fully sequenced.

Testing Activity of oRibo-T In Vivo

Electrocompetent POP2136 cells were transformed with the following plasmid combinations: i) pAM552 and pT7wtK (no gfp control), ii) pAM552 and pLpp5oGFP, iii) pAM552o and pLpp5oGFP and iv) poRibo-T1 and pLpp5oGFP. Transformants were plated on LB plates supplemented with 50 µg/ml carbenicillin and 30 µg/ml kanamycin and incubated for 24 hours at 30° C. Wells of a 96-well plate with low evaporation lid (Costar) was filled with 100 µl of LB media supplemented with 50 µg/ml carbenicillin and 30 µg/ml kanamycin. The wells were inoculated with colonies from each plasmid combination above (six colonies each), and incubated at 30° C. for 14 hours with shaking. Clear bottom chimney wells of another 96-well plate (Costar) were filled with 100 µL of LB media supplemented with 50 µg/ml carbenicillin, 30 µg/ml kanamycin, and 1 mM IPTG. The plate was inoculated with 2 µl of saturated initial inoculation plate, and incubated with linear shaking (731 cycles per min) for 16 Ms at 42° C. on a Biotek Synergy H1 plate reader, with continuous monitoring of cell density ($A_{600}$) and sf-gfp fluorescence (excitation 485 and emission 528 with sensitivity setting at 80).

Testing oRibo-T Activity in a Cell-Free Translation System

Ribosomes (wild-type) or oRibo-T (mixed with wild-type ribosomes) were prepared from SQ171fg cells transformed with pAM552 or poRibo-T1, respectively. An orthogonal sf-gfp gene was PCR amplified from the plasmid pT7oGFP using primers TAATACGACTCACTATAGGG (SEQ ID NO: 227) and ACTCGTCGAGATCGATCT (SEQ ID NO: 228). The transcription-translation reaction was carried out in Δ(ribosome, amino acid, tRNA) PURExpress system as described above. The 7.5 µl reactions were supplemented with 18.75 ng DNA template and 7.5 pmol ribosomes and when needed, clindamycin or pactamycin were added to the reactions to the final concentrations of 50 µM or 100 µM respectively.

For in vitro translation of an orthogonal secM-lacZα template it was PCR amplified from the poSML plasmid using a direct primer TAATACGACTCACTATAGGG (SEQ ID NO: 229) corresponding to the T7 promoter and a reverse primer TTCCCAGTCACGACGTT (SEQ ID NO: 230), which allowed preserving 18 codons after the SecM arrest site. mRNA was prepared by in vitro transcription and purified. It was then translated in the Δ(ribosome, amino acid, tRNA) PURExpress system assembled in a total volume of 5 µl and containing 1 µl of the kit solution A, 0.6 µl of factor mixture, 0.5 µl amino acid mixture (3 mM each) lacking methionine, 0.2 µl of [$^{35}$S] L-methionine 8.5 µM (1175 Ci/mmol), 0.5 µl tRNA (20 µg/ml), 0.2 Ribolock RNase inhibitor (40 U/µl), 100 µM pactamycin, 10 pmol transcript and 10 pmol of total ribosomes. Translation was carried out for 5 min at 37° C., followed by addition of 1 µg of RNAse A and incubation for 5 min at 37° C. Translation products were analyzed in 16.5% Tricine SDS polyacrylamide gel [Schagger 1987]. The gel was stained, dried, and exposed to a phosphorimager screen overnight.

Construction of C41(DE3)/ΔlacZ58(M15)

The ΔlacZ58(M15) allele required for alpha complementation was transduced from the E. coli strain K1342 (E. coli Genetic Stock Center, Yale) into E. coli C41(DE3) strain by P1 phage transduction protocol. Transductants were selected on LB agar supplemented with 10 µg/ml tetracycline. Then colonies were re-streaked on LB-agar plates containing 10 µg/ml tetracycline, 200 µM IPTG and 80 µg/ml X-Gal. The replacement of wild-type lacZ with the ΔlacZ58(M15) allele was verified by PCR using primers ACCATGATTACGGAT-TCACTGG (SEQ ID NO: 231) and CCGTTGCACCACA-GATGAA (SEQ ID NO: 232) (the sizes of the expected PCR products are 467 bp for wild-type and 374 bp for the mutant).

Construction of the Orthogonal secM-lacZα Reporter poSML

The backbone of the pACYC177 vector was PCR-amplified using primers ATCTCATGACCAAAATCCCT-TAACGTGAGT (SEQ ID NO: 233) and GCGGT-TAGCTTTTACCCCTGCATCTTTGAG (SEQ ID NO: 234). A 568 bp DNA fragment whose ends overlapped with the amplified pACYC177 backbone and which contained T7 promoter, the orthogonal SD sequence CACCAC [Rackham 2005], the secM(121-166)-lacZα fusion from the plasmid pNH122 [Nakatogawa 2002], was synthesized by Integrated DNA Technologies. The pACYC177 backbone and the secM/lacZα construct were combined using Gibson Assembly and introduced in the C41(DE3)/ΔlacZ58(M15) cells.

Construction of the 2451/2452 Mutant poRibo-T Library and Selecting Mutants Capable of Alleviating SecM-Mediated Translation Arrest A library of A2451N/C2452N mutants was generated by inverse PCR using plasmid poRibo-T2 as a template, Phusion High Fidelity DNA polymerase, and primers AGGCT-GATACCGCCCAAG (SEQ ID NO: 235) and (SEQ ID NO: 236)
CTCTTGGGCGGTATCAGCCTNNTATCCCCGGAGTACCTTTTATC, with added sequence (underlined) used for re-circularization with Gibson assembly. PCR reaction was carried out under the following conditions: 98° C., 3 min followed by 25 cycles (98° C., 30 sec; 55° C., 30 sec; 72° C., 120 sec), followed by final extension 72° C., 10 min. The PCR-amplified DNA band was purified by extraction from the agarose gel with an E.Z.N.A. Gel Extraction kit, and re-circularized by Gibson assembly for 1 hour at 50° C. Two µl of the reaction were transformed into electrocompetent POP2136 cells plated on LB plates supplemented with 50 µg/ml carbenicillin and grown for 24 Ms at 30° C. Individual colonies were picked and sequenced to identify all possible 16 variants of the library.

The C41(DE3)/ΔlacZ58(M15) cells were transformed with the poSML reporter plasmid and plated on LB-agar containing 50 µg/ml kanamycin. One of the colonies, which appeared after overnight incubation at 37° C., was inoculated into liquid culture, grown in the presence of 50 µg/ml kanamycin and cells were rendered chemically competent. Cells were transformed with the pooled library of sixteen 2451/2452 mutants. Transformed cells were plated on LB agar containing 50 µg/ml kanamycin, 100 µg/ml ampicillin, IPTG 0.5 mM, X-Gal 40 µg/ml and 2 mM lacZ inhibitor phenylethyl-β-d-thiogalactopyranoside (PETG). Plates were incubated at 37° C. for 24 hours and photographed. 16 white colonies or 15 blue colonies were inoculated in 5 ml of LB medium supplemented with 100 µg/ml ampicillin and grown overnight. The plasmids were isolated and the identities of nucleotide residues at the position 2451 and 2452 of the 23S rRNA were analyzed by sequencing. Alternatively, the poSML-transformed C41(DE3)/ΔlacZ58(M15) cells were transformed with individual plasmids representing all possible 16 variants of the nucleotide combinations at positions 2451 and 2452. The poRibo-T2 plasmid carrying A2058G mutation was used as a control. In addition, the poRibo-T2 plasmid carrying the U2585G mutation was included in the transformation experiment. The transformed cells were plated on LB/agar containing 50 µg/ml kanamycin and 100 µg/ml ampicillin and incubated overnight at 37° C. Three colonies from each transformation were then streaked on LB/agar plates containing 50 µg/ml kanamycin and 100 µg/ml ampicillin and supplemented with 0.5 mM IPTG, 40 µg/ml X-Gal and 2 mM PETG. Plates were incubated at 37° C. for 22 hours and photographed.

Dual Orthogonal Ribo-T Expression Vector and Orthogonal Reporter

Figure 23:
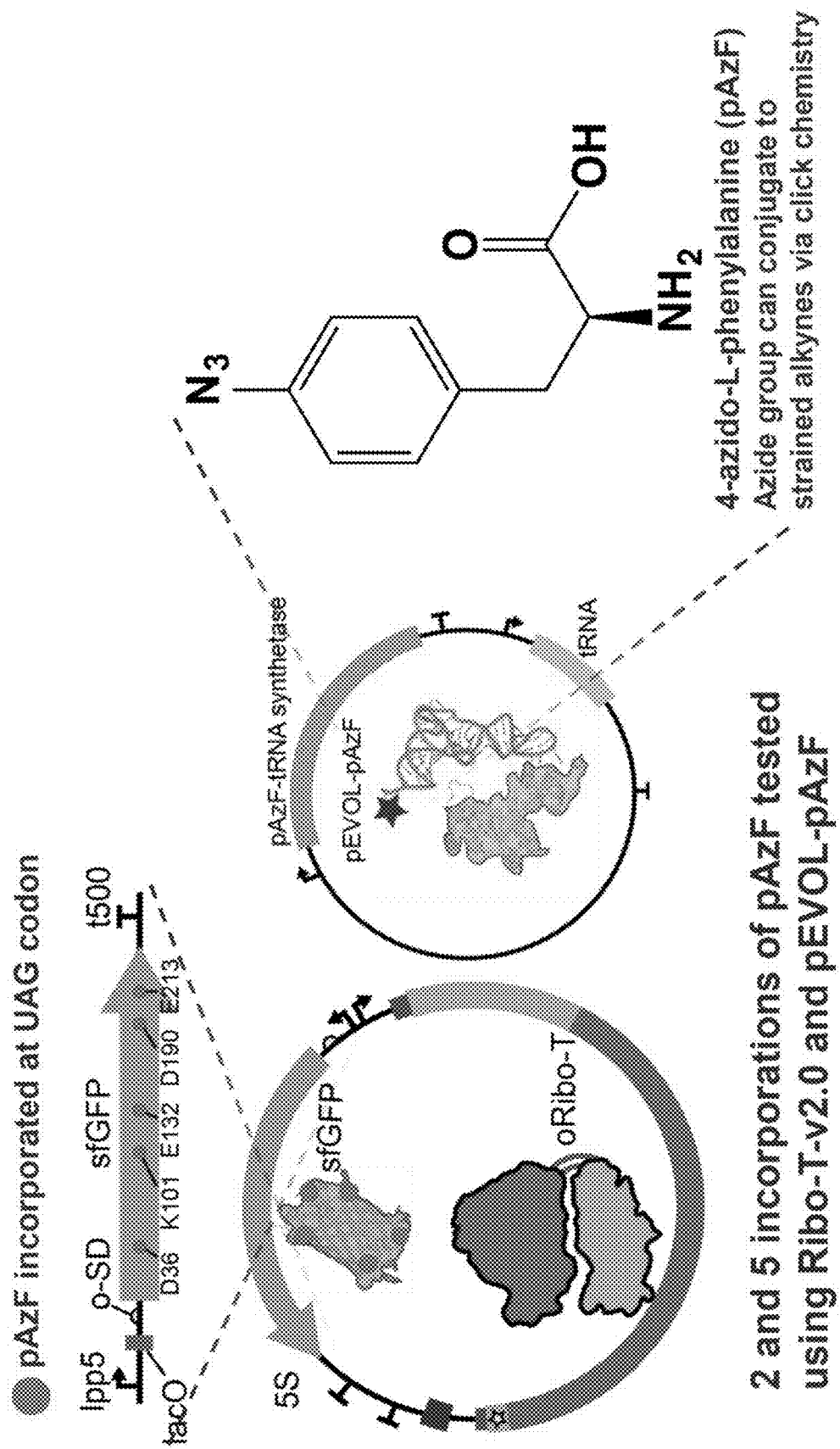
FIG. 23 illustrates the strategy and plasmids utilized for incorporating 4-azido-L-phenylalanine (pAzF) into sfGFP.

A single-plasmid coding for orthogonal Ribo-T and an orthogonal reporter gene to replace the previous two-plasmid system was prepared. The plasmid contains the Ribo-T operon with orthogonal anti-SD sequence, under the pL promoter, and an sfGFP gene with 2, or 5 TAG codons under an lpp5 promoter with lacO site for IPTG inducibility, and t500 terminator, with AmpR gene for antibiotic selection. For control, untethered orthogonal ribosomes were cloned into the vector in place of oRibo-T. The pEVOL-pAzF plasmid containing the pAzF-tRNA synthetase and corresponding pAzF-tRNA mutated for TAG stop codon suppression was used [Young 2010]. Plasmid maps and 4-azido-L-phenylalanine (pAzF) target are shown in FIG. 23.

Incorporating p-Azido-L-Phenylalanine into sfGFP-STAG with Ribo-T

Figure 14:
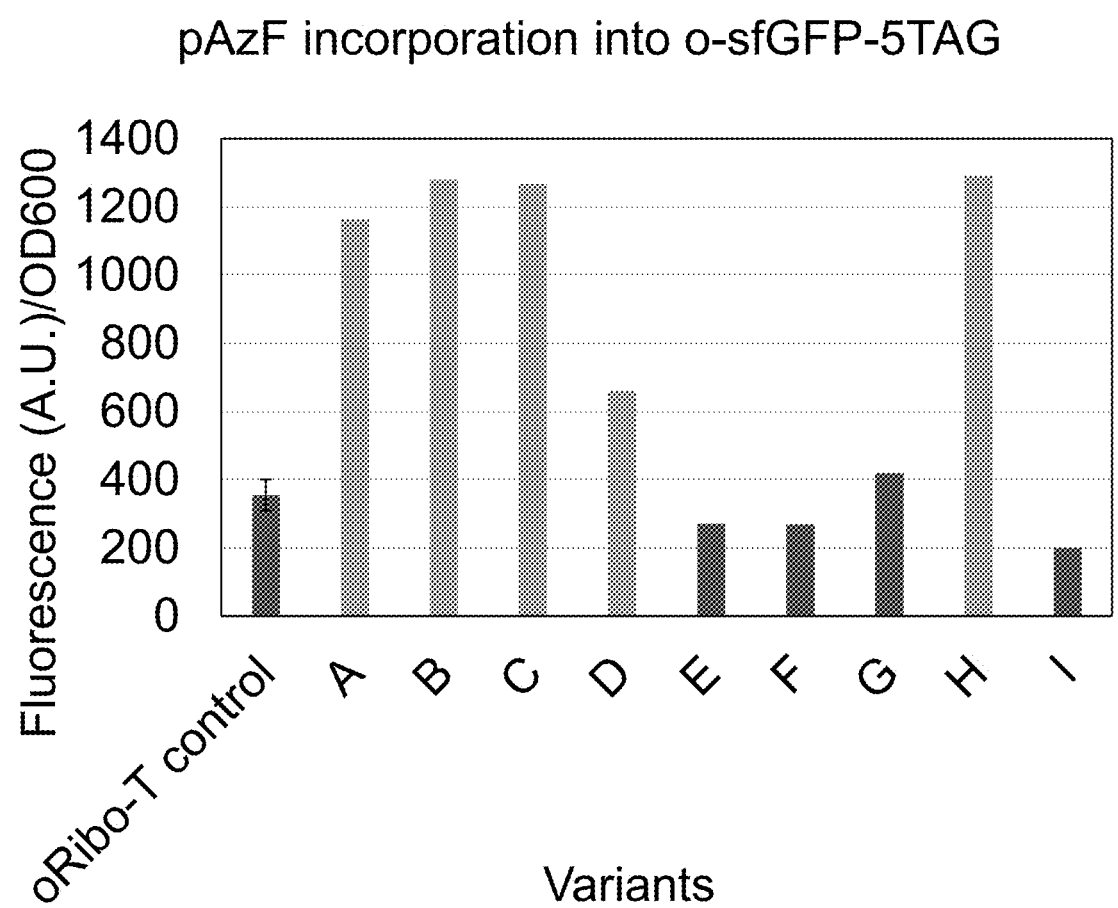
FIG. 14 shows unnatural amino acid incorporation into o-sfGFP with a tethered ribosome.

Plasmid oRibo-T-sfGFP with sfGFP gene modified with 5-TAG as prepared in the example above under orthogonal SD site and variations to the oRibo-T portion of the plasmid was transformed into rEcoliΔ prfA mutS+upp-λ, red strain containing pEVOL-pAzF plasmid [Young 2010], and plated on LB agar plates supplemented with 50 µg/ml carbenicillin and 25 µg/ml chloramphenicol (for pEVOL-pAzF). Variants were randomly selected from a plate, and used to inoculate a 96-well plate containing in each well 100 µL LB supplemented with 50 µg/ml carbenicillin and 25 µg/ml chloramphenicol, and incubated overnight at 37° C. with shaking. A fresh 96-well plate (100 µL LB with 50 µg/ml carbenicillin and 25 µg/ml chloramphenicol) was inoculated with 2 µL of saturated overnight, and incubated at 37° C. with shaking until OD600 0.2-0.3. IPTG (1 mM final), L-arabinose (0.02% final), and p-azido-L-phenylalanine (1 mM final) was added to each well, and incubated for 18 hrs at 37° C. with shaking, monitoring OD600 and sfGFP fluorescence. FIG. 14 shows final endpoint sfGFP fluorescence normalized with OD600. Variants A, B, C, D and H showed significant increased pAzF incorporation, ranging from 86% increase to 264% increase over oRibo-T control.

Example 2—Improvements to Ribosomes with Tethered Subunits

Abstract

While the exact reason is unclear, our data has shown that some orthogonal Ribo-T systems are limited at the translation initiation step. In addition, the tethers disclosed herein (i) may hinder ribosome subunit ratcheting during translation, (ii) change interactions with translation factors, and (iii) fundamentally alter the ribosome biogenesis pathways. Furthermore, it is desirable to optimize activity of orthogonal pairs (i.e. Shine-Dalgarno/anti-Shine-Dalgarno pairs), in the disclosed systems. Here, we optimized the tether composition, which shows improved functionality, and we optimized the orthogonal Shine-Dalgarno/anti-Shine-Dalgarno pair for improved orthogonal performance.

Improved Tether Sequences

Helix 44 (h44) of 16S rRNA and helix 101 (H101) of 23S rRNA are shown in FIG. 15A. The Ribo-T tether of Example 1 connects the 3' end of h44 to the 5' end of H101 with tether 1 (T1), and the 3' end of H101 to the 5' end of h44 (T2), with remnants of the apex loops (UUCG and CGA on T1, G on T2) and an added 9A/8A for T1/T2 (FIG. 15B).

Figure 16:
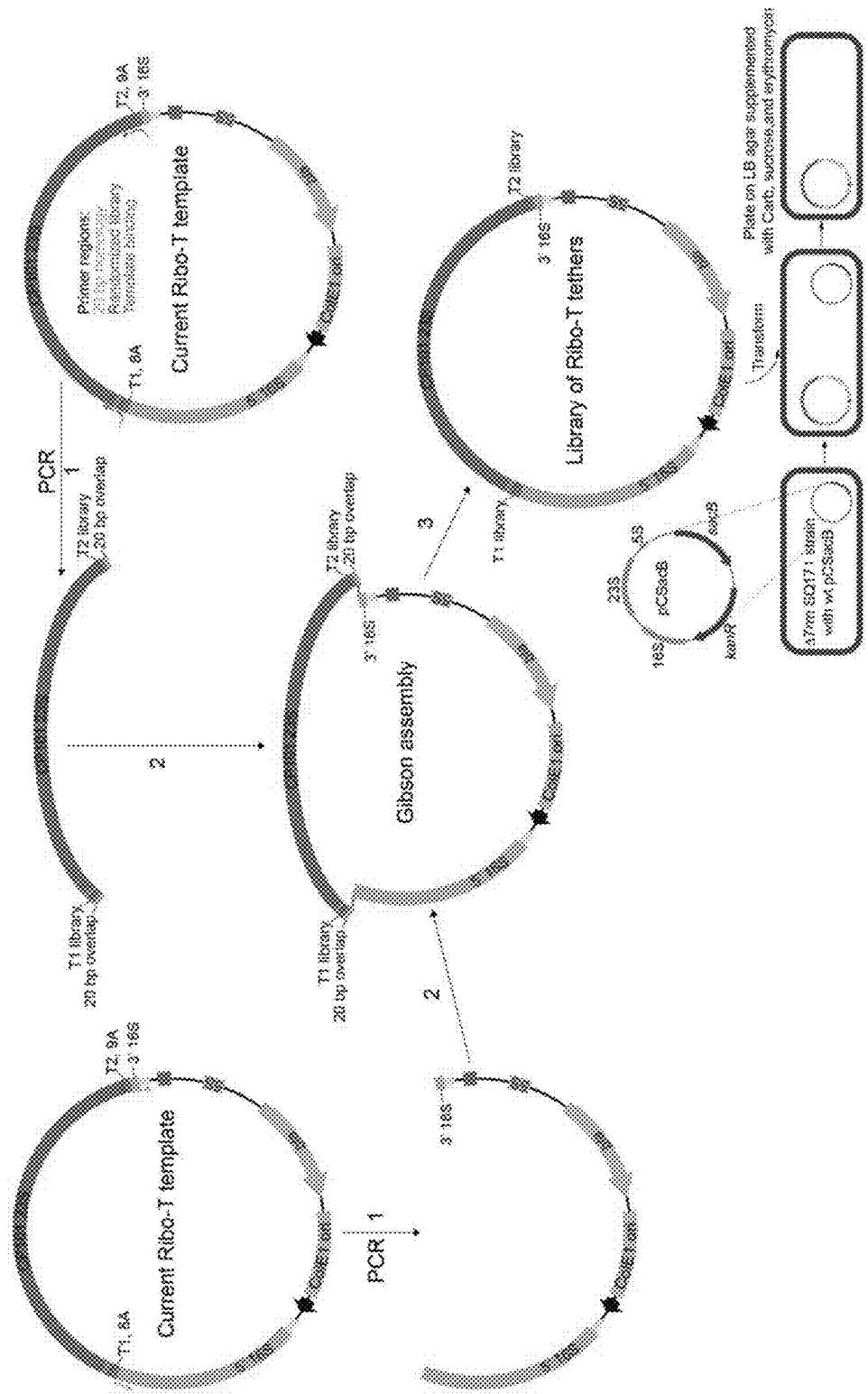
FIG. 16 provides an overview of the protocol used for optimizing the tether sequences of the libraries of FIG. 15.
Figure 18:
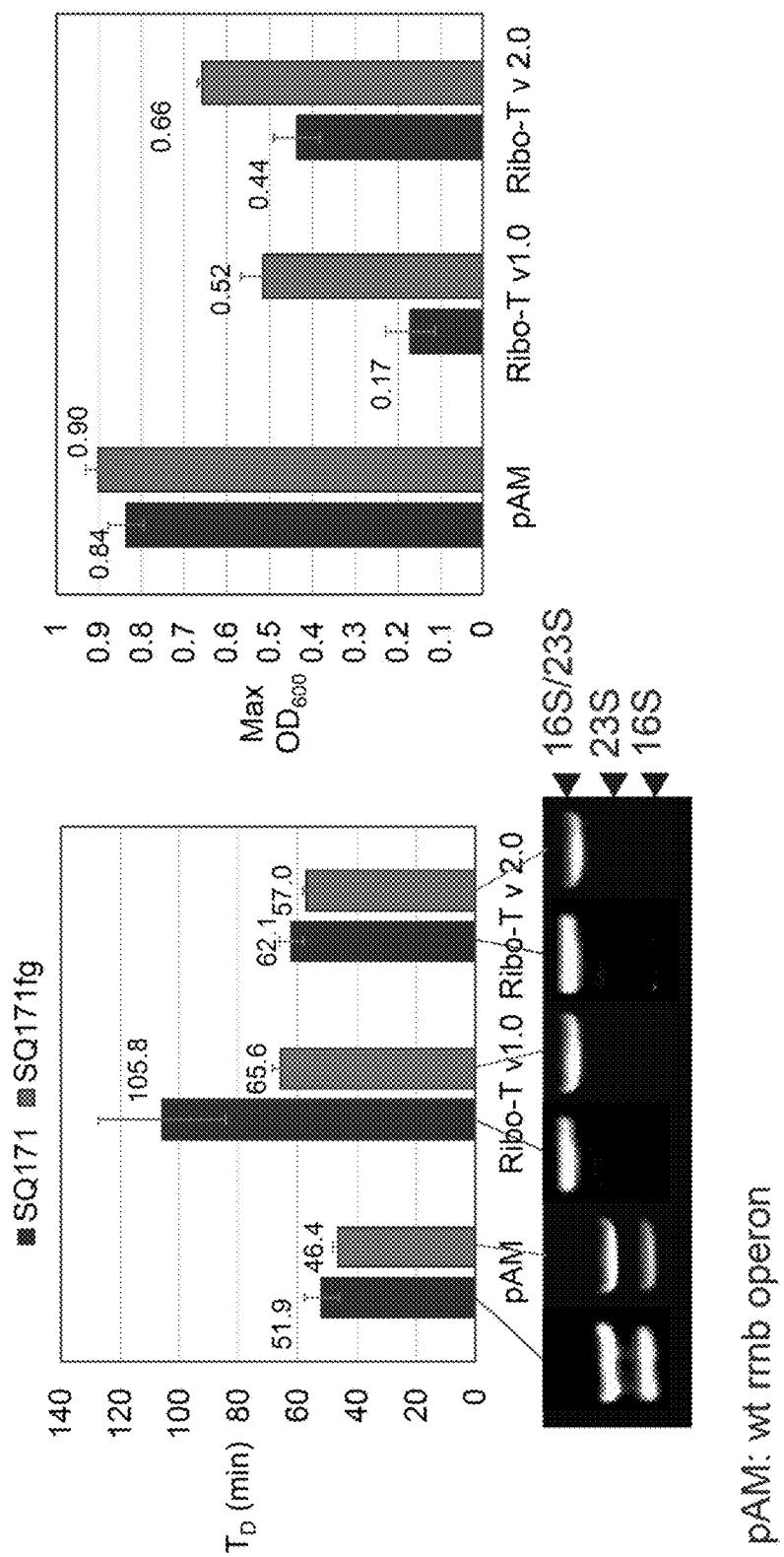
FIG. 18 illustrates that the optimized tethers of FIG. 17 enhance the growth of strains SQ171 and SQ171fg.

In this Example 2, we sought to improve Ribo-T function by optimizing the H101/h44 subunit connection point tether in composition and length. Four libraries were designed and built, and were tested for improved Ribo-T function. Libraries 1 and 2 explored tether length in a paired (FIG. 15C) and unpaired (FIG. 15D) format. Specifically, Library 1 (L1) explores a 7A-20A nucleotide tether paired with 7T-20T, for an exploration of tether length with base paring without apex loop remnants (UUCG and CGA on T1, G on T2) (FIG. 15C) for a total library size of 196 members. Library 2 (L2) explores a fully un-structured polyA tether without apex loop remnants ranging from 7A-20A (FIG. 15D) for a total library size of 196 members. We designed Library 3 (L3) and Library 4 (L4) in order to explore tether sequence with fixed length. (See scheme in FIG. 16). Library 3 (L3) includes the apex loop sequences found in the original loops (UUCG and CGA on T1, G on T2) and includes a 8N/9N (T1/T2) randomized sequence which results in a library of $1.7 \times 10^{10}$ members (FIG. 15E). Library 4 (L4) includes a 15N/10N (T1/T2) randomized sequence as a tether between the H101 loop and the h44 loop which results in a library of $1.1 \times 10^{15}$ members. We selected an optimized sequence from Library 4 (FIG. 15F), specifically T1 (CAATGAACAAT-TGGA [SEQ ID NO:237]) and T2 (GATAACTAGT [SEQ ID NO:238]), FIG. 15G and FIG. 17, which gives ~10% improvement in growth over the original tether sequence (FIG. 15B). The optimized tether was observed to enhance the growth of strains SQ171 and SQ171fg (FIG. 18).

Improved Orthogonal Pairs

Figure 19:
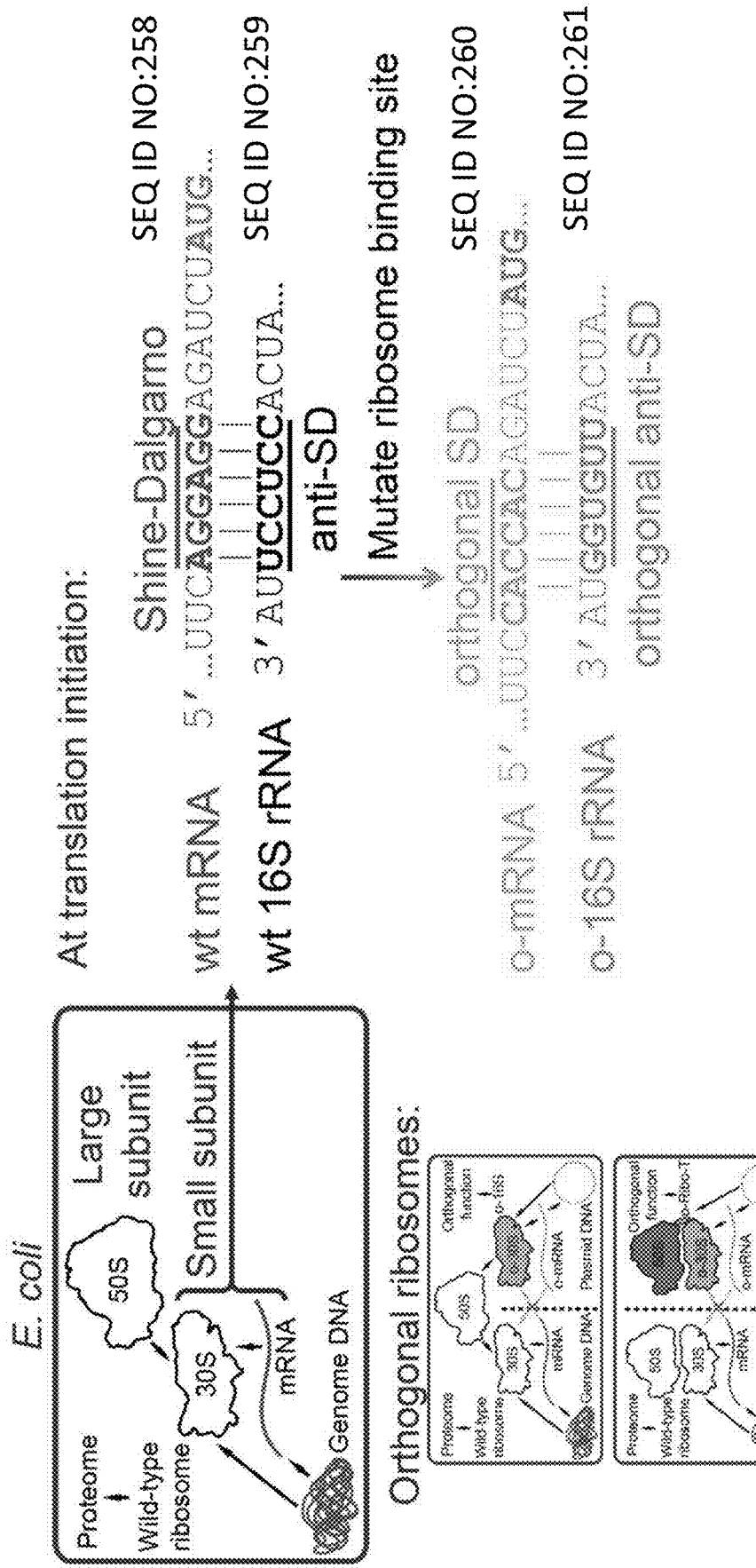
FIG. 19 provides an outline of the strategy for selecting new orthogonal pairs of Shine-Dalgarno sequences and anti-Shine-Dalgarno sequences in vivo. (See Hui, A. and H. A. de Boer. PNAS 84 (14): 4762-4766, (1987); and Rackham, 0. & Chin, J. W. *Nat Chem Biol* 1, 159-166, (2005)).
Figure 20:
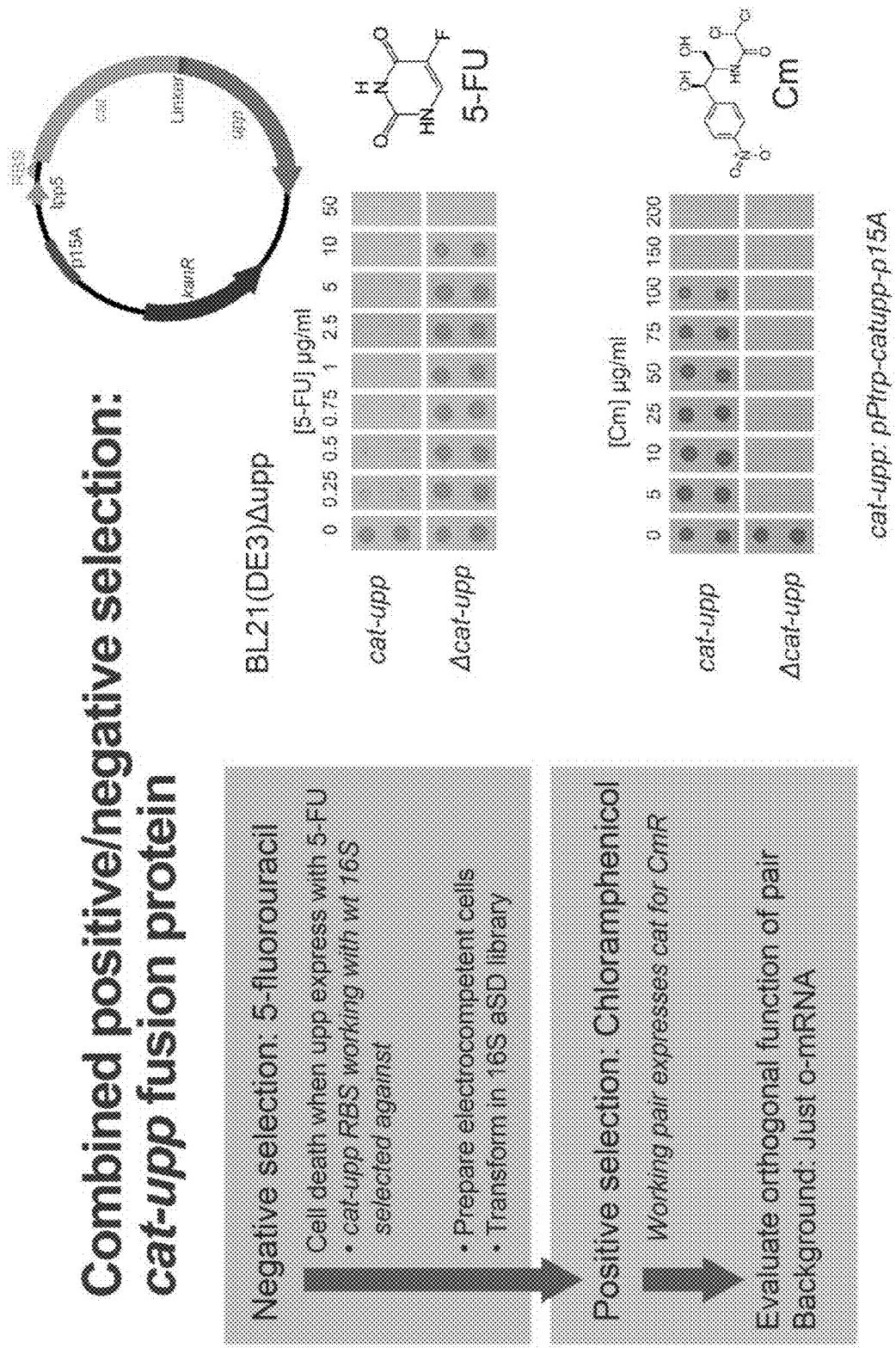
FIG. 20 shows a combined positive and negative selection scheme for evolving new orthogonal Shine-Dalgarno/anti-Shine-Dalgarno pairs. A. *E. coli* expressing cat-upp gene die in the presence of 5-Fluorouracil. B. *E. coli* expressing cat-upp gene gain resistance to the antibiotic chloramphenicol.
Figure 22:
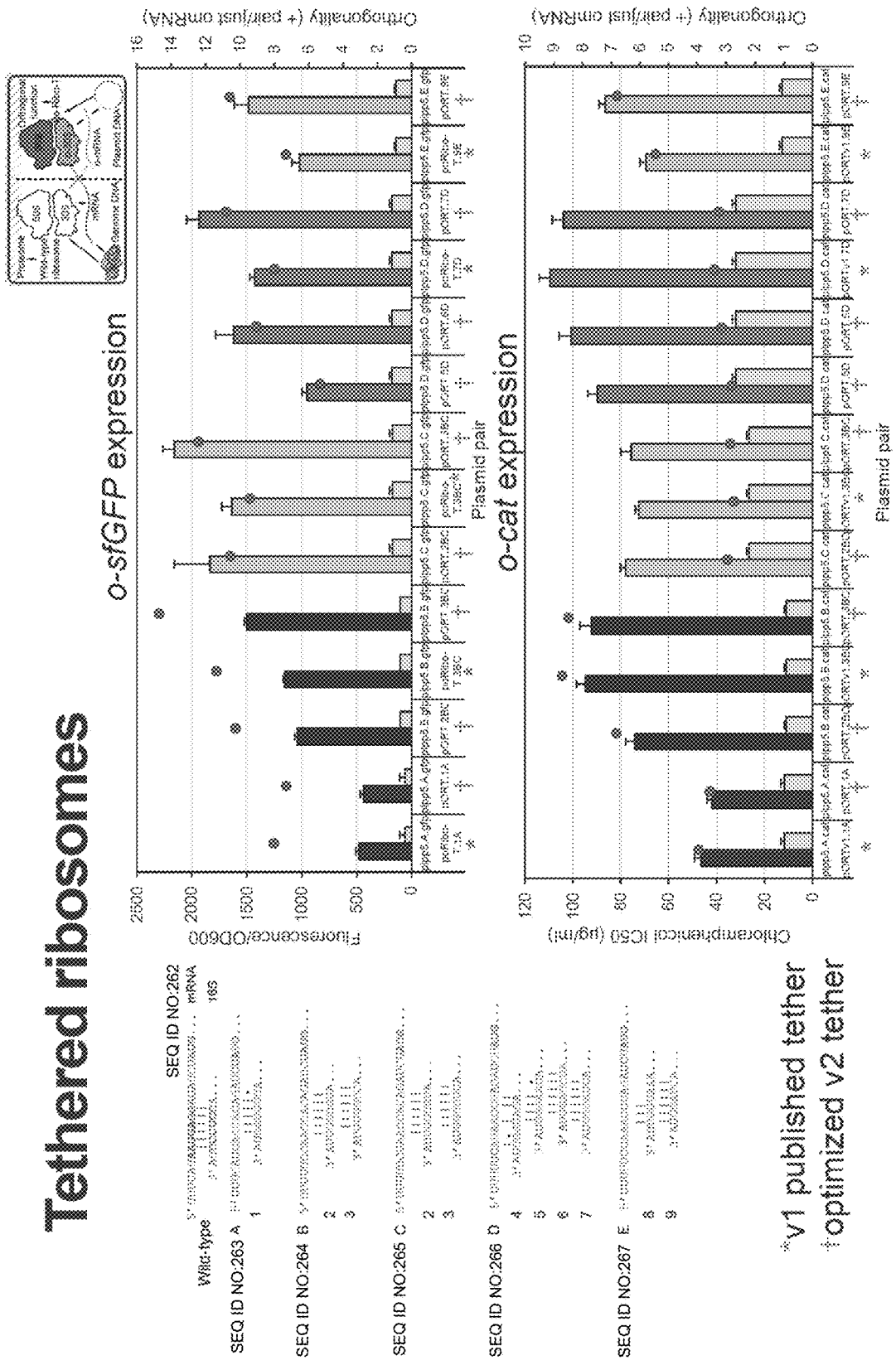
FIG. 22 shows testing of identified orthogonal pairs A, B, C, D, and E using tethered ribosomes Ribo-T-v1 (see Example 1) and Ribo-T-v2 (see FIG. 15G).

In this Example 2, improved orthogonal anti-Shine-Dalgarno/Shine-Dalgarno pairs (anti-SD/SD pairs) were selected in a BL21(DE3)Δupp strain using a positive/negative selection scheme based on a fusion of two genes: the upp gene, which produces a protein that causes cell death in the presence of the small molecule 5-fluorouracil (5-FU), and chloramphenicol acetyltransferase (cat) gene, which encodes for an enzyme that confers resistance to the antibiotic chloramphenicol (Cm) (See outline, scheme, and selection strategy of FIGS. 19 and 20). To identify orthogonal mRNA sequences not translated by the wild type ribosomes, a negative selection was performed in the presence of 5-FU (See FIG. 20). If the wild-type ribosome of cells transformed with the randomized SD mRNA library translate cat-upp, the UPP protein is produced which converts 5-FU to a toxin and cell death results. In surviving cells, cat-upp is not translated by the endogenous ribosome, indicating that any cat-upp mRNA expressed in the cell was not translated and suggesting that the cat-upp mRNA is orthogonal (i.e., that the cat-upp mRNA is not recognized by the endogenous ribosomes of the cell). The second selection step identifies ribosomes that can efficiently translate any orthogonal cat-upp mRNA. A randomized 16S anti-SD library of tethered ribosomes (Ribo-T) were transformed into cells surviving the negative selection above and the transformed cells were selected for Cm resistance (See FIG. 20). Only cells expressing the cat-upp fusion protein exhibit Cm resistance and survive the positive selection, indicating that the cat-upp mRNA was translated by the tethered ribosomes. (See FIG. 20). SD/anti-SD pairs that exhibited improved growth were isolated (FIGS. 21 and 22) and evaluated using a super-folder green fluorescent protein (sfGFP) expression system (FIG. 3A) and chloramphenicol acetyltransferase (cat) protein expression system (FIGS. 21 and 22). New orthogonal pairs were identified (FIGS. 21 and 22) that exhibited improved performance while maintaining or improving orthogonality (+ pair divided by just o-mRNA background).

Non-Standard Amino Acid Incorporation with Improved oRibo-T System

The single-plasmid coding for orthogonal Ribo-T and an orthogonal reporter gene were modified as follows. The Ribo-T operon was replaced with the improved orthogonal anti-SD sequence and improved tether sequences, or and untethered orthogonal ribosome for control. The sfGFP gene was cloned with either 2 or 5 TAG codons. Again, the pEVOL-pAzF plasmid containing the pAzF-tRNA synthetase and corresponding pAzF-tRNA mutated for TAG stop codon suppression was used [Young 2010].

Incorporating p-Azido-L-Phenylalanine into sfGFP-2TAG and STAG with Ribo-T

Figure 24:
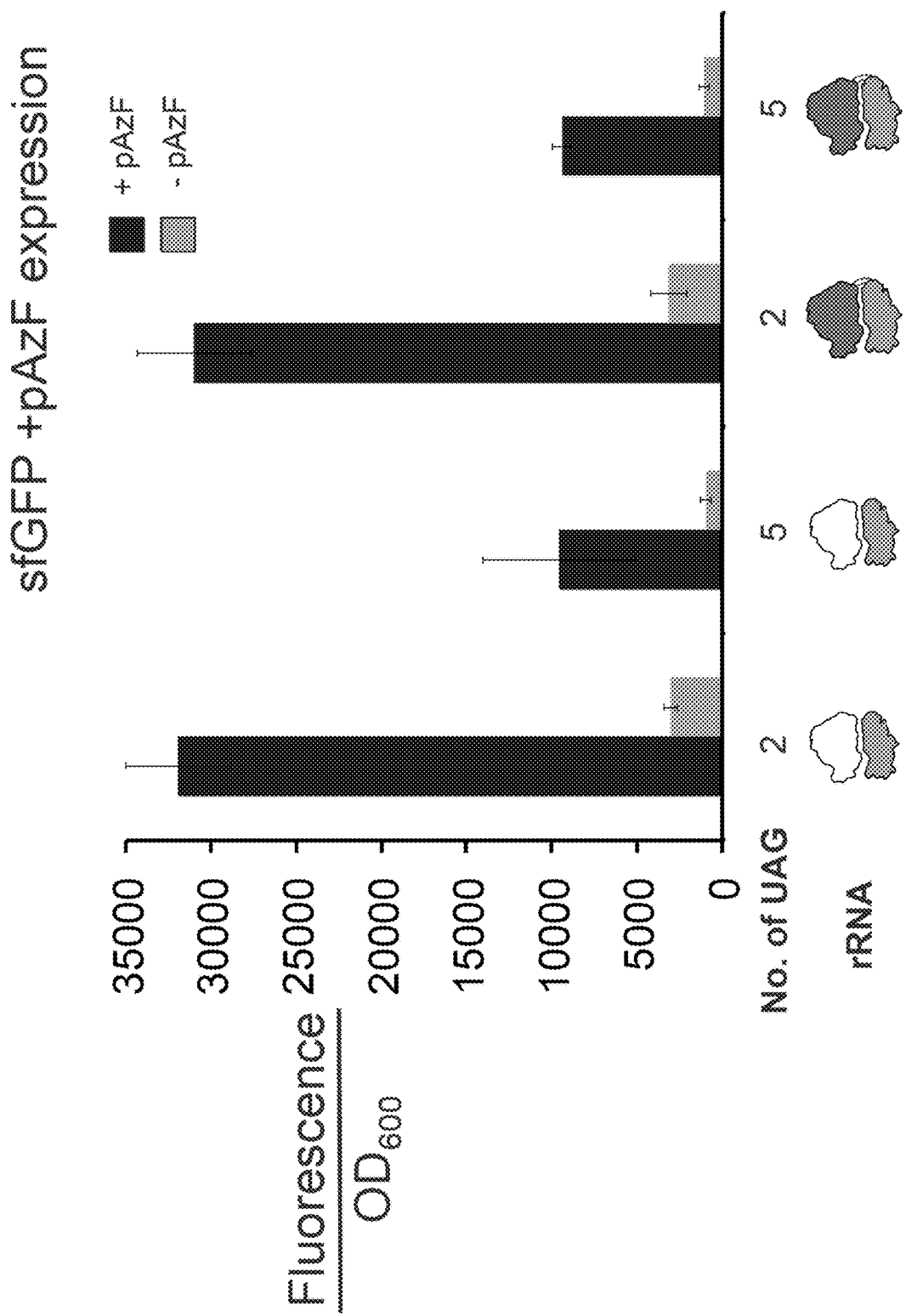
FIG. 24 illustrates the incorporation of pAzF into sfGFP at 2 or 5 UAG codon locations using improved orthogonal tethered ribosomes and pAzF-tRNA synthetases.

Plasmid oRibo-T-sfGFP with sfGFP gene modified with 2-TAG or 5-TAG as prepared in the example above under orthogonal SD site and variations to the oRibo-T portion of the plasmid was transformed into rEcoliΔ prfA mutS+upp-λ, red strain containing pEVOL-pAzF plasmid [Young 2010], and plated on LB agar plates supplemented with 50 µg/ml carbenicillin and 25 µg/ml chloramphenicol. Variants were randomly selected from a plate, and used to inoculate 100 µL LB supplemented with 50 µg/ml carbenicillin and 25 µg/ml chloramphenicol, and incubated overnight at 37° C. with shaking. A fresh 96-well plate (100 µL LB with 50 µg/ml carbenicillin, 25 µg/ml chloramphenicol, 1 mM IPTG and 0.02% L-arabinose) was inoculated with 2 µL of saturated overnight, and incubated at 37° C. with shaking for 18 hours, monitoring OD600 and sfGFP fluorescence. FIG. 24 shows sfGFP expression with and without pAzF in the media, with 2 or 5 TAG codons in the reporter gene, and untethered orthogonal ribosomes or orthogonal tethered ribosomes. Each condition was repeated at least three times. In all cases, expression of sfGFP with 2 or 5 TAG is significantly higher with pAzF added to the media, indicating incorporation of pAzF by the orthogonal ribosomes. The improved orthogonal tethered ribosome system performs comparatively to the untethered orthogonal system.

REFERENCES

An, W. & Chin, J. W. Synthesis of orthogonal transcription-translation networks. *Proc. Natl. Acad. Sci. USA* 106, 8477-8482 (2009).

Arenz, S. et al. Molecular basis for erythromycin-dependent ribosome stalling during translation of the ErmBL leader peptide. *Nature Commun.* 5, 3501 (2014).

Asai, T., Zaporojets, D., Squires, C. & Squires, C. L. An *Escherichia coli* strain with all chromosomal rRNA operons inactivated: complete exchange of rRNA genes between bacteria. *Proc. Natl. Acad. Sci. USA* 96, 1971-1976 (1999).

Bundy, B. C. & Swartz, J. R. Site-specific incorporation of p-propargyloxyphenylalanine in a cell-free environment for direct protein-protein click conjugation. *Bioconjugate Chem.* 21, 255-263 (2010).

Bhushan, S. et al. SecM-stalled ribosomes adopt an altered geometry at the peptidyl transferase center. *PLoS biology* 9, e1000581 (2011).

Cannone, J. J. et al. The Comparative RNA Web (CRW) Site: an online database of comparative sequence and structure information for ribosomal, intron, and other RNAs. *BMC Bioinform.* 3, 2. (2002).

Cruz-Vera, L. R. et al. Features of ribosome-peptidyl-tRNA interactions essential for tryptophan induction of tna operon expression. *Molec. Cell* 19, 333-343 (2005).

Dedkova, L. M. et al. Enhanced D-amino acid incorporation into protein by modified ribosomes. *Journal of the American Chemical Society* 125, 6616-6617 (2003).

Dorywalska, M. et al. Site-specific labeling of the ribosome for single-molecule spectroscopy. *Nucl. Acids Res.* 33, 182-189 (2005).

Dunkle, J. A. et al. Structures of the bacterial ribosome in classical and hybrid states of tRNA binding. *Science* 332, 981-984 (2011).

Erlacher, M. D. et al. Chemical engineering of the peptidyl transferase center reveals an important role of the 2'-hydroxyl group of A2451. *Nucl. Acids Res.* 33, 1618-1627 (2005).

Frank, J., and Agrawal, R. K. A ratchet-like inter-subunit reorganization of the ribosome during translocation. *Nature* 406, 318-322 (2000).

Fredrick, K., et al. Tagging ribosomal protein S7 allows rapid identification of mutants defective in assembly and function of 30 S subunits. *J. Mol. Biol.* 298, 379-394 (2000).

Gibson, D. G. et al. Enzymatic assembly of DNA molecules up to several hundred kilobases. *NatureMethods* 6, 343-345 (2009).

Horan, L. H., and Noller, H. F. Intersubunit movement is required for ribosomal translocation. *Proceedings of the National Academy of Sciences of the United States of America* 104, 4881-4885 (2007).

Hui, A., and de Boer, H. A. Specialized ribosome system: preferential translation of a single mRNA species by a subpopulation of mutated ribosomes in *Escherichia coli*. *Proceedings of the National Academy of Sciences of the United States of America* 84, 4762-4766 (1987).

Inouye, S. & Inouye, M. Up-promoter mutations in the lpp gene of *Escherichia coli*. *Nucl. Acids Res.* 13, 3101-3110 (1985).

Kannan, K., Vazquez-Laslop, N. & Mankin, A. S. Selective protein synthesis by ribosomes with a drug-obstructed exit tunnel. *Cell* 151, 508-520 (2012)

Karamyshev, A. L., et al. Transient idling of posttermination ribosomes ready to reinitiate protein synthesis. *Biochimie* 86, 933-938 (2004).

Karbstein, K. Quality control mechanisms during ribosome maturation. *Trends in cell biology* 23, 242-250 (2013).

Kitahara, K., and Suzuki, T. The ordered transcription of RNA domains is not essential for ribosome biogenesis in *Escherichia coli*. *Molecular cell* 34, 760-766 (2009).

Maini, R., et al. Incorporation of beta-amino acids into dihydrofolate reductase by ribosomes having modifications in the peptidyltransferase center. *Bioorganic & medicinal chemistry* 21, 1088-1096 (2013).

Mankin, A. S. Pactamycin resistance mutations in functional sites of 16S rRNA. *J. Mol. Biol.* 274, 8-15 (1997).

Marshall, R. A., et al. Irreversible chemical steps control intersubunit dynamics during translation. *Proceedings of the National Academy of Sciences of the United States of America* 105, 15364-15369 (2008).

Merryman, C. & Noller, H. F. in *RNA: Protein Interactions, A Practical Approach* (ed C. W. J. Smith) 237-253 (Oxford University Press, 1998).

Moll, I. et al. Translation initiation with 70S ribosomes: an alternative pathway for leaderless mRNAs. *Nucl. Acids Res.* 32, 3354-3363 (2004).

Myasnikov, A. G. et al. StructureFunction insights into prokaryotic and eukaryotic translation initiation. *Current opinion in structural biology* 19, 300-309 (2009).

Nakatogawa, H. & Ito, K. The ribosomal exit tunnel functions as a discriminating gate. *Cell* 108, 629-636 (2002).

Neumann, H. et al. Encoding multiple unnatural amino acids via evolution of a quadruplet-decoding ribosome. *Nature* 464, 441-444 (2010).

Nissen, P., et al. The structural basis of ribosome activity in peptide bond synthesis. *Science* 289, 920-930 (2000).

Nurenberg, E., and Tampe, R. Tying up loose ends: ribosome recycling in eukaryotes and archaea. *Trends in biochemical sciences* 38, 64-74 (2013).

Ohashi, H. et al. Efficient protein selection based on ribosome display system with purified components. *Biochem. Biophys. Res. Commun.* 352, 270-276 (2007).

Orelle, C. et al. Tools for characterizing bacterial protein synthesis inhibitors. *Antimicrobial agents and chemotherapy* 57, 5994-6004 (2013).

Orelle, C. et al. (Orelle 2) Identifying the targets of aminoacyl-tRNA synthetase inhibitors by primer extension inhibition. *Nucl. Acids Res.* 41, e144 (2013).

Pedelacq, J. D., Cabantous, S., Tran, T., Terwilliger, T. C. & Waldo, G. S. Engineering and characterization of a superfolder green fluorescent protein. *Nature Biotechnol.* 24, 79-88 (2006).

Petry, S. et al. The termination of translation. *Current opinion in structural biology* 18, 70-77 (2008).

Rackham, O., and Chin, J. W. A network of orthogonal ribosome×mRNA pairs. *Nature chemical biology* 1, 159-166 (2005).

Sato, N. S. et al. Comprehensive genetic selection revealed essential bases in the peptidyl-transferase center. *Proc. Natl. Acad. Sci. USA* 103, 15386-15391 (2006).

Schagger, H. & von Jagow, G. Tricine-sodium dodecyl sulfate-polyacrylamide gel electrophoresis for the separation of proteins in the range from 1 to 100 kDa. *Anal. Biochem.* 166, 368-379 (1987).

Schmeing, T. M., and Ramakrishnan, V. What recent ribosome structures have revealed about the mechanism of translation. *Nature* 461, 1234-1242 (2009).

Shimizu, Y. et al. Cell-free translation reconstituted with purified components. *Nature Biotechnol.* 19, 751-755 (2001).

Shimizu, Y., and Ueda, T. PURE technology. *Methods in molecular biology* 607, 11-21 (2010).

Thompson, J. et al. Analysis of mutations at residues A2451 and G2447 of 23S rRNA in the peptidyltransferase active site of the 50S ribosomal subunit. *Proc. Natl. Acad Sci. USA* 98, 9002-9007 (2001).

Thomason, L. C., Costantino, N. & Court, D. L. *E. coli* genome manipulation by P1 transduction. *Current Protocols in Molecular Biology*/edited by F M. Ausubel, et al. Chapter 1, Unit 1 17 (2007).

Vazquez-Laslop, Thum, C., & Mankin, A. S. Molecular mechanism of drug-dependent ribosome stalling *Mol. Cell* 30, 190-202 (2008).

Vazquez-Laslop, N. et al. The key role of a conserved and modified rRNA residue in the ribosomal response to the nascent peptide. *EMBO J.* 29, 3108-3117 (2010).

Voigts-Hoffmann, F. et al. Structural insights into eukaryotic ribosomes and the initiation of translation. *Current opinion in structural biology* 22, 768-777 (2012).

Voorhees, R. M., Weixlbaumer, A., Loakes, D., Kelley, A. C. & Ramakrishnan, V. Insights into substrate stabilization from snapshots of the peptidyl transferase center of the intact 70S ribosome. *Nat. Struct. Mol. Biol.* 16, 528-533 (2009).

Wang, K. et al. Evolved orthogonal ribosomes enhance the efficiency of synthetic genetic code expansion. *Nature biotechnology* 25, 770-777 (2007).

Young, T. S. et al. An Enhanced System for Unnatural Amino Acid Mutagenesis in *E. coli. Journal of molecular biology* 395, 361-374, (2010).

Yusupov, M. M. et al. Crystal structure of the ribosome at 5.5 A resolution. *Science* 292, 883-896 (2001).

Example 3—Tethered Ribosomes for Unnatural Amino Acid Incorporation

Abstract

Utilizing a previously improved version of an orthogonal ribosome with tethered subunits (oRibo-T-v2.0), we were motivated to find compelling applications in synthetic biology. Incorporation of non-standard amino acids hold much promise in studying and expanding the capabilities of proteins, and has not yet been shown to be possible with oRibo-T. For this reason, we here demonstrate that oRibo-T-v2.0 is readily apt at incorporating non-standard amino acids into proteins compared to an orthogonal ribosome without tethered subunits.

Applications

The disclosed subject matter has many applications, including but not limited to: ribosome evolution/engineering (for example towards more efficient non-canonical amino acid incorporation); enabling detailed in vivo studies of antibiotic resistance mechanisms and enabling antibiotic development process; and development of exotic genetic circuits that respond specifically to proteins containing non-standard amino acids translated by Ribo-T-v2.0.

Advantages

The disclosed subject matter discloses the range of functionalities of the improved Ribo-T system. Non-standard amino acid incorporation with Ribo-T has not previously been shown. Ribo-T's orthogonal 50S holds much promise for engineering the ribosome's catalytic peptidyl transferase center and exit tunnel for future incorporations of exotic monomers into proteins previously inaccessible by the wild-type ribosome.

Brief Summary

This example illustrates the application of Ribo-T-v2.0 for non-standard amino acid incorporation. This example discloses the incorporation of non-standard amino acid, specifically p-azido-L-phenylalanine (pAzF) with oRibo-T-v2.0. This example also discloses multiple, site-specific incorporation of pAzF (2 and 5 incorporations) with oRibo-T-v2.0. This example also discloses a combined rRNA-reporter plasmid system featuring the rRNA required for oRibo-T-v2.0 and the reporter protein on one plasmid. The subject matter of this example is further illustrated in FIG. 23 and FIG. 24.

REFERENCES

Chin, J.; Wang, K.; Neumann, H., Orthogonal Q-Ribosomes. U.S. Publication No. 2012/0264926.

Chin, J.; Wang, K.; Neumann, H., Evolved orthogonal ribosomes. U.S. Publication No. 20100105565.

Hui, A.; de Boer, H. A., Specialized ribosome system: preferential translation of a single mRNA species by a subpopulation of mutated ribosomes in *Escherichia coli*. Proceedings of the National Academy of Sciences 1987, 84 (14), 4762-4766.

Orelle, C.; Carlson, E. D.; Szal, T.; Florin, T.; Jewett, M. C.; Mankin, A. S., Protein synthesis by ribosomes with tethered subunits. *Nature* 2015, 524 (7563), 119-124.

Rackham, O.; Chin, J. W., Cellular Logic with Orthogonal Ribosomes. Journal of the American Chemical Society 2005, 127 (50), 17584-17585.

Rackham, O.; Chin, J. W., A network of orthogonal ribosome[middot]mRNA pairs. Nat Chem Biol 2005, 1 (3), 159-166.

Rackham, O.; Chin, J. W., Compositions and methods relating to orthogonal ribosome mRNA pairs. U.S. Publication No. 20090048434.

Wang, K.; Neumann, H.; Peak-Chew, S. Y.; Chin, J. W., Evolved orthogonal ribosomes enhance the efficiency of synthetic genetic code expansion. Nat Biotech 2007, 25 (7), 770-777.

In the foregoing description, it will be readily apparent to one skilled in the art that varying substitutions and modifications may be made to the invention disclosed herein without departing from the scope and spirit of the invention.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

What is claimed:

1. An engineered ribosome, the engineered ribosome comprising a small subunit, a large subunit, and a linking moiety, wherein the small subunit comprises ribosomal RNA (rRNA), wherein the large subunit comprises rRNA, and wherein the linking moiety tethers the rRNA of the small subunit with the rRNA of the large subunit, wherein the linking moiety comprises a polynucleotide sequence.

2. The engineered ribosome of claim 1, wherein the ribosome is capable of supporting translation of a sequence defined polymer.

3. The engineered ribosome of claim 1, wherein the small subunit comprises a modified anti-Shine-Dalgarno sequence to permit translation of templates having a complementary and/or cognate Shine-Dalgarno sequence different from endogenous cellular mRNAs.

4. The engineered ribosome of claim 3, wherein the small subunit comprises a modified anti-Shine-Dalgarno sequence selected from the group consisting of 3'-GGUGUU-5', 3'-UGGUGU-5', 3'-GGUGUC-5', 3'-GUUUAG-5', 3'-UGGAAU-5', 3'-GGAUCU-5', 3'-UGGAUC-5', 3'-UGGUAA-5', and 3'-UGGAUC-5'.

5. The engineered ribosome of claim 1, wherein the large subunit comprises a permuted variant or mutant of a 23S rRNA and/or the small subunit comprises a permuted variant or mutant of a 16S rRNA.

6. The engineered ribosome of claim 5, wherein the linking moiety covalently bonds a helix of the large subunit selected from the group consisting of helix 10, helix 38, helix 42, helix 54, helix 58, helix 63, helix 78, and helix 101 to a helix of the small subunit selected from the group consisting of helix 11, helix 26, helix 33, and helix 44.

7. The engineered ribosome of claim 6, wherein the linking moiety covalently bonds the helix 101 of the large subunit to the helix 44 of the small subunit.

8. The engineered ribosome of claim 1, wherein the large subunit comprises a first large subunit polynucleotide domain of 23S rRNA (namely a L1 polynucleotide domain), a connector polynucleotide domain of 23S rRNA (namely a C polynucleotide domain), and a second large subunit polynucleotide domain of 23S rRNA (namely a L2 polynucleotide domain), wherein the L1 polynucleotide domain is followed, in order, by the C polynucleotide domain and the L2 polynucleotide domain, from 5' to 3', and the L1 polynucleotide domain, the C polynucleotide domain, and the L2 polynucleotide domain together comprise the 23S rRNA polynucleotide.

9. The engineered ribosome of claim 1, wherein the small subunit comprises a first small subunit polynucleotide domain of 16S rRNA (namely a S1 polynucleotide domain) and a second small subunit polynucleotide domain of 16S rRNA (namely a S2 polynucleotide domain), wherein the S1 polynucleotide domain is followed, in order, by the S2 polynucleotide domain, from 5' to 3', and the S1 polynucleotide domain and the S2 polynucleotide domain together comprise the 16S rRNA polynucleotide.

10. The engineered ribosome of claim 8, wherein the linking moiety comprises a T1 polynucleotide domain and a T2 polynucleotide domain; and wherein: (i) the T1 polynucleotide domain links the S1 polynucleotide domain and the L1 polynucleotide domain and wherein the S1 polynucleotide domain is followed, in order, by the T1 polynucleotide domain and the L1 polynucleotide domain, from 5' to 3'; and (ii) the T2 polynucleotide domain links the S2 polynucleotide domain and the L2 polynucleotide domain and wherein the L2 polynucleotide domain is followed, in order, by the T2 polynucleotide domain and the S2 polynucleotide domain, from 5' to 3'.

11. The engineered ribosome of claim 10, wherein the T1 polynucleotide domain and a T2 polynucleotide domain comprise a polynucleotide sequence of FIG. 15 or 17.

12. The engineered ribosome of 10, wherein the ribosome comprises the S1 polynucleotide domain followed, in order, by the T1 polynucleotide domain, the L1 polynucleotide domain, the C polynucleotide domain, the L2 polynucleotide domain, the T2 polynucleotide domain, and the S2 polynucleotide domain, from 5' to 3'.

13. The engineered ribosome of claim 1, wherein the ribosome comprises a change-of-function mutation.

14. The engineered ribosome of claim 13, wherein the change-of-function mutation is selected from a change-of-function mutation in a peptidyl transferase center, a change-of-function mutation in the exit tunnel of the engineered ribosome, a change-of-function to the decoding center of the ribosome, a change-of-function mutation to an interaction site with elongation factors, a change-of-function mutation in tRNA binding sites, a change-of-function mutation in chaperone binding sites, a change-of-function mutation in nascent chain modifying enzyme binding sites, a change-of-function mutation in the GTPase center, and any combination thereof.

15. The engineered ribosome of claim 1, wherein the ribosome comprises an antibiotic resistance mutation.

16. A polynucleotide, the polynucleotide encoding the rRNA of the engineered ribosome of claim 1.

17. A plasmid comprising the polynucleotide of claim 16 and a reporter gene that is expressed and subsequently translated by an engineered ribosome comprising the encoded rRNA.

18. A kit comprising a plasmid, the plasmid comprising the polynucleotide of claim 16, and the kit further comprising one or more additional components for expressing and/or translating a target gene.

19. A cell comprising a first protein translation mechanism and a second protein translation mechanism, wherein the first protein translation mechanism comprises a ribosome, wherein the ribosome lacks a linking moiety between the large subunit and the small subunit and wherein the second protein translation mechanism comprises the engineered ribosome of claim 1.

20. A cell lacking a wild-type ribosome and comprising the engineered ribosome of claim 1.

21. A method for preparing a sequence-defined amino acid polymer, the method comprising (a) providing the engineered ribosome of claim 1; (b) providing an mRNA encoding the sequence-defined polymer; and (c) translating the mRNA with the engineered ribosome.

22. The method of claim 21, wherein the sequence-defined polymer is prepared in vitro.

23. The method of claim 21, wherein the sequence defined amino acid polymer is prepared in vivo.

24. The method of claim 21, wherein the amino acid amino acid polymer comprises one or more unnatural amino acids.

* * * * *

UNITED STATES PATENT AND TRADEMARK OFFICE
CERTIFICATE OF CORRECTION

PATENT NO. : 10,590,456 B2
APPLICATION NO. : 15/363828
DATED : March 17, 2020
INVENTOR(S) : Michael Christopher Jewett et al.

It is certified that error appears in the above-identified patent and that said Letters Patent is hereby corrected as shown below:

In the Specification

Column 1, Line 6, "(OP)" should be --(CIP)--.

Column 5, Line 10, "5150" should be --S150--.

Column 5, Line 15, "claim" should be --claims--.

Column 6, Line 7, "the A ribosome" should be --the Δ ribosome--.

Column 6, Line 11, "the A ribosome" should be --the Δ ribosome--.

Column 7, Lines 50-51, "subunit 101" should be --subunit rRNA 101--.

Column 8, Line 65, "the 51 domain" should be --the S1 domain--.

Column 17, Line 17, "5150" should be --S150--.

Column 30, Line 2, "11101" should be --(H101)--.

Column 30, Line 17, "11101" should be --H101--.

Column 30, Line 60, "11101" should be --H101--.

Column 35, Line 12, "T7FLAG-4" should be --T7FLAG™-4--.

Column 36, Line 5, "14 Ms" should be --14 hrs--.

Column 36, Line 21, "pAm552-Δ235-AflII" should be --pAm552-Δ23S-AflII--.

Signed and Sealed this
Seventeenth Day of August, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,590,456 B2

Column 47, Line 43, "2Ms" should be --2 hrs--.

Column 48, Line 44, "11101" should be --H101--.

Column 48, Line 58, "pAm552-Δ235-" should be --pAm552-Δ23S- --.

Column 48, Line 64, "pAm552-Δ235-AflII" should be --pAm552-Δ23S-AflII--.

Column 48, Line 66, "11101" should be --H101--.

Column 50, Line 4, "15 mM" should be --15 min--.

Column 50, Line 20, "30 mM" should be --30 min--.

Column 50, Line 40, "[$^{35}$5]" should be --[$^{35}$S]--.

Column 51, Line 57, "30 mM" should be --30 min--.

Column 53, Line 39, "lac/gene" should be --lacI gene--.

Column 56, Line 21, "24 Ms" should be --24 hrs--.

Column 57, Line 4, "STAG" should be --5TAG--.

Column 58, Line 60, "STAG" should be --5TAG--.

SEQUENCE LISTING

```
<160> NUMBER OF SEQ ID NOS: 267

<210> SEQ ID NO 1
<211> LENGTH: 18
<212> TYPE: DNA
<213> ORGANISM: Artificial Sequence
<220> FEATURE:
<223> OTHER INFORMATION: Synthetic primer

<400> SEQUENCE: 1
ccgtcttgcc gcgggtac                                                       18

<210> SEQ ID NO 2
<211> LENGTH: 36
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (3)..(20)
<223> OTHER INFORMATION: complementary sequence
<220> FEATURE:
<221> NAME/KEY: misc_feature
<222> LOCATION: (21)..(21)
<223> OTHER INFORMATION: a2058g mutation

<400> SEQUENCE: 2
gtgtacccgc ggcaagacgg gaagacccccg tgaacc                                  36

<210> SEQ ID NO 3
<211> LENGTH: 18
<212> TYPE: DNA
<213> ORGANISM: Artificial Sequence
<220> FEATURE:
<223> OTHER INFORMATION: Synthetic Primer

<400> SEQUENCE: 3
ggttaagcct cacggttc                                                       18

<210> SEQ ID NO 4
<211> LENGTH: 39
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(15)
<223> OTHER INFORMATION: complementary sequence
<220> FEATURE:
<221> NAME/KEY: misc_feature
<222> LOCATION: (16)..(19)
<223> OTHER INFORMATION: gaga loop

<400> SEQUENCE: 4
```

```
ccgtgaggct taaccgagag gttaagcgac taagcgtac                              39

<210> SEQ ID NO 5
<211> LENGTH: 36
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(19)
<223> OTHER INFORMATION: added homology to T7FLAG(TM)-4 vector

<400> SEQUENCE: 5
gagacacaac gtggctttcc ggccgtaact ataacg                                 36

<210> SEQ ID NO 6
<211> LENGTH: 35
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<223> OTHER INFORMATION: added homology to the T7FLAG(TM)-4 vector

<400> SEQUENCE: 6
cactcgtcga gatcgatctt cggccgccgt ttacc                                  35

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
aagatcgatc tcgacgagtg                                                   20

<210> SEQ ID NO 8
<211> LENGTH: 19
<212> TYPE: DNA
<213> ORGANISM: Artificial Sequence
<220> FEATURE:
<223> OTHER INFORMATION: Synthetic primer

<400> SEQUENCE: 8
gaaagccacg ttgtgtctc                                                    19

<210> SEQ ID NO 9
<211> LENGTH: 40
<212> TYPE: DNA
<213> ORGANISM: Artificial Sequence
<220> FEATURE:
<223> OTHER INFORMATION: Synthetic primer

<400> SEQUENCE: 9
aacatcttcg ggttgtgagc ttaagctgcg ataagcgtcg                             40

<210> SEQ ID NO 10
<211> LENGTH: 40
<212> TYPE: DNA
<213> ORGANISM: Artificial Sequence
<220> FEATURE:
<223> OTHER INFORMATION: Synthetic primer

<400> SEQUENCE: 10
```
acagcttcgg cgttgtaagc ttaagccacg tccttcatcg    40

<210> SEQ ID NO 11
<211> LENGTH: 47
<212> TYPE: DNA
<213> ORGANISM: Artificial Sequence
<220> FEATURE:
<223> OTHER INFORMATION: Synthetic primer

<400> SEQUENCE: 11
aacatcttcg ggttgtgagc ttaagcaccg ttataaccgg cgatttc    47

<210> SEQ ID NO 12
<211> LENGTH: 44
<212> TYPE: DNA
<213> ORGANISM: Artificial Sequence
<220> FEATURE:
<223> OTHER INFORMATION: Synthetic primer

<400> SEQUENCE: 12
acagcttcgg cgttgtaagc ttaagcacct taccgacgct tatc    44

<210> SEQ ID NO 13
<211> LENGTH: 40
<212> TYPE: DNA
<213> ORGANISM: Artificial Sequence
<220> FEATURE:
<223> OTHER INFORMATION: Synthetic primer

<400> SEQUENCE: 13
aacatcttcg ggttgtgagc ttaagcaccg gcgatttccg    40

<210> SEQ ID NO 14
<211> LENGTH: 44
<212> TYPE: DNA
<213> ORGANISM: Artificial Sequence
<220> FEATURE:
<223> OTHER INFORMATION: Synthetic primer

<400> SEQUENCE: 14
acagcttcgg cgttgtaagc ttaagcggtt catatcacct tacc    44

<210> SEQ ID NO 15
<211> LENGTH: 42
<212> TYPE: DNA
<213> ORGANISM: Artificial Sequence
<220> FEATURE:
<223> OTHER INFORMATION: Synthetic primer

<400> SEQUENCE: 15
aacatcttcg ggttgtgagc ttaagcccca gtgtgtttcg ac    42

<210> SEQ ID NO 16
<211> LENGTH: 41
<212> TYPE: DNA
<213> ORGANISM: Artificial Sequence
<220> FEATURE:
<223> OTHER INFORMATION: Synthetic primer

<400> SEQUENCE: 16
acagcttcgg cgttgtaagc ttaagcccca ttcggaaatc g    41

<210> SEQ ID NO 17
<211> LENGTH: 48
<212> TYPE: DNA

<213> ORGANISM: Artificial Sequence
<220> FEATURE:
<223> OTHER INFORMATION: Synthetic primer

<400> SEQUENCE: 17
aacatcttcg ggttgtgagc ttaagcacac actatcatta actgaatc        48

<210> SEQ ID NO 18
<211> LENGTH: 41
<212> TYPE: DNA
<213> ORGANISM: Artificial Sequence
<220> FEATURE:
<223> OTHER INFORMATION: Synthetic primer

<400> SEQUENCE: 18
acagcttcgg cgttgtaagc ttaagcacac actgggtttc c        41

<210> SEQ ID NO 19
<211> LENGTH: 42
<212> TYPE: DNA
<213> ORGANISM: Artificial Sequence
<220> FEATURE:
<223> OTHER INFORMATION: Synthetic primer

<400> SEQUENCE: 19
aacatcttcg ggttgtgagc ttaagcggtt aatgaggcga ac        42

<210> SEQ ID NO 20
<211> LENGTH: 44
<212> TYPE: DNA
<213> ORGANISM: Artificial Sequence
<220> FEATURE:
<223> OTHER INFORMATION: Synthetic primer

<400> SEQUENCE: 20
acagcttcgg cgttgtaagc ttaagcagtt aatgatagtg tgtc        44

<210> SEQ ID NO 21
<211> LENGTH: 42
<212> TYPE: DNA
<213> ORGANISM: Artificial Sequence
<220> FEATURE:
<223> OTHER INFORMATION: Synthetic primer

<400> SEQUENCE: 21
aacatcttcg ggttgtgagc ttaagctcta agtaccccga gg        42

<210> SEQ ID NO 22
<211> LENGTH: 42
<212> TYPE: DNA
<213> ORGANISM: Artificial Sequence
<220> FEATURE:
<223> OTHER INFORMATION: Synthetic primer

<400> SEQUENCE: 22
acagcttcgg cgttgtaagc ttaagctcag ttcccccggt tc        42

<210> SEQ ID NO 23
<211> LENGTH: 42
<212> TYPE: DNA
<213> ORGANISM: Artificial Sequence
<220> FEATURE:
<223> OTHER INFORMATION: Synthetic primer

<400> SEQUENCE: 23
aacatcttcg ggttgtgagc ttaagcgaga ttcccccagt ag        42

<210> SEQ ID NO 24
<211> LENGTH: 47
<212> TYPE: DNA
<213> ORGANISM: Artificial Sequence
<220> FEATURE:
<223> OTHER INFORMATION: Synthetic primer

<400> SEQUENCE: 24
acagcttcgg cgttgtaagc ttaagcgatt tcttttcctc ggggtac    47

<210> SEQ ID NO 25
<211> LENGTH: 41
<212> TYPE: DNA
<213> ORGANISM: Artificial Sequence
<220> FEATURE:
<223> OTHER INFORMATION: Synthetic primer

<400> SEQUENCE: 25
aacatcttcg ggttgtgagc ttaagcgcga acggggagca g    41

<210> SEQ ID NO 26
<211> LENGTH: 43
<212> TYPE: DNA
<213> ORGANISM: Artificial Sequence
<220> FEATURE:
<223> OTHER INFORMATION: Synthetic primer

<400> SEQUENCE: 26
acagcttcgg cgttgtaagc ttaagcgcta ctgggggaat ctc    43

<210> SEQ ID NO 27
<211> LENGTH: 43
<212> TYPE: DNA
<213> ORGANISM: Artificial Sequence
<220> FEATURE:
<223> OTHER INFORMATION: Synthetic primer

<400> SEQUENCE: 27
aacatcttcg ggttgtgagc ttaagccagt gtgtgtgtta gtg    43

<210> SEQ ID NO 28
<211> LENGTH: 40
<212> TYPE: DNA
<213> ORGANISM: Artificial Sequence
<220> FEATURE:
<223> OTHER INFORMATION: Synthetic primer

<400> SEQUENCE: 28
acagcttcgg cgttgtaagc ttaagcgctc tgggctgctc    40

<210> SEQ ID NO 29
<211> LENGTH: 40
<212> TYPE: DNA
<213> ORGANISM: Artificial Sequence
<220> FEATURE:
<223> OTHER INFORMATION: Synthetic primer

<400> SEQUENCE: 29
aacatcttcg ggttgtgagc ttaagcggcg cgcgatacag    40

<210> SEQ ID NO 30
<211> LENGTH: 43
<212> TYPE: DNA
<213> ORGANISM: Artificial Sequence
<220> FEATURE:

<223> OTHER INFORMATION: Synthetic primer

<400> SEQUENCE: 30
acagcttcgg cgttgtaagc ttaagcgacg cttccactaa cac       43

<210> SEQ ID NO 31
<211> LENGTH: 45
<212> TYPE: DNA
<213> ORGANISM: Artificial Sequence
<220> FEATURE:
<223> OTHER INFORMATION: Synthetic primer

<400> SEQUENCE: 31
aacatcttcg ggttgtgagc ttaagccccg tacacaaaaa tgcac       45

<210> SEQ ID NO 32
<211> LENGTH: 46
<212> TYPE: DNA
<213> ORGANISM: Artificial Sequence
<220> FEATURE:
<223> OTHER INFORMATION: Synthetic primer

<400> SEQUENCE: 32
acagcttcgg cgttgtaagc ttaagcccct gtatcgcgcg cctttc       46

<210> SEQ ID NO 33
<211> LENGTH: 43
<212> TYPE: DNA
<213> ORGANISM: Artificial Sequence
<220> FEATURE:
<223> OTHER INFORMATION: Synthetic primer

<400> SEQUENCE: 33
aacatcttcg ggttgtgagc ttaagcaatg cacatgctgt gag       43

<210> SEQ ID NO 34
<211> LENGTH: 41
<212> TYPE: DNA
<213> ORGANISM: Artificial Sequence
<220> FEATURE:
<223> OTHER INFORMATION: Synthetic primer

<400> SEQUENCE: 34
acagcttcgg cgttgtaagc ttaagcgtgt acggggctgt c       41

<210> SEQ ID NO 35
<211> LENGTH: 43
<212> TYPE: DNA
<213> ORGANISM: Artificial Sequence
<220> FEATURE:
<223> OTHER INFORMATION: Synthetic primer

<400> SEQUENCE: 35
aacatcttcg ggttgtgagc ttaagcatcc tgtctgaata tgg       43

<210> SEQ ID NO 36
<211> LENGTH: 40
<212> TYPE: DNA
<213> ORGANISM: Artificial Sequence
<220> FEATURE:
<223> OTHER INFORMATION: Synthetic primer

<400> SEQUENCE: 36
acagcttcgg cgttgtaagc ttaagcgtcc cgccctactc       40

<210> SEQ ID NO 37
<211> LENGTH: 44
<212> TYPE: DNA
<213> ORGANISM: Artificial Sequence
<220> FEATURE:
<223> OTHER INFORMATION: Synthetic primer

<400> SEQUENCE: 37
aacatcttcg ggttgtgagc ttaagctcct ccaaggctaa atac                44

<210> SEQ ID NO 38
<211> LENGTH: 44
<212> TYPE: DNA
<213> ORGANISM: Artificial Sequence
<220> FEATURE:
<223> OTHER INFORMATION: Synthetic primer

<400> SEQUENCE: 38
acagcttcgg cgttgtaagc ttaagccccc ccatattcag acag                44

<210> SEQ ID NO 39
<211> LENGTH: 44
<212> TYPE: DNA
<213> ORGANISM: Artificial Sequence
<220> FEATURE:
<223> OTHER INFORMATION: Synthetic primer

<400> SEQUENCE: 39
aacatcttcg ggttgtgagc ttaagcggga aggcgaaaa gaac                 44

<210> SEQ ID NO 40
<211> LENGTH: 44
<212> TYPE: DNA
<213> ORGANISM: Artificial Sequence
<220> FEATURE:
<223> OTHER INFORMATION: Synthetic primer

<400> SEQUENCE: 40
acagcttcgg cgttgtaagc ttaagcggta ctggttcact atcg                44

<210> SEQ ID NO 41
<211> LENGTH: 43
<212> TYPE: DNA
<213> ORGANISM: Artificial Sequence
<220> FEATURE:
<223> OTHER INFORMATION: Synthetic primer

<400> SEQUENCE: 41
aacatcttcg ggttgtgagc ttaagcgggg agtgaaaaag aac                 43

<210> SEQ ID NO 42
<211> LENGTH: 45
<212> TYPE: DNA
<213> ORGANISM: Artificial Sequence
<220> FEATURE:
<223> OTHER INFORMATION: Synthetic primer

<400> SEQUENCE: 42
acagcttcgg cgttgtaagc ttaagcgggg ttcttttcgc ctttc               45

<210> SEQ ID NO 43
<211> LENGTH: 45
<212> TYPE: DNA
<213> ORGANISM: Artificial Sequence
<220> FEATURE:
<223> OTHER INFORMATION: Synthetic primer

<400> SEQUENCE: 43
aacatcttcg ggttgtgagc ttaagcaaaa gaacctgaaa ccgtg        45

<210> SEQ ID NO 44
<211> LENGTH: 43
<212> TYPE: DNA
<213> ORGANISM: Artificial Sequence
<220> FEATURE:
<223> OTHER INFORMATION: Synthetic primer

<400> SEQUENCE: 44
acagcttcgg cgttgtaagc ttaagctccc ctcgccgggg ttc        43

<210> SEQ ID NO 45
<211> LENGTH: 43
<212> TYPE: DNA
<213> ORGANISM: Artificial Sequence
<220> FEATURE:
<223> OTHER INFORMATION: Synthetic primer

<400> SEQUENCE: 45
aacatcttcg ggttgtgagc ttaagcgcgt gtgactgcgt acc        43

<210> SEQ ID NO 46
<211> LENGTH: 40
<212> TYPE: DNA
<213> ORGANISM: Artificial Sequence
<220> FEATURE:
<223> OTHER INFORMATION: Synthetic primer

<400> SEQUENCE: 46
acagcttcgg cgttgtaagc ttaagcgcgt gctcccactg        40

<210> SEQ ID NO 47
<211> LENGTH: 39
<212> TYPE: DNA
<213> ORGANISM: Artificial Sequence
<220> FEATURE:
<223> OTHER INFORMATION: Synthetic primer

<400> SEQUENCE: 47
aacatcttcg ggttgtgagc ttaagcgggg agccgaagg        39

<210> SEQ ID NO 48
<211> LENGTH: 43
<212> TYPE: DNA
<213> ORGANISM: Artificial Sequence
<220> FEATURE:
<223> OTHER INFORMATION: Synthetic primer

<400> SEQUENCE: 48
acagcttcgg cgttgtaagc ttaagcggtt aaccttgcta cag        43

<210> SEQ ID NO 49
<211> LENGTH: 41
<212> TYPE: DNA
<213> ORGANISM: Artificial Sequence
<220> FEATURE:
<223> OTHER INFORMATION: Synthetic primer

<400> SEQUENCE: 49
aacatcttcg ggttgtgagc ttaagcccga gtcttaactg g        41

<210> SEQ ID NO 50
<211> LENGTH: 44

```
<212> TYPE: DNA
<213> ORGANISM: Artificial Sequence
<220> FEATURE:
<223> OTHER INFORMATION: Synthetic primer

<400> SEQUENCE: 50
acagcttcgg cgttgtaagc ttaagccctt cggctcccct attc         44

<210> SEQ ID NO 51
<211> LENGTH: 43
<212> TYPE: DNA
<213> ORGANISM: Artificial Sequence
<220> FEATURE:
<223> OTHER INFORMATION: Synthetic primer

<400> SEQUENCE: 51
aacatcttcg ggttgtgagc ttaagcgggc gttaagttgc agg          43

<210> SEQ ID NO 52
<211> LENGTH: 43
<212> TYPE: DNA
<213> ORGANISM: Artificial Sequence
<220> FEATURE:
<223> OTHER INFORMATION: Synthetic primer

<400> SEQUENCE: 52
acagcttcgg cgttgtaagc ttaagcagac tcggtttccc ttc          43

<210> SEQ ID NO 53
<211> LENGTH: 40
<212> TYPE: DNA
<213> ORGANISM: Artificial Sequence
<220> FEATURE:
<223> OTHER INFORMATION: Synthetic primer

<400> SEQUENCE: 53
aacatcttcg ggttgtgagc ttaagcctaa ctggaggacc             40

<210> SEQ ID NO 54
<211> LENGTH: 41
<212> TYPE: DNA
<213> ORGANISM: Artificial Sequence
<220> FEATURE:
<223> OTHER INFORMATION: Synthetic primer

<400> SEQUENCE: 54
acagcttcgg cgttgtaagc ttaagcccaa ccttcaacct g           41

<210> SEQ ID NO 55
<211> LENGTH: 44
<212> TYPE: DNA
<213> ORGANISM: Artificial Sequence
<220> FEATURE:
<223> OTHER INFORMATION: Synthetic primer

<400> SEQUENCE: 55
aacatcttcg ggttgtgagc ttaagcatta gcggatgact tgtg        44

<210> SEQ ID NO 56
<211> LENGTH: 43
<212> TYPE: DNA
<213> ORGANISM: Artificial Sequence
<220> FEATURE:
<223> OTHER INFORMATION: Synthetic primer

<400> SEQUENCE: 56
```

```
acagcttcgg cgttgtaagc ttaagcatta gtcggttcgg tcc        43

<210> SEQ ID NO 57
<211> LENGTH: 43
<212> TYPE: DNA
<213> ORGANISM: Artificial Sequence
<220> FEATURE:
<223> OTHER INFORMATION: Synthetic primer

<400> SEQUENCE: 57
aacatcttcg ggttgtgagc ttaagcgcca atcaaaccgg gag        43

<210> SEQ ID NO 58
<211> LENGTH: 41
<212> TYPE: DNA
<213> ORGANISM: Artificial Sequence
<220> FEATURE:
<223> OTHER INFORMATION: Synthetic primer

<400> SEQUENCE: 58
acagcttcgg cgttgtaagc ttaagcaccc ccagccacaa g          41

<210> SEQ ID NO 59
<211> LENGTH: 44
<212> TYPE: DNA
<213> ORGANISM: Artificial Sequence
<220> FEATURE:
<223> OTHER INFORMATION: Synthetic primer

<400> SEQUENCE: 59
aacatcttcg ggttgtgagc ttaagcgtag cgcctcgtga attc       44

<210> SEQ ID NO 60
<211> LENGTH: 45
<212> TYPE: DNA
<213> ORGANISM: Artificial Sequence
<220> FEATURE:
<223> OTHER INFORMATION: Synthetic primer

<400> SEQUENCE: 60
acagcttcgg cgttgtaagc ttaagcatag ctttcgggga gaacc      45

<210> SEQ ID NO 61
<211> LENGTH: 41
<212> TYPE: DNA
<213> ORGANISM: Artificial Sequence
<220> FEATURE:
<223> OTHER INFORMATION: Synthetic primer

<400> SEQUENCE: 61
aacatcttcg ggttgtgagc ttaagcgggg gtcatcccga c          41

<210> SEQ ID NO 62
<211> LENGTH: 44
<212> TYPE: DNA
<213> ORGANISM: Artificial Sequence
<220> FEATURE:
<223> OTHER INFORMATION: Synthetic primer

<400> SEQUENCE: 62
acagcttcgg cgttgtaagc ttaagcccga aacagtgctc tacc       44

<210> SEQ ID NO 63
<211> LENGTH: 43
<212> TYPE: DNA
<213> ORGANISM: Artificial Sequence
```

<220> FEATURE:
<223> OTHER INFORMATION: Synthetic primer

<400> SEQUENCE: 63
aacatcttcg ggttgtgagc ttaagcgact taccaacccg atg           43

<210> SEQ ID NO 64
<211> LENGTH: 43
<212> TYPE: DNA
<213> ORGANISM: Artificial Sequence
<220> FEATURE:
<223> OTHER INFORMATION: Synthetic primer

<400> SEQUENCE: 64
acagcttcgg cgttgtaagc ttaagcgacc cccttgccga aac           43

<210> SEQ ID NO 65
<211> LENGTH: 42
<212> TYPE: DNA
<213> ORGANISM: Artificial Sequence
<220> FEATURE:
<223> OTHER INFORMATION: Synthetic primer

<400> SEQUENCE: 65
aacatcttcg ggttgtgagc ttaagcgtcc gtcgtgaaga gg            42

<210> SEQ ID NO 66
<211> LENGTH: 40
<212> TYPE: DNA
<213> ORGANISM: Artificial Sequence
<220> FEATURE:
<223> OTHER INFORMATION: Synthetic primer

<400> SEQUENCE: 66
acagcttcgg cgttgtaagc ttaagcaccc gccgtgtgtc               40

<210> SEQ ID NO 67
<211> LENGTH: 40
<212> TYPE: DNA
<213> ORGANISM: Artificial Sequence
<220> FEATURE:
<223> OTHER INFORMATION: Synthetic primer

<400> SEQUENCE: 67
aacatcttcg ggttgtgagc ttaagcccca gaccgccagc               40

<210> SEQ ID NO 68
<211> LENGTH: 43
<212> TYPE: DNA
<213> ORGANISM: Artificial Sequence
<220> FEATURE:
<223> OTHER INFORMATION: Synthetic primer

<400> SEQUENCE: 68
acagcttcgg cgttgtaagc ttaagcccct cttcacgacg gac           43

<210> SEQ ID NO 69
<211> LENGTH: 46
<212> TYPE: DNA
<213> ORGANISM: Artificial Sequence
<220> FEATURE:
<223> OTHER INFORMATION: Synthetic primer

<400> SEQUENCE: 69
aacatcttcg ggttgtgagc ttaagcgtca tggttaagtg ggaaac        46

<210> SEQ ID NO 70
<211> LENGTH: 42
<212> TYPE: DNA
<213> ORGANISM: Artificial Sequence
<220> FEATURE:
<223> OTHER INFORMATION: Synthetic primer

<400> SEQUENCE: 70
acagcttcgg cgttgtaagc ttaagcacct tagctggcgg tc					42

<210> SEQ ID NO 71
<211> LENGTH: 44
<212> TYPE: DNA
<213> ORGANISM: Artificial Sequence
<220> FEATURE:
<223> OTHER INFORMATION: Synthetic primer

<400> SEQUENCE: 71
aacatcttcg ggttgtgagc ttaagcgcca ggatgttggc ttag					44

<210> SEQ ID NO 72
<211> LENGTH: 44
<212> TYPE: DNA
<213> ORGANISM: Artificial Sequence
<220> FEATURE:
<223> OTHER INFORMATION: Synthetic primer

<400> SEQUENCE: 72
acagcttcgg cgttgtaagc ttaagcgcct tcccacatcg tttc					44

<210> SEQ ID NO 73
<211> LENGTH: 45
<212> TYPE: DNA
<213> ORGANISM: Artificial Sequence
<220> FEATURE:
<223> OTHER INFORMATION: Synthetic primer

<400> SEQUENCE: 73
aacatcttcg ggttgtgagc ttaagcgcca tcatttaaag aaagc					45

<210> SEQ ID NO 74
<211> LENGTH: 42
<212> TYPE: DNA
<213> ORGANISM: Artificial Sequence
<220> FEATURE:
<223> OTHER INFORMATION: Synthetic primer

<400> SEQUENCE: 74
acagcttcgg cgttgtaagc ttaagcgcca acatcctggc tg					42

<210> SEQ ID NO 75
<211> LENGTH: 45
<212> TYPE: DNA
<213> ORGANISM: Artificial Sequence
<220> FEATURE:
<223> OTHER INFORMATION: Synthetic primer

<400> SEQUENCE: 75
aacatcttcg ggttgtgagc ttaagcagaa agcgtaatag ctcac					45

<210> SEQ ID NO 76
<211> LENGTH: 45
<212> TYPE: DNA
<213> ORGANISM: Artificial Sequence
<220> FEATURE:
<223> OTHER INFORMATION: Synthetic primer

```
<400> SEQUENCE: 76
acagcttcgg cgttgtaagc ttaagcaatg atggctgctt ctaag        45

<210> SEQ ID NO 77
<211> LENGTH: 40
<212> TYPE: DNA
<213> ORGANISM: Artificial Sequence
<220> FEATURE:
<223> OTHER INFORMATION: Synthetic primer

<400> SEQUENCE: 77
aacatcttcg ggttgtgagc ttaagcgctc actggtcgag             40

<210> SEQ ID NO 78
<211> LENGTH: 47
<212> TYPE: DNA
<213> ORGANISM: Artificial Sequence
<220> FEATURE:
<223> OTHER INFORMATION: Synthetic primer

<400> SEQUENCE: 78
acagcttcgg cgttgtaagc ttaagcgctt tctttaaatg atggctg      47

<210> SEQ ID NO 79
<211> LENGTH: 43
<212> TYPE: DNA
<213> ORGANISM: Artificial Sequence
<220> FEATURE:
<223> OTHER INFORMATION: Synthetic primer

<400> SEQUENCE: 79
aacatcttcg ggttgtgagc ttaagcgtcg gcctgcgcgg aag          43

<210> SEQ ID NO 80
<211> LENGTH: 48
<212> TYPE: DNA
<213> ORGANISM: Artificial Sequence
<220> FEATURE:
<223> OTHER INFORMATION: Synthetic primer

<400> SEQUENCE: 80
acagcttcgg cgttgtaagc ttaagcacca gtgagctatt acgctttc     48

<210> SEQ ID NO 81
<211> LENGTH: 41
<212> TYPE: DNA
<213> ORGANISM: Artificial Sequence
<220> FEATURE:
<223> OTHER INFORMATION: Synthetic primer

<400> SEQUENCE: 81
aacatcttcg ggttgtgagc ttaagcgcgt tgttgggtag g            41

<210> SEQ ID NO 82
<211> LENGTH: 37
<212> TYPE: DNA
<213> ORGANISM: Artificial Sequence
<220> FEATURE:
<223> OTHER INFORMATION: Synthetic primer

<400> SEQUENCE: 82
acagcttcgg cgttgtaagc ttaagcgcgt cgctgcc                 37

<210> SEQ ID NO 83
```

```
<211> LENGTH: 40
<212> TYPE: DNA
<213> ORGANISM: Artificial Sequence
<220> FEATURE:
<223> OTHER INFORMATION: Synthetic primer

<400> SEQUENCE: 83
aacatcttcg ggttgtgagc ttaagcggtg tgctgtgagg                        40

<210> SEQ ID NO 84
<211> LENGTH: 42
<212> TYPE: DNA
<213> ORGANISM: Artificial Sequence
<220> FEATURE:
<223> OTHER INFORMATION: Synthetic primer

<400> SEQUENCE: 84
acagcttcgg cgttgtaagc ttaagcggct tacagaacgc tc                     42

<210> SEQ ID NO 85
<211> LENGTH: 39
<212> TYPE: DNA
<213> ORGANISM: Artificial Sequence
<220> FEATURE:
<223> OTHER INFORMATION: Synthetic primer

<400> SEQUENCE: 85
aacatcttcg ggttgtgagc ttaagcggca tgctggagg                         39

<210> SEQ ID NO 86
<211> LENGTH: 41
<212> TYPE: DNA
<213> ORGANISM: Artificial Sequence
<220> FEATURE:
<223> OTHER INFORMATION: Synthetic primer

<400> SEQUENCE: 86
acagcttcgg cgttgtaagc ttaagcagca caccttcgca g                      41

<210> SEQ ID NO 87
<211> LENGTH: 41
<212> TYPE: DNA
<213> ORGANISM: Artificial Sequence
<220> FEATURE:
<223> OTHER INFORMATION: Synthetic primer

<400> SEQUENCE: 87
aacatcttcg ggttgtgagc ttaagccccg ctcgccggaa g                      41

<210> SEQ ID NO 88
<211> LENGTH: 47
<212> TYPE: DNA
<213> ORGANISM: Artificial Sequence
<220> FEATURE:
<223> OTHER INFORMATION: Synthetic primer

<400> SEQUENCE: 88
acagcttcgg cgttgtaagc ttaagccccg ctttatcgtt acttatg                47

<210> SEQ ID NO 89
<211> LENGTH: 38
<212> TYPE: DNA
<213> ORGANISM: Artificial Sequence
<220> FEATURE:
<223> OTHER INFORMATION: Synthetic primer

<400> SEQUENCE: 89
```
aacatcttcg ggttgtgagc ttaagccggg gcagggtg                                38

<210> SEQ ID NO 90
<211> LENGTH: 41
<212> TYPE: DNA
<213> ORGANISM: Artificial Sequence
<220> FEATURE:
<223> OTHER INFORMATION: Synthetic primer

<400> SEQUENCE: 90
acagcttcgg cgttgtaagc ttaagccgtt ggacaggaac c                            41

<210> SEQ ID NO 91
<211> LENGTH: 40
<212> TYPE: DNA
<213> ORGANISM: Artificial Sequence
<220> FEATURE:
<223> OTHER INFORMATION: Synthetic primer

<400> SEQUENCE: 91
aacatcttcg ggttgtgagc ttaagcggcg tagtcgatgg                              40

<210> SEQ ID NO 92
<211> LENGTH: 40
<212> TYPE: DNA
<213> ORGANISM: Artificial Sequence
<220> FEATURE:
<223> OTHER INFORMATION: Synthetic primer

<400> SEQUENCE: 92
acagcttcgg cgttgtaagc ttaagcggcc tcgccttagg                              40

<210> SEQ ID NO 93
<211> LENGTH: 43
<212> TYPE: DNA
<213> ORGANISM: Artificial Sequence
<220> FEATURE:
<223> OTHER INFORMATION: Synthetic primer

<400> SEQUENCE: 93
aacatcttcg ggttgtgagc ttaagccctg tacttggtgt tac                          43

<210> SEQ ID NO 94
<211> LENGTH: 42
<212> TYPE: DNA
<213> ORGANISM: Artificial Sequence
<220> FEATURE:
<223> OTHER INFORMATION: Synthetic primer

<400> SEQUENCE: 94
acagcttcgg cgttgtaagc ttaagccctg tttcccatcg ac                           42

<210> SEQ ID NO 95
<211> LENGTH: 39
<212> TYPE: DNA
<213> ORGANISM: Artificial Sequence
<220> FEATURE:
<223> OTHER INFORMATION: Synthetic primer

<400> SEQUENCE: 95
aacatcttcg ggttgtgagc ttaagcaggg gggacggag                               39

<210> SEQ ID NO 96
<211> LENGTH: 45
<212> TYPE: DNA

```
<213> ORGANISM: Artificial Sequence
<220> FEATURE:
<223> OTHER INFORMATION: Synthetic primer

<400> SEQUENCE: 96
acagcttcgg cgttgtaagc ttaagcgcag taacaccaag tacag         45

<210> SEQ ID NO 97
<211> LENGTH: 41
<212> TYPE: DNA
<213> ORGANISM: Artificial Sequence
<220> FEATURE:
<223> OTHER INFORMATION: Synthetic primer

<400> SEQUENCE: 97
aacatcttcg ggttgtgagc ttaagccccg gtttaagcgt g             41

<210> SEQ ID NO 98
<211> LENGTH: 40
<212> TYPE: DNA
<213> ORGANISM: Artificial Sequence
<220> FEATURE:
<223> OTHER INFORMATION: Synthetic primer

<400> SEQUENCE: 98
acagcttcgg cgttgtaagc ttaagccccg gccaacatag               40

<210> SEQ ID NO 99
<211> LENGTH: 41
<212> TYPE: DNA
<213> ORGANISM: Artificial Sequence
<220> FEATURE:
<223> OTHER INFORMATION: Synthetic primer

<400> SEQUENCE: 99
aacatcttcg ggttgtgagc ttaagcggct ggttttccag g             41

<210> SEQ ID NO 100
<211> LENGTH: 42
<212> TYPE: DNA
<213> ORGANISM: Artificial Sequence
<220> FEATURE:
<223> OTHER INFORMATION: Synthetic primer

<400> SEQUENCE: 100
acagcttcgg cgttgtaagc ttaagcacgc ttaaaccggg ac            42

<210> SEQ ID NO 101
<211> LENGTH: 43
<212> TYPE: DNA
<213> ORGANISM: Artificial Sequence
<220> FEATURE:
<223> OTHER INFORMATION: Synthetic primer

<400> SEQUENCE: 101
aacatcttcg ggttgtgagc ttaagcccgg aaaatcaagg ctg           43

<210> SEQ ID NO 102
<211> LENGTH: 44
<212> TYPE: DNA
<213> ORGANISM: Artificial Sequence
<220> FEATURE:
<223> OTHER INFORMATION: Synthetic primer

<400> SEQUENCE: 102
acagcttcgg cgttgtaagc ttaagccctg gaaaaccagc ctac          44
```

<210> SEQ ID NO 103
<211> LENGTH: 40
<212> TYPE: DNA
<213> ORGANISM: Artificial Sequence
<220> FEATURE:
<223> OTHER INFORMATION: Synthetic primer

<400> SEQUENCE: 103
aacatcttcg ggttgtgagc ttaagcgctg aggcgtgatg                   40

<210> SEQ ID NO 104
<211> LENGTH: 43
<212> TYPE: DNA
<213> ORGANISM: Artificial Sequence
<220> FEATURE:
<223> OTHER INFORMATION: Synthetic primer

<400> SEQUENCE: 104
acagcttcgg cgttgtaagc ttaagctgat tttccggatt tgc               43

<210> SEQ ID NO 105
<211> LENGTH: 41
<212> TYPE: DNA
<213> ORGANISM: Artificial Sequence
<220> FEATURE:
<223> OTHER INFORMATION: Synthetic primer

<400> SEQUENCE: 105
aacatcttcg ggttgtgagc ttaagctgac gaggcactac g                 41

<210> SEQ ID NO 106
<211> LENGTH: 40
<212> TYPE: DNA
<213> ORGANISM: Artificial Sequence
<220> FEATURE:
<223> OTHER INFORMATION: Synthetic primer

<400> SEQUENCE: 106
acagcttcgg cgttgtaagc ttaagcacgc ctcagccttg                   40

<210> SEQ ID NO 107
<211> LENGTH: 44
<212> TYPE: DNA
<213> ORGANISM: Artificial Sequence
<220> FEATURE:
<223> OTHER INFORMATION: Synthetic primer

<400> SEQUENCE: 107
aacatcttcg ggttgtgagc ttaagcgtgc tgaagcaaca aatg              44

<210> SEQ ID NO 108
<211> LENGTH: 42
<212> TYPE: DNA
<213> ORGANISM: Artificial Sequence
<220> FEATURE:
<223> OTHER INFORMATION: Synthetic primer

<400> SEQUENCE: 108
acagcttcgg cgttgtaagc ttaagcgtgc ctcgtcatca cg                42

<210> SEQ ID NO 109
<211> LENGTH: 41
<212> TYPE: DNA
<213> ORGANISM: Artificial Sequence
<220> FEATURE:

<223> OTHER INFORMATION: Synthetic primer

<400> SEQUENCE: 109
aacatcttcg ggttgtgagc ttaagccaac aaatgccctg c          41

<210> SEQ ID NO 110
<211> LENGTH: 40
<212> TYPE: DNA
<213> ORGANISM: Artificial Sequence
<220> FEATURE:
<223> OTHER INFORMATION: Synthetic primer

<400> SEQUENCE: 110
acagcttcgg cgttgtaagc ttaagccagc accgtagtgc            40

<210> SEQ ID NO 111
<211> LENGTH: 44
<212> TYPE: DNA
<213> ORGANISM: Artificial Sequence
<220> FEATURE:
<223> OTHER INFORMATION: Synthetic primer

<400> SEQUENCE: 111
aacatcttcg ggttgtgagc ttaagcggta acatcaaatc gtac       44

<210> SEQ ID NO 112
<211> LENGTH: 42
<212> TYPE: DNA
<213> ORGANISM: Artificial Sequence
<220> FEATURE:
<223> OTHER INFORMATION: Synthetic primer

<400> SEQUENCE: 112
acagcttcgg cgttgtaagc ttaagcgctt agaggctttt cc         42

<210> SEQ ID NO 113
<211> LENGTH: 41
<212> TYPE: DNA
<213> ORGANISM: Artificial Sequence
<220> FEATURE:
<223> OTHER INFORMATION: Synthetic primer

<400> SEQUENCE: 113
aacatcttcg ggttgtgagc ttaagcggtg gtcaggtaga g          41

<210> SEQ ID NO 114
<211> LENGTH: 44
<212> TYPE: DNA
<213> ORGANISM: Artificial Sequence
<220> FEATURE:
<223> OTHER INFORMATION: Synthetic primer

<400> SEQUENCE: 114
acagcttcgg cgttgtaagc ttaagcggtt tggggtacga tttg       44

<210> SEQ ID NO 115
<211> LENGTH: 40
<212> TYPE: DNA
<213> ORGANISM: Artificial Sequence
<220> FEATURE:
<223> OTHER INFORMATION: Synthetic primer

<400> SEQUENCE: 115
aacatcttcg ggttgtgagc ttaagctacc aaggcgcttg            40

<210> SEQ ID NO 116
<211> LENGTH: 42
<212> TYPE: DNA
<213> ORGANISM: Artificial Sequence
<220> FEATURE:
<223> OTHER INFORMATION: Synthetic primer

<400> SEQUENCE: 116
acagcttcgg cgttgtaagc ttaagctacc tgaccacctg tg        42

<210> SEQ ID NO 117
<211> LENGTH: 41
<212> TYPE: DNA
<213> ORGANISM: Artificial Sequence
<220> FEATURE:
<223> OTHER INFORMATION: Synthetic primer

<400> SEQUENCE: 117
aacatcttcg ggttgtgagc ttaagcggag aaggcacgct g        41

<210> SEQ ID NO 118
<211> LENGTH: 43
<212> TYPE: DNA
<213> ORGANISM: Artificial Sequence
<220> FEATURE:
<223> OTHER INFORMATION: Synthetic primer

<400> SEQUENCE: 118
acagcttcgg cgttgtaagc ttaagcgtta cggcaccatt ttg        43

<210> SEQ ID NO 119
<211> LENGTH: 41
<212> TYPE: DNA
<213> ORGANISM: Artificial Sequence
<220> FEATURE:
<223> OTHER INFORMATION: Synthetic primer

<400> SEQUENCE: 119
aacatcttcg ggttgtgagc ttaagctagg tgaggtccct c        41

<210> SEQ ID NO 120
<211> LENGTH: 40
<212> TYPE: DNA
<213> ORGANISM: Artificial Sequence
<220> FEATURE:
<223> OTHER INFORMATION: Synthetic primer

<400> SEQUENCE: 120
acagcttcgg cgttgtaagc ttaagcatca gcgtgccttc        40

<210> SEQ ID NO 121
<211> LENGTH: 42
<212> TYPE: DNA
<213> ORGANISM: Artificial Sequence
<220> FEATURE:
<223> OTHER INFORMATION: Synthetic primer

<400> SEQUENCE: 121
aacatcttcg ggttgtgagc ttaagcggat ggagctgaaa tc        42

<210> SEQ ID NO 122
<211> LENGTH: 44
<212> TYPE: DNA
<213> ORGANISM: Artificial Sequence
<220> FEATURE:
<223> OTHER INFORMATION: Synthetic primer

```
<400> SEQUENCE: 122
acagcttcgg cgttgtaagc ttaagcggac ctcacctaca tatc           44

<210> SEQ ID NO 123
<211> LENGTH: 46
<212> TYPE: DNA
<213> ORGANISM: Artificial Sequence
<220> FEATURE:
<223> OTHER INFORMATION: Synthetic primer

<400> SEQUENCE: 123
aacatcttcg ggttgtgagc ttaagcctga aatcagtcga agatac         46

<210> SEQ ID NO 124
<211> LENGTH: 42
<212> TYPE: DNA
<213> ORGANISM: Artificial Sequence
<220> FEATURE:
<223> OTHER INFORMATION: Synthetic primer

<400> SEQUENCE: 124
acagcttcgg cgttgtaagc ttaagcatcc gcgagggacc tc             42

<210> SEQ ID NO 125
<211> LENGTH: 41
<212> TYPE: DNA
<213> ORGANISM: Artificial Sequence
<220> FEATURE:
<223> OTHER INFORMATION: Synthetic primer

<400> SEQUENCE: 125
aacatcttcg ggttgtgagc ttaagcgata ccagctggct g              41

<210> SEQ ID NO 126
<211> LENGTH: 42
<212> TYPE: DNA
<213> ORGANISM: Artificial Sequence
<220> FEATURE:
<223> OTHER INFORMATION: Synthetic primer

<400> SEQUENCE: 126
acagcttcgg cgttgtaagc ttaagcgact gatttcagct cc             42

<210> SEQ ID NO 127
<211> LENGTH: 40
<212> TYPE: DNA
<213> ORGANISM: Artificial Sequence
<220> FEATURE:
<223> OTHER INFORMATION: Synthetic primer

<400> SEQUENCE: 127
aacatcttcg ggttgtgagc ttaagcacac agcactgtgc                40

<210> SEQ ID NO 128
<211> LENGTH: 40
<212> TYPE: DNA
<213> ORGANISM: Artificial Sequence
<220> FEATURE:
<223> OTHER INFORMATION: Synthetic primer

<400> SEQUENCE: 128
acagcttcgg cgttgtaagc ttaagcacag ttgcagccag                40

<210> SEQ ID NO 129
<211> LENGTH: 42
```

<212> TYPE: DNA
<213> ORGANISM: Artificial Sequence
<220> FEATURE:
<223> OTHER INFORMATION: Synthetic primer

<400> SEQUENCE: 129
aacatcttcg ggttgtgagc ttaagcgtgg acgtatacgg tg                42

<210> SEQ ID NO 130
<211> LENGTH: 41
<212> TYPE: DNA
<213> ORGANISM: Artificial Sequence
<220> FEATURE:
<223> OTHER INFORMATION: Synthetic primer

<400> SEQUENCE: 130
acagcttcgg cgttgtaagc ttaagcgtgt ttgcacagtg c                 41

<210> SEQ ID NO 131
<211> LENGTH: 44
<212> TYPE: DNA
<213> ORGANISM: Artificial Sequence
<220> FEATURE:
<223> OTHER INFORMATION: Synthetic primer

<400> SEQUENCE: 131
aacatcttcg ggttgtgagc ttaagcgtgc cggaaggtta attg              44

<210> SEQ ID NO 132
<211> LENGTH: 40
<212> TYPE: DNA
<213> ORGANISM: Artificial Sequence
<220> FEATURE:
<223> OTHER INFORMATION: Synthetic primer

<400> SEQUENCE: 132
acagcttcgg cgttgtaagc ttaagcggca ggcgtcacac                   40

<210> SEQ ID NO 133
<211> LENGTH: 45
<212> TYPE: DNA
<213> ORGANISM: Artificial Sequence
<220> FEATURE:
<223> OTHER INFORMATION: Synthetic primer

<400> SEQUENCE: 133
aacatcttcg ggttgtgagc ttaagcggtt aattgatggg gttag             45

<210> SEQ ID NO 134
<211> LENGTH: 40
<212> TYPE: DNA
<213> ORGANISM: Artificial Sequence
<220> FEATURE:
<223> OTHER INFORMATION: Synthetic primer

<400> SEQUENCE: 134
acagcttcgg cgttgtaagc ttaagcccgg caccgggcag                   40

<210> SEQ ID NO 135
<211> LENGTH: 41
<212> TYPE: DNA
<213> ORGANISM: Artificial Sequence
<220> FEATURE:
<223> OTHER INFORMATION: Synthetic primer

<400> SEQUENCE: 135
aacatcttcg ggttgtgagc ttaagcgcga agctcttgat c                          41

<210> SEQ ID NO 136
<211> LENGTH: 45
<212> TYPE: DNA
<213> ORGANISM: Artificial Sequence
<220> FEATURE:
<223> OTHER INFORMATION: Synthetic primer

<400> SEQUENCE: 136
acagcttcgg cgttgtaagc ttaagcgcta accccatcaa ttaac                      45

<210> SEQ ID NO 137
<211> LENGTH: 42
<212> TYPE: DNA
<213> ORGANISM: Artificial Sequence
<220> FEATURE:
<223> OTHER INFORMATION: Synthetic primer

<400> SEQUENCE: 137
aacatcttcg ggttgtgagc ttaagcacgg tcctaaggta gc                         42

<210> SEQ ID NO 138
<211> LENGTH: 41
<212> TYPE: DNA
<213> ORGANISM: Artificial Sequence
<220> FEATURE:
<223> OTHER INFORMATION: Synthetic primer

<400> SEQUENCE: 138
acagcttcgg cgttgtaagc ttaagcacgg ccgccgttta c                          41

<210> SEQ ID NO 139
<211> LENGTH: 44
<212> TYPE: DNA
<213> ORGANISM: Artificial Sequence
<220> FEATURE:
<223> OTHER INFORMATION: Synthetic primer

<400> SEQUENCE: 139
aacatcttcg ggttgtgagc ttaagctagc gaaattcctt gtcg                       44

<210> SEQ ID NO 140
<211> LENGTH: 44
<212> TYPE: DNA
<213> ORGANISM: Artificial Sequence
<220> FEATURE:
<223> OTHER INFORMATION: Synthetic primer

<400> SEQUENCE: 140
acagcttcgg cgttgtaagc ttaagcagga ccgttatagt tacg                       44

<210> SEQ ID NO 141
<211> LENGTH: 39
<212> TYPE: DNA
<213> ORGANISM: Artificial Sequence
<220> FEATURE:
<223> OTHER INFORMATION: Synthetic primer

<400> SEQUENCE: 141
aacatcttcg ggttgtgagc ttaagctccg acctgcacg                             39

<210> SEQ ID NO 142
<211> LENGTH: 42
<212> TYPE: DNA
<213> ORGANISM: Artificial Sequence
<220> FEATURE:
<223> OTHER INFORMATION: Synthetic primer

<400> SEQUENCE: 142
acagcttcgg cgttgtaagc ttaagccccg acaaggaatt tc            42

<210> SEQ ID NO 143
<211> LENGTH: 40
<212> TYPE: DNA
<213> ORGANISM: Artificial Sequence
<220> FEATURE:
<223> OTHER INFORMATION: Synthetic primer

<400> SEQUENCE: 143
aacatcttcg ggttgtgagc ttaagctgtc tccacccgag              40

<210> SEQ ID NO 144
<211> LENGTH: 41
<212> TYPE: DNA
<213> ORGANISM: Artificial Sequence
<220> FEATURE:
<223> OTHER INFORMATION: Synthetic primer

<400> SEQUENCE: 144
acagcttcgg cgttgtaagc ttaagcctgg ccatcattac g            41

<210> SEQ ID NO 145
<211> LENGTH: 44
<212> TYPE: DNA
<213> ORGANISM: Artificial Sequence
<220> FEATURE:
<223> OTHER INFORMATION: Synthetic primer

<400> SEQUENCE: 145
aacatcttcg ggttgtgagc ttaagccagt gtacccgcgg caag         44

<210> SEQ ID NO 146
<211> LENGTH: 46
<212> TYPE: DNA
<213> ORGANISM: Artificial Sequence
<220> FEATURE:
<223> OTHER INFORMATION: Synthetic primer

<400> SEQUENCE: 146
acagcttcgg cgttgtaagc ttaagccagc gagttcaatt tcactg       46

<210> SEQ ID NO 147
<211> LENGTH: 40
<212> TYPE: DNA
<213> ORGANISM: Artificial Sequence
<220> FEATURE:
<223> OTHER INFORMATION: Synthetic primer

<400> SEQUENCE: 147
aacatcttcg ggttgtgagc ttaagcagtc tgcatggagc              40

<210> SEQ ID NO 148
<211> LENGTH: 42
<212> TYPE: DNA
<213> ORGANISM: Artificial Sequence
<220> FEATURE:
<223> OTHER INFORMATION: Synthetic primer

<400> SEQUENCE: 148
acagcttcgg cgttgtaagc ttaagccgtc cacacttcaa ag           42

<210> SEQ ID NO 149
<211> LENGTH: 43
<212> TYPE: DNA
<213> ORGANISM: Artificial Sequence
<220> FEATURE:
<223> OTHER INFORMATION: Synthetic primer

<400> SEQUENCE: 149
aacatcttcg ggttgtgagc ttaagcgtct gcatggagcc gac                43

<210> SEQ ID NO 150
<211> LENGTH: 45
<212> TYPE: DNA
<213> ORGANISM: Artificial Sequence
<220> FEATURE:
<223> OTHER INFORMATION: Synthetic primer

<400> SEQUENCE: 150
acagcttcgg cgttgtaagc ttaagcgtcc acacttcaaa gcctc              45

<210> SEQ ID NO 151
<211> LENGTH: 40
<212> TYPE: DNA
<213> ORGANISM: Artificial Sequence
<220> FEATURE:
<223> OTHER INFORMATION: Synthetic primer

<400> SEQUENCE: 151
aacatcttcg ggttgtgagc ttaagccggg ttgcggacag                    40

<210> SEQ ID NO 152
<211> LENGTH: 43
<212> TYPE: DNA
<213> ORGANISM: Artificial Sequence
<220> FEATURE:
<223> OTHER INFORMATION: Synthetic primer

<400> SEQUENCE: 152
acagcttcgg cgttgtaagc ttaagccggg tcaacgttag aac                43

<210> SEQ ID NO 153
<211> LENGTH: 44
<212> TYPE: DNA
<213> ORGANISM: Artificial Sequence
<220> FEATURE:
<223> OTHER INFORMATION: Synthetic primer

<400> SEQUENCE: 153
aacatcttcg ggttgtgagc ttaagccggt ctcctcctaa agag               44

<210> SEQ ID NO 154
<211> LENGTH: 43
<212> TYPE: DNA
<213> ORGANISM: Artificial Sequence
<220> FEATURE:
<223> OTHER INFORMATION: Synthetic primer

<400> SEQUENCE: 154
acagcttcgg cgttgtaagc ttaagccagt caaactaccc acc                43

<210> SEQ ID NO 155
<211> LENGTH: 41
<212> TYPE: DNA
<213> ORGANISM: Artificial Sequence
<220> FEATURE:
<223> OTHER INFORMATION: Synthetic primer

<400> SEQUENCE: 155
aacatcttcg ggttgtgagc ttaagcggag gagcacgaag g        41

<210> SEQ ID NO 156
<211> LENGTH: 43
<212> TYPE: DNA
<213> ORGANISM: Artificial Sequence
<220> FEATURE:
<223> OTHER INFORMATION: Synthetic primer

<400> SEQUENCE: 156
acagcttcgg cgttgtaagc ttaagcggag gagaccgccc cag        43

<210> SEQ ID NO 157
<211> LENGTH: 41
<212> TYPE: DNA
<213> ORGANISM: Artificial Sequence
<220> FEATURE:
<223> OTHER INFORMATION: Synthetic primer

<400> SEQUENCE: 157
aacatcttcg ggttgtgagc ttaagctcag gaggttagtg c        41

<210> SEQ ID NO 158
<211> LENGTH: 42
<212> TYPE: DNA
<213> ORGANISM: Artificial Sequence
<220> FEATURE:
<223> OTHER INFORMATION: Synthetic primer

<400> SEQUENCE: 158
acagcttcgg cgttgtaagc ttaagcccag gattagccaa cc        42

<210> SEQ ID NO 159
<211> LENGTH: 43
<212> TYPE: DNA
<213> ORGANISM: Artificial Sequence
<220> FEATURE:
<223> OTHER INFORMATION: Synthetic primer

<400> SEQUENCE: 159
aacatcttcg ggttgtgagc ttaagcgcat aagccagctt gac        43

<210> SEQ ID NO 160
<211> LENGTH: 44
<212> TYPE: DNA
<213> ORGANISM: Artificial Sequence
<220> FEATURE:
<223> OTHER INFORMATION: Synthetic primer

<400> SEQUENCE: 160
acagcttcgg cgttgtaagc ttaagcacta acctcctgat gtcc        44

<210> SEQ ID NO 161
<211> LENGTH: 39
<212> TYPE: DNA
<213> ORGANISM: Artificial Sequence
<220> FEATURE:
<223> OTHER INFORMATION: Synthetic primer

<400> SEQUENCE: 161
aacatcttcg ggttgtgagc ttaagccgcg agcaggtgc        39

<210> SEQ ID NO 162

```
<211> LENGTH: 40
<212> TYPE: DNA
<213> ORGANISM: Artificial Sequence
<220> FEATURE:
<223> OTHER INFORMATION: Synthetic primer

<400> SEQUENCE: 162
acagcttcgg cgttgtaagc ttaagccgct cgcagtcaag                       40

<210> SEQ ID NO 163
<211> LENGTH: 43
<212> TYPE: DNA
<213> ORGANISM: Artificial Sequence
<220> FEATURE:
<223> OTHER INFORMATION: Synthetic primer

<400> SEQUENCE: 163
aacatcttcg ggttgtgagc ttaagcgcag gtcatagtga tcc                   43

<210> SEQ ID NO 164
<211> LENGTH: 44
<212> TYPE: DNA
<213> ORGANISM: Artificial Sequence
<220> FEATURE:
<223> OTHER INFORMATION: Synthetic primer

<400> SEQUENCE: 164
acagcttcgg cgttgtaagc ttaagcgcac ctgctcgcgc cgtc                  44

<210> SEQ ID NO 165
<211> LENGTH: 41
<212> TYPE: DNA
<213> ORGANISM: Artificial Sequence
<220> FEATURE:
<223> OTHER INFORMATION: Synthetic primer

<400> SEQUENCE: 165
aacatcttcg ggttgtgagc ttaagcgggc catcgctcaa c                     41

<210> SEQ ID NO 166
<211> LENGTH: 40
<212> TYPE: DNA
<213> ORGANISM: Artificial Sequence
<220> FEATURE:
<223> OTHER INFORMATION: Synthetic primer

<400> SEQUENCE: 166
acagcttcgg cgttgtaagc ttaagcagaa ccaccggatc                       40

<210> SEQ ID NO 167
<211> LENGTH: 42
<212> TYPE: DNA
<213> ORGANISM: Artificial Sequence
<220> FEATURE:
<223> OTHER INFORMATION: Synthetic primer

<400> SEQUENCE: 167
aacatcttcg ggttgtgagc ttaagctcga cggcggtgtt tg                    42

<210> SEQ ID NO 168
<211> LENGTH: 42
<212> TYPE: DNA
<213> ORGANISM: Artificial Sequence
<220> FEATURE:
<223> OTHER INFORMATION: Synthetic primer

<400> SEQUENCE: 168
```
acagcttcgg cgttgtaagc ttaagctctt gggcggtatc ag					42

<210> SEQ ID NO 169
<211> LENGTH: 42
<212> TYPE: DNA
<213> ORGANISM: Artificial Sequence
<220> FEATURE:
<223> OTHER INFORMATION: Synthetic primer

<400> SEQUENCE: 169
aacatcttcg ggttgtgagc ttaagcaggt cccaagggta tg					42

<210> SEQ ID NO 170
<211> LENGTH: 41
<212> TYPE: DNA
<213> ORGANISM: Artificial Sequence
<220> FEATURE:
<223> OTHER INFORMATION: Synthetic primer

<400> SEQUENCE: 170
acagcttcgg cgttgtaagc ttaagccagc cccaggatgt g					41

<210> SEQ ID NO 171
<211> LENGTH: 44
<212> TYPE: DNA
<213> ORGANISM: Artificial Sequence
<220> FEATURE:
<223> OTHER INFORMATION: Synthetic primer

<400> SEQUENCE: 171
aacatcttcg ggttgtgagc ttaagcgcca tttaaagtgg tacg					44

<210> SEQ ID NO 172
<211> LENGTH: 42
<212> TYPE: DNA
<213> ORGANISM: Artificial Sequence
<220> FEATURE:
<223> OTHER INFORMATION: Synthetic primer

<400> SEQUENCE: 172
acagcttcgg cgttgtaagc ttaagcgcca taccettggg ac					42

<210> SEQ ID NO 173
<211> LENGTH: 41
<212> TYPE: DNA
<213> ORGANISM: Artificial Sequence
<220> FEATURE:
<223> OTHER INFORMATION: Synthetic primer

<400> SEQUENCE: 173
aacatcttcg ggttgtgagc ttaagcgtgg tacgcgagct g					41

<210> SEQ ID NO 174
<211> LENGTH: 43
<212> TYPE: DNA
<213> ORGANISM: Artificial Sequence
<220> FEATURE:
<223> OTHER INFORMATION: Synthetic primer

<400> SEQUENCE: 174
acagcttcgg cgttgtaagc ttaagcatgg cgaacagcca tac					43

<210> SEQ ID NO 175
<211> LENGTH: 44
<212> TYPE: DNA

```
<213> ORGANISM: Artificial Sequence
<220> FEATURE:
<223> OTHER INFORMATION: Synthetic primer

<400> SEQUENCE: 175
aacatcttcg ggttgtgagc ttaagcgaca gttcggtccc tatc          44

<210> SEQ ID NO 176
<211> LENGTH: 43
<212> TYPE: DNA
<213> ORGANISM: Artificial Sequence
<220> FEATURE:
<223> OTHER INFORMATION: Synthetic primer

<400> SEQUENCE: 176
acagcttcgg cgttgtaagc ttaagcgacg ttctaaaccc agc           43

<210> SEQ ID NO 177
<211> LENGTH: 40
<212> TYPE: DNA
<213> ORGANISM: Artificial Sequence
<220> FEATURE:
<223> OTHER INFORMATION: Synthetic primer

<400> SEQUENCE: 177
aacatcttcg ggttgtgagc ttaagcggac cggagtggac               40

<210> SEQ ID NO 178
<211> LENGTH: 40
<212> TYPE: DNA
<213> ORGANISM: Artificial Sequence
<220> FEATURE:
<223> OTHER INFORMATION: Synthetic primer

<400> SEQUENCE: 178
acagcttcgg cgttgtaagc ttaagcgtac taggagcagc               40

<210> SEQ ID NO 179
<211> LENGTH: 43
<212> TYPE: DNA
<213> ORGANISM: Artificial Sequence
<220> FEATURE:
<223> OTHER INFORMATION: Synthetic primer

<400> SEQUENCE: 179
aacatcttcg ggttgtgagc ttaagcatgg cactgcccgg tag           43

<210> SEQ ID NO 180
<211> LENGTH: 43
<212> TYPE: DNA
<213> ORGANISM: Artificial Sequence
<220> FEATURE:
<223> OTHER INFORMATION: Synthetic primer

<400> SEQUENCE: 180
acagcttcgg cgttgtaagc ttaagcatga caacccgaac acc           43

<210> SEQ ID NO 181
<211> LENGTH: 44
<212> TYPE: DNA
<213> ORGANISM: Artificial Sequence
<220> FEATURE:
<223> OTHER INFORMATION: Synthetic primer

<400> SEQUENCE: 181
aacatcttcg ggttgtgagc ttaagcgtgc tgaaagcatc taag          44
```

<210> SEQ ID NO 182
<211> LENGTH: 45
<212> TYPE: DNA
<213> ORGANISM: Artificial Sequence
<220> FEATURE:
<223> OTHER INFORMATION: Synthetic primer

<400> SEQUENCE: 182
acagcttcgg cgttgtaagc ttaagcctct tccgcattta gctac         45

<210> SEQ ID NO 183
<211> LENGTH: 40
<212> TYPE: DNA
<213> ORGANISM: Artificial Sequence
<220> FEATURE:
<223> OTHER INFORMATION: Synthetic primer

<400> SEQUENCE: 183
aacatcttcg ggttgtgagc ttaagcagca cgaaacttgc               40

<210> SEQ ID NO 184
<211> LENGTH: 42
<212> TYPE: DNA
<213> ORGANISM: Artificial Sequence
<220> FEATURE:
<223> OTHER INFORMATION: Synthetic primer

<400> SEQUENCE: 184
acagcttcgg cgttgtaagc ttaagcagca cttatctctt cc            42

<210> SEQ ID NO 185
<211> LENGTH: 42
<212> TYPE: DNA
<213> ORGANISM: Artificial Sequence
<220> FEATURE:
<223> OTHER INFORMATION: Synthetic primer

<400> SEQUENCE: 185
aacatcttcg ggttgtgagc ttaagcaggg tcctgaagga ac            42

<210> SEQ ID NO 186
<211> LENGTH: 41
<212> TYPE: DNA
<213> ORGANISM: Artificial Sequence
<220> FEATURE:
<223> OTHER INFORMATION: Synthetic primer

<400> SEQUENCE: 186
acagcttcgg cgttgtaagc ttaagcaggg tcagggagaa c             41

<210> SEQ ID NO 187
<211> LENGTH: 39
<212> TYPE: DNA
<213> ORGANISM: Artificial Sequence
<220> FEATURE:
<223> OTHER INFORMATION: Synthetic primer

<400> SEQUENCE: 187
aacatcttcg ggttgtgagc ttaagccgac gttgatagg                39

<210> SEQ ID NO 188
<211> LENGTH: 41
<212> TYPE: DNA
<213> ORGANISM: Artificial Sequence
<220> FEATURE:

<223> OTHER INFORMATION: Synthetic primer

<400> SEQUENCE: 188
acagcttcgg cgttgtaagc ttaagccaac gttccttcag g                41

<210> SEQ ID NO 189
<211> LENGTH: 40
<212> TYPE: DNA
<213> ORGANISM: Artificial Sequence
<220> FEATURE:
<223> OTHER INFORMATION: Synthetic primer

<400> SEQUENCE: 189
aacatcttcg ggttgtgagc ttaagctgcg ttgagctaac                 40

<210> SEQ ID NO 190
<211> LENGTH: 39
<212> TYPE: DNA
<213> ORGANISM: Artificial Sequence
<220> FEATURE:
<223> OTHER INFORMATION: Synthetic primer

<400> SEQUENCE: 190
acagcttcgg cgttgtaagc ttaagctgcg cttacacac                  39

<210> SEQ ID NO 191
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: g to c mutation
<220> FEATURE:
<221> NAME/KEY: misc_feature
<222> LOCATION: (1)..(1)
<223> OTHER INFORMATION: phosphorylated nucleotide

<400> SEQUENCE: 191
cttaagcgac taagcgtaca c                                     21

<210> SEQ ID NO 192
<211> LENGTH: 21
<212> TYPE: DNA
<213> ORGANISM: Artificial Sequence
<220> FEATURE:
<223> OTHER INFORMATION: synthetic primer

<400> SEQUENCE: 192
ctcacaaccc gaagatgttt c                                     21

<210> SEQ ID NO 193
<211> LENGTH: 19
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: c to g mutation
<220> FEATURE:
<221> NAME/KEY: misc_feature
<222> LOCATION: (1)..(1)
<223> OTHER INFORMATION: phosphorylated nucleotide

<400> SEQUENCE: 193

```
gcttacaacg ccgaagctg                                              19
```

<210> SEQ ID NO 194
<211> LENGTH: 21
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: Phosphorylated nucleotide

<400> SEQUENCE: 194

```
ttaagcctca cggttcatta g                                           21
```

<210> SEQ ID NO 195
<211> LENGTH: 20
<212> TYPE: DNA
<213> ORGANISM: Artificial Sequence
<220> FEATURE:
<223> OTHER INFORMATION: Synthetic primer

<400> SEQUENCE: 195

```
gcagattagc acgtccttca                                             20
```

<210> SEQ ID NO 196
<211> LENGTH: 20
<212> TYPE: DNA
<213> ORGANISM: Artificial Sequence
<220> FEATURE:
<223> OTHER INFORMATION: Synthetic primer

<400> SEQUENCE: 196

```
cgttgagcta accggtacta                                             20
```

<210> SEQ ID NO 197
<211> LENGTH: 23
<212> TYPE: DNA
<213> ORGANISM: Artificial Sequence
<220> FEATURE:
<223> OTHER INFORMATION: Synthetic primer

<400> SEQUENCE: 197

```
gggtgatgtt tgagatattt gct                                         23
```

<210> SEQ ID NO 198
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (5)..(9)
<223> OTHER INFORMATION: BamHI restriction site

<400> SEQUENCE: 198

```
tattggatcc gatgcgttga gctaaccggt a                                31
```

<210> SEQ ID NO 199
<211> LENGTH: 32
<212> TYPE: DNA
<213> ORGANISM: Artificial Sequence
<220> FEATURE:
<223> OTHER INFORMATION: Synthetic primer
<220> FEATURE:

```
<221> NAME/KEY: misc_feature
<222> LOCATION: (5)..(9)
<223> OTHER INFORMATION: BamHI restriction site

<400> SEQUENCE: 199
ttatggatcc tgcgcttaca cacccggcct at                              32

<210> SEQ ID NO 200
<211> LENGTH: 66
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (27)..(38)
<223> OTHER INFORMATION: polyadenine linker of optional length
<220> FEATURE:
<221> NAME/KEY: misc_feature
<222> LOCATION: (34)..(38)
<223> OTHER INFORMATION: "n" is an optional a

<400> SEQUENCE: 200
ttagtaccgg ttagctcaac gcatcgtttt tttnnnnncg aaggttaagc tacctacttc    60
ttttgc                                                              66

<210> SEQ ID NO 201
<211> LENGTH: 59
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (27)..(38)
<223> OTHER INFORMATION: polyadenine linker of optional length
<220> FEATURE:
<221> NAME/KEY: misc_feature
<222> LOCATION: (34)..(38)
<223> OTHER INFORMATION: "n" is an optional a

<400> SEQUENCE: 201
ttgataggcc gggtgtgtaa gcgcagaaaa aaannnnngg agggcgctta ccactttgt     59

<210> SEQ ID NO 202
<211> LENGTH: 23
<212> TYPE: DNA
<213> ORGANISM: Artificial Sequence
<220> FEATURE:
<223> OTHER INFORMATION: Synthetic primer

<400> SEQUENCE: 202
gaaccttacc tggtcttgac atc                                           23

<210> SEQ ID NO 203
<211> LENGTH: 19
<212> TYPE: DNA
<213> ORGANISM: Artificial Sequence
<220> FEATURE:
<223> OTHER INFORMATION: Synthetic primer

<400> SEQUENCE: 203
atatcgacgg cggtgtttg                                                19

<210> SEQ ID NO 204
<211> LENGTH: 20
<212> TYPE: DNA
<213> ORGANISM: Artificial Sequence
```

```
<220> FEATURE:
<223> OTHER INFORMATION: Synthetic primer

<400> SEQUENCE: 204
gacagttcgg tccctatctg                                                   20

<210> SEQ ID NO 205
<211> LENGTH: 21
<212> TYPE: DNA
<213> ORGANISM: Artificial Sequence
<220> FEATURE:
<223> OTHER INFORMATION: Synthetic primer

<400> SEQUENCE: 205
ttaagcctca cggttcatta g                                                 21

<210> SEQ ID NO 206
<211> LENGTH: 20
<212> TYPE: DNA
<213> ORGANISM: Artificial Sequence
<220> FEATURE:
<223> OTHER INFORMATION: Synthetic primer

<400> SEQUENCE: 206
gactgccagg gcatccaccg                                                   20

<210> SEQ ID NO 207
<211> LENGTH: 17
<212> TYPE: DNA
<213> ORGANISM: Artificial Sequence
<220> FEATURE:
<223> OTHER INFORMATION: Synthetic primer

<400> SEQUENCE: 207
aaggttaagc ctcacgg                                                      17

<210> SEQ ID NO 208
<211> LENGTH: 21
<212> TYPE: DNA
<213> ORGANISM: Artificial Sequence
<220> FEATURE:
<223> OTHER INFORMATION: Synthetic primer

<400> SEQUENCE: 208
ccctacggtt accttgttac g                                                 21

<210> SEQ ID NO 209
<211> LENGTH: 22
<212> TYPE: DNA
<213> ORGANISM: Artificial Sequence
<220> FEATURE:
<223> OTHER INFORMATION: Synthetic primer

<400> SEQUENCE: 209
gtaccggtta gctcaacgca tc                                                22

<210> SEQ ID NO 210
<211> LENGTH: 23
<212> TYPE: DNA
<213> ORGANISM: Artificial Sequence
<220> FEATURE:
<223> OTHER INFORMATION: Synthetic primer

<400> SEQUENCE: 210
cacaaagtgg taagcgccct cct                                               23
```

```
<210> SEQ ID NO 211
<211> LENGTH: 20
<212> TYPE: DNA
<213> ORGANISM: Artificial Sequence
<220> FEATURE:
<223> OTHER INFORMATION: Synthetic primer

<400> SEQUENCE: 211
taatacgact cactataggg                                               20

<210> SEQ ID NO 212
<211> LENGTH: 19
<212> TYPE: DNA
<213> ORGANISM: Artificial Sequence
<220> FEATURE:
<223> OTHER INFORMATION: Synthetic primer

<400> SEQUENCE: 212
cttcctttcg ggctttgtt                                                19

<210> SEQ ID NO 213
<211> LENGTH: 23
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: Phosporylated nucleotide

<400> SEQUENCE: 213
taactgtcag accaagttta ctc                                           23

<210> SEQ ID NO 214
<211> LENGTH: 27
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: Phosporylated nucleotide

<400> SEQUENCE: 214
actcttcctt tttcaatatt attgaag                                       27

<210> SEQ ID NO 215
<211> LENGTH: 48
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: Phosporylated nucleotide
<220> FEATURE:
<221> NAME/KEY: misc_feature
<222> LOCATION: (1)..(6)
<223> OTHER INFORMATION: BglII site
<220> FEATURE:
<221> NAME/KEY: misc_feature
<222> LOCATION: (23)..(30)
<223> OTHER INFORMATION: NotI site

<400> SEQUENCE: 215
agatctgttg ctacgcagcg ttgcggccgc tgaagatcga tctcgacg                48
```

<210> SEQ ID NO 216
<211> LENGTH: 53
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (14)..(28)
<223> OTHER INFORMATION: T7 promter

<400> SEQUENCE: 216
gcctcctatg aaaaaataac agatatagtc tccctatagt gagtcgtatt agg        53

<210> SEQ ID NO 217
<211> LENGTH: 31
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (7)..(12)
<223> OTHER INFORMATION: BglII restriction site

<400> SEQUENCE: 217
ggtggtagat ctatgagcaa aggtgaagaa c        31

<210> SEQ ID NO 218
<211> LENGTH: 29
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (7)..(14)
<223> OTHER INFORMATION: NotI restriction site

<400> SEQUENCE: 218
ggtggtgcgg ccgcgggctt tgttagcag        29

<210> SEQ ID NO 219
<211> LENGTH: 19
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: Phosporylated nucleotide

<400> SEQUENCE: 219
atgagcaaag gtgaagaac        19

<210> SEQ ID NO 220
<211> LENGTH: 36
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: Phosporylated nucleotide

<400> SEQUENCE: 220
agatctgtgg tgtgaaaaaa taacagatat agtctc                                    36

<210> SEQ ID NO 221
<211> LENGTH: 52
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(9)
<223> OTHER INFORMATION: lpp promoter
<220> FEATURE:
<221> NAME/KEY: misc_feature
<222> LOCATION: (1)..(1)
<223> OTHER INFORMATION: Phosporylated nucleotide
<220> FEATURE:
<221> NAME/KEY: misc_feature
<222> LOCATION: (10)..(32)
<223> OTHER INFORMATION: lacO site

<400> SEQUENCE: 221
tatacttgtg gaattgtgag cggataacaa ttctatatct gttattttt ca                   52

<210> SEQ ID NO 222
<211> LENGTH: 55
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: Phosporylated nucleotide
<220> FEATURE:
<221> NAME/KEY: misc_feature
<222> LOCATION: (1)..(36)
<223> OTHER INFORMATION: lpp promoter

<400> SEQUENCE: 222
acacaaagtt ttttatgttg tcaatatttt tttgatagtg agtcgtatta ggatc              55

<210> SEQ ID NO 223
<211> LENGTH: 9
<212> TYPE: RNA
<213> ORGANISM: Escherichia coli
<220> FEATURE:
<221> NAME/KEY: rRNA
<222> LOCATION: (1)..(9)
<220> FEATURE:
<221> NAME/KEY: misc_feature
<222> LOCATION: (2)..(7)
<223> OTHER INFORMATION: Anti-Shine-Dalgarno sequence

<400> SEQUENCE: 223 accuccuua                                                                  9

<210> SEQ ID NO 224
<211> LENGTH: 9
<212> TYPE: RNA
<213> ORGANISM: Artificial Sequence
<220> FEATURE:
<223> OTHER INFORMATION: Synthetic nucleotide sequence
<220> FEATURE:
<221> NAME/KEY: rRNA
<222> LOCATION: (1)..(9)
<220> FEATURE:
<221> NAME/KEY: misc_feature
<222> LOCATION: (2)..(7)
<223> OTHER INFORMATION: Anti-Shine-Dalgarno mutation

<400> SEQUENCE: 224 auuguggua                                                                 9

<210> SEQ ID NO 225
<211> LENGTH: 23
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: Phosporylated nucleotide

<400> SEQUENCE: 225
ccttaaagaa gcgtactttg tag                                                23

<210> SEQ ID NO 226
<211> LENGTH: 23
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: Phosporylated nucleotide

<400> SEQUENCE: 226
taccacaatg atccaaccgc agg                                                23

<210> SEQ ID NO 227
<211> LENGTH: 20
<212> TYPE: DNA
<213> ORGANISM: Artificial Sequence
<220> FEATURE:
<223> OTHER INFORMATION: Synthetic primer

<400> SEQUENCE: 227
taatacgact cactataggg                                                    20

<210> SEQ ID NO 228
<211> LENGTH: 18
<212> TYPE: DNA
<213> ORGANISM: Artificial Sequence
<220> FEATURE:
<223> OTHER INFORMATION: Synthetic primer

<400> SEQUENCE: 228
actcgtcgag atcgatct                                                      18

<210> SEQ ID NO 229
<211> LENGTH: 20
<212> TYPE: DNA
<213> ORGANISM: Artificial Sequence
<220> FEATURE:
<223> OTHER INFORMATION: Synthetic primer

<400> SEQUENCE: 229
taatacgact cactataggg                                                    20

<210> SEQ ID NO 230
<211> LENGTH: 17
<212> TYPE: DNA
<213> ORGANISM: Artificial Sequence
<220> FEATURE:
<223> OTHER INFORMATION: Synthetic primer

<400> SEQUENCE: 230
ttcccagtca cgacgtt                                                    17

<210> SEQ ID NO 231
<211> LENGTH: 22
<212> TYPE: DNA
<213> ORGANISM: Artificial Sequence
<220> FEATURE:
<223> OTHER INFORMATION: Synthetic primer

<400> SEQUENCE: 231
accatgatta cggattcact gg                                              22

<210> SEQ ID NO 232
<211> LENGTH: 22
<212> TYPE: DNA
<213> ORGANISM: Artificial Sequence
<220> FEATURE:
<223> OTHER INFORMATION: Synthetic primer

<400> SEQUENCE: 232
accatgatta cggattcact gg                                              22

<210> SEQ ID NO 233
<211> LENGTH: 30
<212> TYPE: DNA
<213> ORGANISM: Artificial Sequence
<220> FEATURE:
<223> OTHER INFORMATION: Synthetic primer

<400> SEQUENCE: 233
atctcatgac caaaatccct taacgtgagt                                      30

<210> SEQ ID NO 234
<211> LENGTH: 30
<212> TYPE: DNA
<213> ORGANISM: Artificial Sequence
<220> FEATURE:
<223> OTHER INFORMATION: Synthetic primer

<400> SEQUENCE: 234
gcggttagct tttaccccctg catctttgag                                     30

<210> SEQ ID NO 235
<211> LENGTH: 18
<212> TYPE: DNA
<213> ORGANISM: Artificial Sequence
<220> FEATURE:
<223> OTHER INFORMATION: Synthetic primer

<400> SEQUENCE: 235
aggctgatac cgcccaag                                                   18

<210> SEQ ID NO 236
<211> LENGTH: 44
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (21)..(22)
<223> OTHER INFORMATION: n is a, c, g, or t

<400> SEQUENCE: 236
ctcttgggcg gtatcagcct nntatccccg gagtaccttt tatc                      44

<210> SEQ ID NO 237
<211> LENGTH: 15
<212> TYPE: DNA
<213> ORGANISM: Artificial Sequence
<220> FEATURE:
<223> OTHER INFORMATION: synthetic

<400> SEQUENCE: 237
caatgaacaa ttgga                                                    15

<210> SEQ ID NO 238
<211> LENGTH: 10
<212> TYPE: DNA
<213> ORGANISM: Artificial Sequence
<220> FEATURE:
<223> OTHER INFORMATION: synthetic

<400> SEQUENCE: 238
gataactagt                                                          10

<210> SEQ ID NO 239
<211> LENGTH: 47
<212> TYPE: RNA
<213> ORGANISM: Artificial Sequence
<220> FEATURE:
<223> OTHER INFORMATION: synthetic

<400> SEQUENCE: 239
uaggccgggu guguaagcgc agcgaugcgu ugagcuaacc gguacua                 47

<210> SEQ ID NO 240
<211> LENGTH: 51
<212> TYPE: RNA
<213> ORGANISM: Artificial Sequence
<220> FEATURE:
<223> OTHER INFORMATION: synthetic

<400> SEQUENCE: 240
ugcaaaagaa guagguagcu uaaccuucgg gagggcgcuu accacuuugu g            51

<210> SEQ ID NO 241
<211> LENGTH: 62
<212> TYPE: RNA
<213> ORGANISM: Artificial Sequence
<220> FEATURE:
<223> OTHER INFORMATION: synthetic

<400> SEQUENCE: 241
ugcaaaagaa guagguagcu uaaccuucga aaaaaaacga ugcguugagc uaaccgguac   60
ua                                                                  62

<210> SEQ ID NO 242
<211> LENGTH: 53
<212> TYPE: RNA
<213> ORGANISM: Artificial Sequence
<220> FEATURE:
<223> OTHER INFORMATION: synthetic

<400> SEQUENCE: 242
uaggccgggu guguaagcgc agaaaaaaaa aggagggcgc uuaccacuuu gug          53

<210> SEQ ID NO 243
<211> LENGTH: 53
<212> TYPE: RNA

<213> ORGANISM: Artificial Sequence
<220> FEATURE:
<223> OTHER INFORMATION: synthetic

<400> SEQUENCE: 243
ugcaaaagaa guagguagcu uaaccaaaaa augcguugag cuaaccggua cua         53

<210> SEQ ID NO 244
<211> LENGTH: 49
<212> TYPE: DNA
<213> ORGANISM: Artificial Sequence
<220> FEATURE:
<223> OTHER INFORMATION: synthetic

<400> SEQUENCE: 244
uaggccgggu guguaagcgc attttttgga gggcgcuuac cacuugug               49

<210> SEQ ID NO 245
<211> LENGTH: 49
<212> TYPE: DNA
<213> ORGANISM: Artificial Sequence
<220> FEATURE:
<223> OTHER INFORMATION: synthetic

<400> SEQUENCE: 245
uaggccgggu guguaagcgc aaaaaaagga gggcgcuuac cacuugug               49

<210> SEQ ID NO 246
<211> LENGTH: 55
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (26)..(33)
<223> OTHER INFORMATION: n is a, c, g, t or u

<400> SEQUENCE: 246
ugcaaaagaa guagguagcu uaaccnnnnn nnnugcguug agcuaaccgg uacua       55

<210> SEQ ID NO 247
<211> LENGTH: 52
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (22)..(30)
<223> OTHER INFORMATION: n is a, c, g, t or u

<400> SEQUENCE: 247
uaggccgggu guguaagcgc annnnnnnnn ggagggcgcu uaccacuuug ug          52

<210> SEQ ID NO 248
<211> LENGTH: 62
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (26)..(40)
<223> OTHER INFORMATION: n is a, c, g, t or u

<400> SEQUENCE: 248
ugcaaaagaa guagguagcu uaaccnnnnn nnnnnnnnnn ugcguugagc uaaccgguac  60

```
ua                                                                     62

<210> SEQ ID NO 249
<211> LENGTH: 53
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (22)..(31)
<223> OTHER INFORMATION: n is a, c, g, t or u

<400> SEQUENCE: 249
uaggccgggu guguaagcgc annnnnnnnn nggagggcgc uuaccacuuu gug            53

<210> SEQ ID NO 250
<211> LENGTH: 62
<212> TYPE: DNA
<213> ORGANISM: Artificial Sequence
<220> FEATURE:
<223> OTHER INFORMATION: synthetic

<400> SEQUENCE: 250
ugcaaaagaa guagguagcu uaacccaaug aacaauugga ugcguugagc uaaccgguac     60
ua                                                                    62

<210> SEQ ID NO 251
<211> LENGTH: 53
<212> TYPE: DNA
<213> ORGANISM: Artificial Sequence
<220> FEATURE:
<223> OTHER INFORMATION: synthetic

<400> SEQUENCE: 251
uaggccgggu guguaagcgc agauaacuag uggagggcgc uuaccacuuu gug            53

<210> SEQ ID NO 252
<211> LENGTH: 15
<212> TYPE: DNA
<213> ORGANISM: Artificial Sequence
<220> FEATURE:
<223> OTHER INFORMATION: synthetic

<400> SEQUENCE: 252
tgttaggcat tgaca                                                      15

<210> SEQ ID NO 253
<211> LENGTH: 15
<212> TYPE: DNA
<213> ORGANISM: Artificial Sequence
<220> FEATURE:
<223> OTHER INFORMATION: synthetic

<400> SEQUENCE: 253
aataatgaat cgtaa                                                      15

<210> SEQ ID NO 254
<211> LENGTH: 15
<212> TYPE: DNA
<213> ORGANISM: Artificial Sequence
<220> FEATURE:
<223> OTHER INFORMATION: synthetic

<400> SEQUENCE: 254
```

```
caatgaaaaa ttgga                                                   15

<210> SEQ ID NO 255
<211> LENGTH: 15
<212> TYPE: DNA
<213> ORGANISM: Artificial Sequence
<220> FEATURE:
<223> OTHER INFORMATION: synthetic

<400> SEQUENCE: 255
catgcggaat tttaa                                                   15

<210> SEQ ID NO 256
<211> LENGTH: 10
<212> TYPE: DNA
<213> ORGANISM: Artificial Sequence
<220> FEATURE:
<223> OTHER INFORMATION: synthetic

<400> SEQUENCE: 256
gatacctagt                                                         10

<210> SEQ ID NO 257
<211> LENGTH: 10
<212> TYPE: DNA
<213> ORGANISM: Artificial Sequence
<220> FEATURE:
<223> OTHER INFORMATION: synthetic

<400> SEQUENCE: 257
gaacctagac                                                         10

<210> SEQ ID NO 258
<211> LENGTH: 18
<212> TYPE: DNA
<213> ORGANISM: Artificial Sequence
<220> FEATURE:
<223> OTHER INFORMATION: synthetic

<400> SEQUENCE: 258
uucaggagga gaucuaug                                                18

<210> SEQ ID NO 259
<211> LENGTH: 12
<212> TYPE: DNA
<213> ORGANISM: Artificial Sequence
<220> FEATURE:
<223> OTHER INFORMATION: synthetic

<400> SEQUENCE: 259
auuccuccac ua                                                      12

<210> SEQ ID NO 260
<211> LENGTH: 18
<212> TYPE: DNA
<213> ORGANISM: Artificial Sequence
<220> FEATURE:
<223> OTHER INFORMATION: synthetic

<400> SEQUENCE: 260
uuccaccaca gaucuaug                                                18

<210> SEQ ID NO 261
<211> LENGTH: 12
<212> TYPE: DNA
<213> ORGANISM: Artificial Sequence
```

```
<220> FEATURE:
<223> OTHER INFORMATION: synthetic

<400> SEQUENCE: 261
augguguuac ua                                                          12

<210> SEQ ID NO 262
<211> LENGTH: 22
<212> TYPE: DNA
<213> ORGANISM: Artificial Sequence
<220> FEATURE:
<223> OTHER INFORMATION: synthetic

<400> SEQUENCE: 262
uuucauaagg aggagaucua ug                                               22

<210> SEQ ID NO 263
<211> LENGTH: 21
<212> TYPE: DNA
<213> ORGANISM: Artificial Sequence
<220> FEATURE:
<223> OTHER INFORMATION: synthetic

<400> SEQUENCE: 263
uuucaucacc acagaucuau g                                                21

<210> SEQ ID NO 264
<211> LENGTH: 22
<212> TYPE: DNA
<213> ORGANISM: Artificial Sequence
<220> FEATURE:
<223> OTHER INFORMATION: synthetic

<400> SEQUENCE: 264
uuuuuccaac cacagcacua ug                                               22

<210> SEQ ID NO 265
<211> LENGTH: 22
<212> TYPE: DNA
<213> ORGANISM: Artificial Sequence
<220> FEATURE:
<223> OTHER INFORMATION: synthetic

<400> SEQUENCE: 265
uuuuucuaac cacagaucua ug                                               22

<210> SEQ ID NO 266
<211> LENGTH: 22
<212> TYPE: DNA
<213> ORGANISM: Artificial Sequence
<220> FEATURE:
<223> OTHER INFORMATION: synthetic

<400> SEQUENCE: 266
uuuuucauaa ccuagaucua ug                                               22

<210> SEQ ID NO 267
<211> LENGTH: 22
<212> TYPE: DNA
<213> ORGANISM: Artificial Sequence
<220> FEATURE:
<223> OTHER INFORMATION: synthetic

<400> SEQUENCE: 267
uuuuuccaaa ccuagaucua ug                                               22
```